US011527317B2

(12) United States Patent
Alptekin et al.

(10) Patent No.: US 11,527,317 B2
(45) Date of Patent: Dec. 13, 2022

(54) SYSTEM AND METHOD FOR THE INTERACTIVE PROVISION OF MEAL PLANS TO OPTIMIZE HUMAN HEALTH GOALS THROUGH NUTRIENT CONSUMPTION TO ENHANCE BODY FUNCTIONS, HEALTH GOALS AND DISEASE PREVENTION

(71) Applicant: MychewIQ, Inc., Lewes, DE (US)

(72) Inventors: Cem B Alptekin, Smithtown, NY (US); William J Alptekin, Smithtown, NY (US); Megan C Alptekin, Smithtown, NY (US); Shannon E Alptekin, Smithtown, NY (US); Courtney E Alptekin, Smithtown, NY (US)

(73) Assignee: MychewIQ, Inc., Lewes, DE (US)

( * ) Notice: Subject to any disclaimer, the term of this patent is extended or adjusted under 35 U.S.C. 154(b) by 1168 days.

(21) Appl. No.: 15/998,318

(22) Filed: Aug. 3, 2018

(65) Prior Publication Data

US 2020/0043593 A1 Feb. 6, 2020

(51) Int. Cl.
*G16H 20/60* (2018.01)
*G06F 3/0482* (2013.01)
*G16H 10/40* (2018.01)
*G06F 16/2457* (2019.01)

(52) U.S. Cl.
CPC .......... *G16H 20/60* (2018.01); *G06F 3/0482* (2013.01); *G06F 16/2457* (2019.01); *G16H 10/40* (2018.01)

(58) Field of Classification Search
CPC .... G16H 20/60; G16H 10/40; G06F 16/2457; G06F 3/0482
See application file for complete search history.

(56) References Cited

U.S. PATENT DOCUMENTS

| | | |
|---|---|---|
| 7,076,438 B1 | 7/2006 | Tobelmann et al. |
| 8,234,160 B2 | 7/2012 | Brown et al. |
| 9,852,266 B2 | 12/2017 | Damani et al. |
| 2002/0147641 A1 | 10/2002 | Hickford et al. |
| 2003/0050540 A1 | 3/2003 | Miller-Kovach et al. |
| 2005/0049920 A1 | 3/2005 | Day et al. |
| 2006/0053184 A1 | 3/2006 | Grana |
| 2006/0074716 A1 | 4/2006 | Tilles et al. |
| 2006/0199155 A1 | 9/2006 | Mosher |
| 2007/0136093 A1 | 6/2007 | Rankin et al. |
| 2008/0076637 A1 | 3/2008 | Gilley et al. |
| 2009/0075242 A1 | 3/2009 | Schwarzberg et al. |
| 2011/0124978 A1 | 5/2011 | Williams |

(Continued)

*Primary Examiner* — William L Bashore
*Assistant Examiner* — Gregory A Distefano

(57) ABSTRACT

The invention provides a system and method for the Interactive input of information and generation of data that may provide for provision of meal plans and an optimizer score to optimize human health goals through nutrient consumption to enhance body functions, health goals and disease prevention. A computer system may be provided to communicate using a communication network that may provide software configured to develop a user profile based upon user information entered by the user including in connection with health goals, health information and meal, raw food and ingredients that may be developed by the software based upon user information and searching of the data bases of the present invention.

24 Claims, 59 Drawing Sheets

(56) References Cited

U.S. PATENT DOCUMENTS

| | | |
|---|---|---|
| 2012/0094258 A1 | 4/2012 | Langheier et al. |
| 2013/0224694 A1* | 8/2013 | Moore ............... G09B 19/0092 434/127 |
| 2014/0019218 A1 | 1/2014 | Brown et al. |
| 2014/0180847 A1 | 6/2014 | Silverstein et al. |
| 2014/0221785 A1 | 8/2014 | Pacione et al. |
| 2014/0249966 A1 | 9/2014 | Zaragoza et al. |
| 2014/0324459 A1* | 10/2014 | Barfield ................ G16H 40/67 705/3 |
| 2015/0093725 A1* | 4/2015 | Baarman .................. G09B 5/00 600/300 |
| 2018/0240359 A1* | 8/2018 | Hujsak ................... G06N 20/00 |
| 2019/0130786 A1* | 5/2019 | Kumbakonam ....... G09B 5/065 |

* cited by examiner

Partially obscured word "Disease" has been corrected

Partially obscured word "Disease" has been corrected

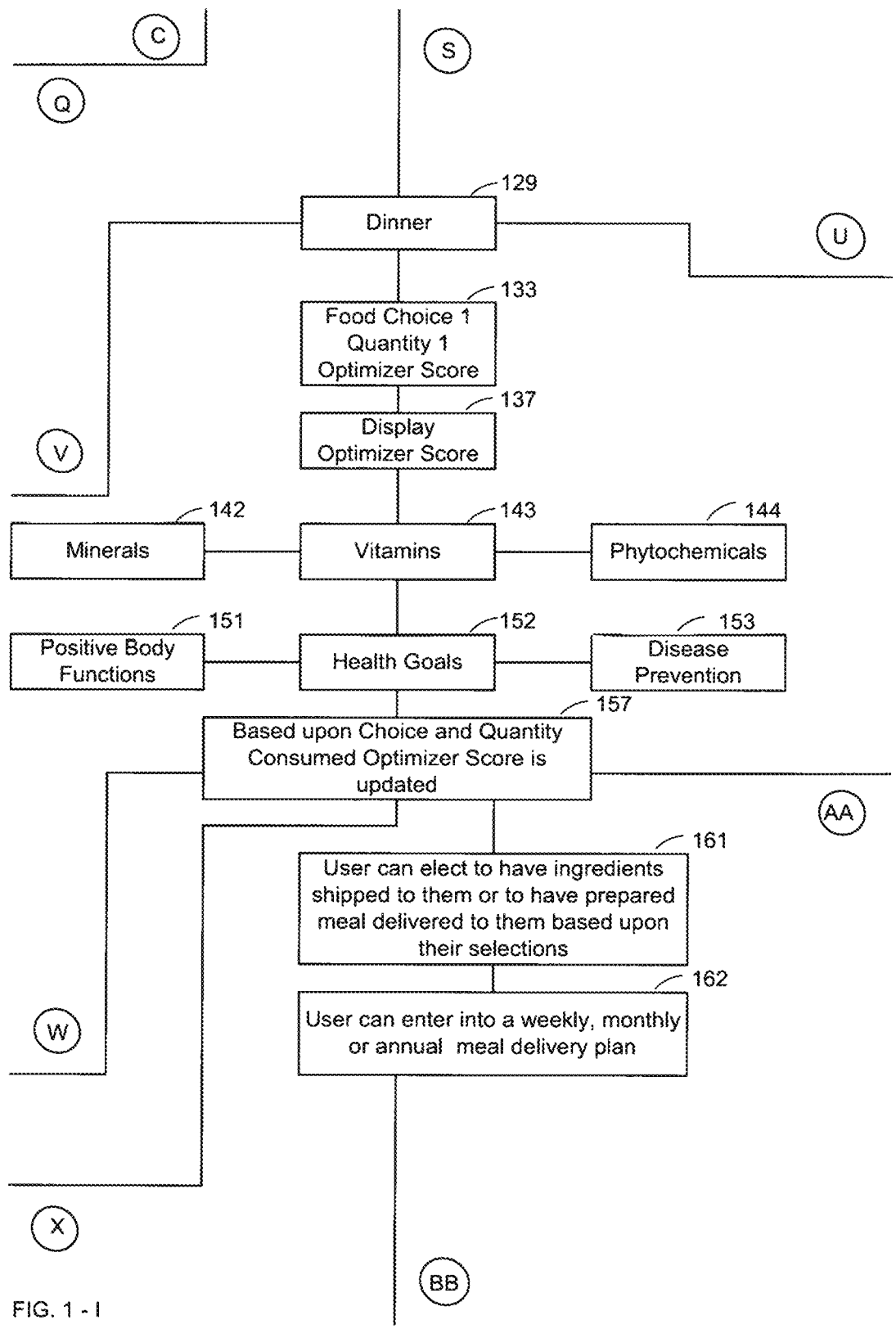
FIG. 1 - I

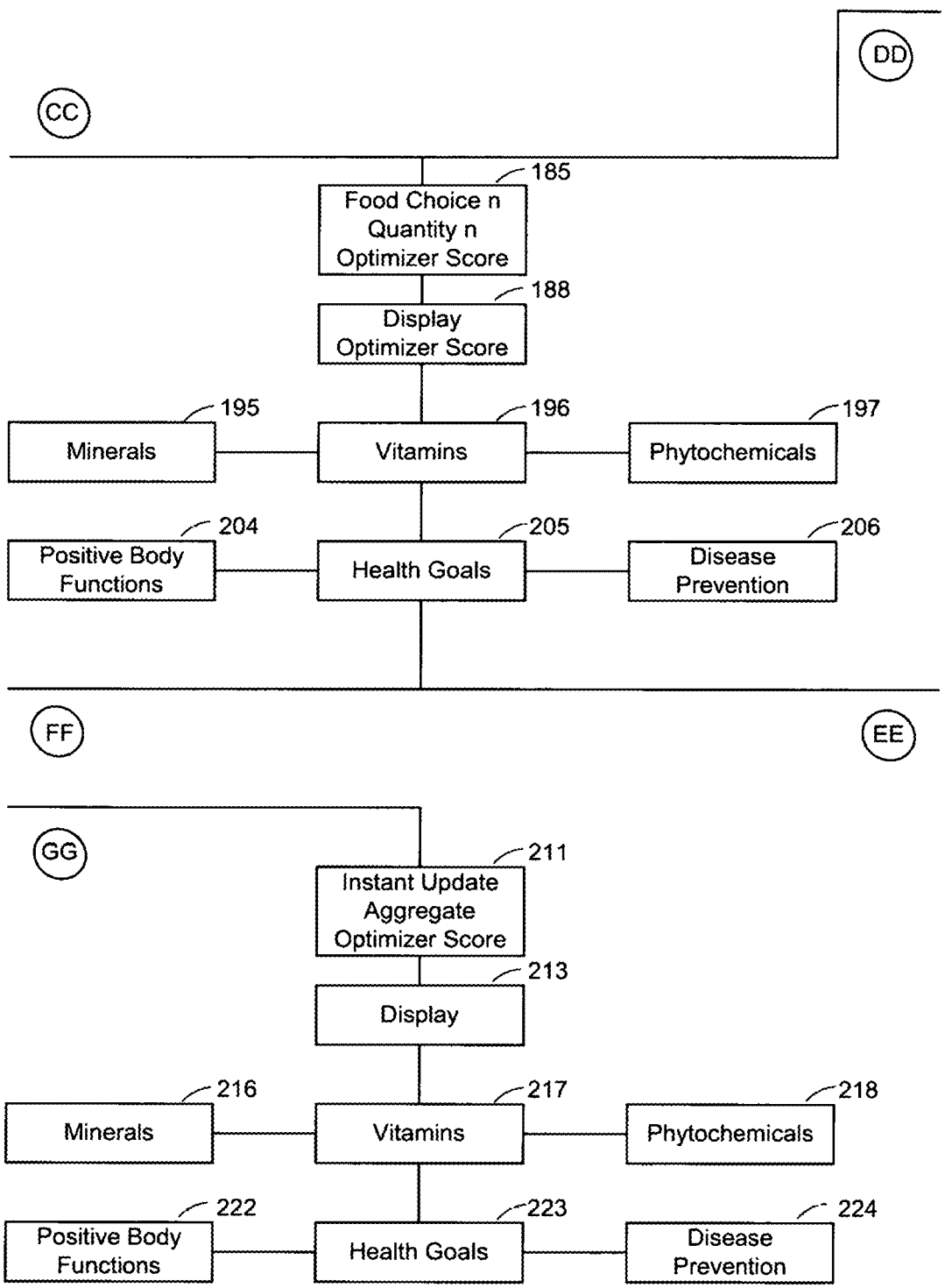
FIG. 1-O

| | |
|---|---|
| PH | 3.5 |
| Calories | 350 or 15% of daily recommended amount |
| LDL Cholesterol | 30% of daily recommended amount |
| Salt | 25% of daily recommended amount |
| Sugar | 50% of daily recommended amount |

FIG. 10G

SYSTEM AND METHOD FOR THE INTERACTIVE PROVISION OF MEAL PLANS TO OPTIMIZE HUMAN HEALTH GOALS THROUGH NUTRIENT CONSUMPTION TO ENHANCE BODY FUNCTIONS, HEALTH GOALS AND DISEASE PREVENTION

FIELD OF INVENTION

The invention relates to the interactive provision of advice in response to input information to enhance human health goals that may include enhancement or positive body functions, disease protection and ingestion of enhancing phytochemicals, vitamins and minerals; this may be implemented through the provision of raw foods, ingredients and meal plans to enhance the health goals. A Web-based application may be provided as a resource to aid in the optimization of the advice to enhance human health goals. The computer application software may receive, transmit and compute data for smartphones and mobile devices in the fields of human dietary consumption, medicine, health and wellness.

BACKGROUND OF THE INVENTION

The are many businesses promoting methods of guidance regarding dietary consumption that are based upon "counting calories". These existing methods do not take a complete approach to human dietary consumption and health.

For instance, a user of an existing method may rely on the fact that celery is low in calories and therefore they primarily eat celery for breakfast, lunch and dinner. The user is not alerted to the fact that there are many more nutrients the body needs to optimize one's health.

MychewIQ is an intelligent method of approaching human dietary consumption and overall health. The data regarding the vitamins, minerals, phytochemicals, positive body functions and disease prevention qualities of foods are all analyzed and the user is provided with recommended foods and an automated method of tracking their daily dietary consumption such that the human body's health is optimized.

SUMMARY OF THE INVENTION

A method, system and software are provided for the interactive provision of meal plans that may include a computerized system for receiving user information that may include health information, laboratory tests, and desired human health goals. A user profile may be developed from which healthy meal plans may be developed to achieve the health goals and include user input of meal preferences amending computer generated meal options where rating values are generated for the selected meal plans insofar as achieving the human health goals.

The user may utilize computer generated research tools to enable improved meal plan selections and display how the selected meals effect laboratory information such as sodium level, potassium level, glucose level, cholesterol level, HDL, LDL, PSA level TSH level, PH level, vitamin D, vitamin B12, CRP levels and combinations of the foregoing. The human heath goals selected by the user may include, for example, healthy vision, building muscle, having more energy, healthy immune system hair growth, healthy skin, healthy nails, healthy heart, weight-loss, managing blood pressure, managing cholesterol, mental sharpness, PH level, cancer fighters, anti-inflammation, healthy bones, enhanced metabolism, fighting type 2 diabetes or combinations of the foregoing. The positive body functions may include cancer protection, anti-inflammatory protection, antioxidant effects, reduced bone loss, immunity boosters, reduced LDL cholesterol, heart healthy achievements or combinations of the foregoing. Disease prevention may include diseases related to cancer, type 2 diabetes, osteoporosis, cardiovascular inflammation, obesity or combinations of the foregoing.

Another embodiment may include either the shipment to the user of the various selected meals, raw foods, ingredients to make the selected meals or combinations of the foregoing.

The rating score for the meals, meal plans, raw foods and/or ingredients selected may preferably be an optimizer score that mimics IQ styled ratings. The optimizer score may be calculated from a formula such as:

$$OS = (\% \ DRA(M) \times 20) + (\% \ DRA(V) \times 20) + (\% \ DRA(P) \times 20) + (\% \ DRL(PBF) \times 20) + (\% \ DRL(HG) \times 20) + (\% \ DRL(DP) \times 20) + (\% \ DRL(PH) \times 20) - [(\% \ over \ DL(C) \times 10) + (\% \ over \ DL(SA) \times 10) + (\% \ over \ DL(LDL) \times 10) + (\% \ over \ DL(SU) \times 10)]$$

Where:
'OS' is the Optimizer Score
'DRA' is Daily required amount
'M' is Minerals, such as Calcium, Iodine, Iron, Magnesium, Manganese, Phosphorous, Potassium, Selenium, Sodium and Zinc
'V' is Vitamins, such as Vitamin A, Vitamin B1, Vitamin B2, Vitamin B3, Vitamin B6, Vitamin B12, Vitamin C, Vitamin D, Vitamin E and Vitamin K
'P' is Phytochemicals, such as Polyphenols, lycopene, Lutein, Phytosterols, Saponins, Phenols, Flavonoids, Isothiocyanates, Ferulic Acid, Indoles
'PBF' is Positive Body Function, such as Healthy Vision, Healthy Skin, Healthy Nails, Cancer (Protection, Anti Inflammatory, Antioxidant, Reduction in Bone Loss, Immunity Booster, Reduction in LDL Cholesterol and Heart Healthy
'DRL' is Daily Required Level
'HG' is Health Goals, such as Build Muscle, More Energy, Hair Growth, Weight Loss, Manage Blood Pressure, Manage Cholesterol, Mental Sharpness, Cancer Fighter, Enhance Metabolism and Fight Type 2 Diabetes
'DP' is Disease Prevention, such as Cancer, Type 2 Diabetes, Osteoporosis, Cardiovascular, Inflammation and Obesity
'PH' is PH—the acidity or alkalinity measurement
'DL' is Daily Limit
'C' is Calories
'SA' is Salt
'LDL' is LDL Cholesterol
'SU' is Sugar As a user selects from suggested foods and quantities or inputs foods and quantities into the software application, the user's optimizer score is updated and future suggested choices for foods are generated based upon foods that were previously consumed that day or to enhance the optimizer score. The algorithm will calculate the nutritional value of the food, the positive body functions, health goals and disease prevention that the food contributes towards. The user will always be guided via computer generated advice toward foods that will maximize the user's overall health, thereby maximizing their optimizer score.

The optimizer score may yield different levels of ratings that may include scores of 140 or over for the genius level, 120-139 for the smarty pants level, 110-119 for the bright level, 90-109 for the average level, 70-89 for the slacker level, 40-69 for the blockhead level and below 40 for the fool level.

In another embodiment a computer system is provided which is adapted to communicate with a communication network wherein the software is configured to develop a user profile based upon user information inputted by the user including information relative to human goals and meal plans, raw foods and ingredients that are inputted. The software may further configured to identify compliant meals, raw foods and ingredients from the inputted information, transmit same to the user via the communications network and receive from the user the user selections and compute a rating value that may be transmitted back to the user.

The computer system may communicate with various data bases that may include those for: disease prevention, food nutrition, healthy body function and partner food, ingredient and meals suppliers. It may transmit via the communication network to connected tablets, smart phones, smart devices, smart watches via CPU and communication network such information that may include minerals, vitamins, phytochemicals, positive body functions, benefit for meeting custom health goals, disease prevention capabilities, PH levels, calories, salt level, sugar level and cholesterol level in each meal, raw food and/or ingredient for a meal. Further, the information transmitted may be adjusted including for the quantity of selected food, meal or ingredient. Accordingly, for example, the software may configured to transmit to the user, the daily cumulative amount of vitamins, minerals, phytochemicals, positive body functions benefits towards achieving custom health goals, disease prevention capabilities, PH level, calories, salt level, sugar level and cholesterol level based upon the quantities of meals, raw foods, ingredients eaten. Further, the software is configured to transmit to the user what meals, raw foods, ingredients for the meals and quantities are needed to maximize the user's optimizer score for the balance of the day. The software may also be configured to transmit to the user recommended meals, raw foods and ingredients that user will enjoy and will maximize user's optimizer score based upon prior meal, raw foods and ingredient selections. The software may also transmit to the user the foods and meals as well as their constituent elements associated with user's health goals. The software is configured to receive from the user favorite foods, ingredients and meals whereupon these favorites may be included in suggested foods and meals subsequently transmitted to the user. The software may also be configured to reverse engineer the choice of foods, ingredients and meals that will help user achieve user's health goals.

In one embodiment the computer system may comprise a microprocessor, a memory coupled to the microprocessor, a network interface device operatively connected to the microprocessor for communicating via a communications network and instructions stored in the memory and executable by the microprocessor. These instructions may, for example, develop a profile for user responsive to receipt of user information, said profile being defined as a function of the human health goals and other user input information, said profile including the development of food and meal choices; search databases to determine that the profile meets the human health goals and other user input information; identify compliant foods, ingredients, meals and rated values for same, to allow user to input his selection of foods, ingredients and meals; transmit to user via the communications network information associated with the compliant meals and rated values; and allow for interactive transmittal of information between the user and the system.

The system may further comprise instructions stored in the memory and executable by the microprocessor to compute the rated values pursuant to the formula:

$$OS = (\% \; DRA(M) \times 20) + (\% \; DRA(V) \times 20) + (\% \; DRA(P) \times 20) + (\% \; DRL(PBF) \times 20) + (\% \; DRL(HG) \times 20) + (\% \; DRL(DP) \times 20) + (\% \; DRL(PH) \times 20) - [(\% \; over \; DL(C) \times 10) + (\% \; over \; DL(SA) \times 10) + (\% \; over \; DL(LDL) \times 10) + (\% \; over \; DL(SU) \times 10)]$$

Where:
'OS' is the Optimizer Score; DRA' is Daily required amount; 'M' is Minerals, such as Calcium, Iodine, Iron, Magnesium, Manganese, Phosphorous, Potassium, Selenium, Sodium and Zinc; 'V' is Vitamins, such as Vitamin A, Vitamin B1, Vitamin B2, Vitamin B3, Vitamin B6, Vitamin B12, Vitamin C, Vitamin D, Vitamin E and Vitamin K; 'P' is Phytochemicals, such as Polyphenols, Lycopene, Lutein, Phytosterols, Saponins, Phenols, Flavonoids, Isothiocyanates, Ferulic Acid, Indoles; 'PBF' is Positive Body Function, such as Healthy Vision, Healthy Skin, Healthy Nails, Cancer Protection, Anti-Inflammatory, Antioxidant, Reduction in Bone Loss, Immunity Booster, Reduction in LDL Cholesterol and Heart Healthy Protections; 'DRL' is Daily Required Level; 'HG' is Health Goals, such as Build Muscle, More Energy, Hair Growth, Weight Loss, Manage Blood Pressure, Manage Cholesterol, Mental Sharpness, Cancer Fighter, Enhance Metabolism and Fight Type 2 Diabetes; 'DP' is Disease Prevention, such as Cancer, Type 2 Diabetes, Osteoporosis, Cardiovascular, Inflammation and Obesity; 'PH' is PH—the acidity or alkalinity measurement; 'DL' is Daily Limit; 'C' is Calories; 'SA' is Salt; 'LDL' is LDL Cholesterol; and 'SU' is Sugar.

BRIEF DESCRIPTION OF THE DRAWINGS

FIG. 1A includes the user welcome screen, an introduction to the health goals and the breakfast display; FIG. 1-I includes the dinner display and the option to have food shipped to the user; FIG. 1-O includes the instant aggregate optimizer score after snack and food choice n for snack; FIG. 1Q includes the aggregate optimizer score for the day and the resulting levels moniker;

FIG. 3A includes the user welcome screen; FIG. 3B includes the option to have food, either in a raw form or a prepared meal, delivered to the user; FIG. 3C includes meal option 1 and the related optimizer score; FIG. 3D includes meal option 2 and the related optimizer score; FIG. 3E includes meal option n and the related optimizer score;

FIG. 6A includes the user welcome screen and the input for the user demographics; FIG. 6B includes four health goals and their respective associated foods; FIG. 6C includes another four health goals and their respective associated foods; FIG. 6D includes the health goal display with the option to enter laboratory information another five health goals and their respective associated foods; FIG. 6E includes another four health goals and their respective associated foods; FIG. 6F includes the last health goal and its respective associated foods; FIG. 6G includes the option to include foods in their meal plans and as favorites;

FIG. 7A includes user welcome screen and the option to enter laboratory information; FIG. 7B includes two laboratory tests and their respective associated foods; FIG. 7C includes another four laboratory tests and their respective associated foods; FIG. 7D includes another four laboratory tests and their respective associated foods; FIG. 7E includes the last four laboratory tests and their respective associated foods; FIG. 7F includes the option to include foods in their meal plans and as favorites;

FIG. 8A includes the option to enter in a food and quantity and the health data will be displayed; FIG. 8B includes the Minerals in the inputted food and the percent of the daily required amount as well as the foods and amounts that can be consumed to complete the daily required amount; FIG. 8C includes the Vitamins in the inputted food and the percent of the daily required amount as well as the foods and amounts that can be consumed to complete the daily required amount; FIG. 8D includes the Phytochemicals in the inputted food and the percent of the daily required amount as well as the foods and amounts that can be consumed to complete the daily required amount; FIG. 8E includes the Positive Body Functions resulting from the inputted food and the percent of the daily required amount as well as the foods and amounts that can be consumed to complete the daily required amount; FIG. 8F includes the Health Goals impacted by the inputted food and the percent of the daily required amount as well as the foods and amounts that can be consumed to complete the daily required amount; FIG. 8G includes the Disease Prevention impacted by the inputted food and the percent of the daily required amount as well as the foods and amounts that can be consumed to complete the daily required amount;

FIG. 9A includes the user welcome screen to researching which foods best represent each health data category; FIG. 9B includes Minerals 1,2, n and their respective associated foods and the ability to have the food entered into the user's meal plan and favorites; FIG. 9C includes Vitamins 1,2, n and their respective associated foods and the ability to have the food entered into the user's meal plan and favorites; FIG. 9D includes Phytochemicals 1,2, n and their respective associated foods and the ability to have the food entered into the user's meal plan and favorites; FIG. 9E includes Positive Body Functions 1,2, n and their respective associated foods and the ability to have the food entered into the user's meal plan and favorites; FIG. 9F includes Health Goals 1,2, n and their respective associated foods and the ability to have the food entered into the user's meal plan and favorites; FIG. 9G includes Disease Prevention 1,2, n and their respective associated foods and the ability to have the food entered into the user's meal plan and favorites; and FIGS. 10A-G shows the graphs and updates that may be generated regarding the data associated with the foods and respective quantity of food they are considering eating or have eaten; FIG. 10A includes the Minerals graph; FIG. 10B includes the Vitamins graph; FIG. 10C includes the Phytochemicals graph; FIG. 10D includes the Positive Body Functions graph; FIG. 10E includes the Health Goals graph; FIG. 10F includes the Disease Prevention graph; FIG. 10G includes the PH, Calories, LDL Cholesterol, Salt and Sugar update.

DETAILED DESCRIPTION

The present invention may be a Web-based application used as a resource to optimize human health goals. The computer application software receives, transmits and computes data for smartphones and mobile devices in the fields of human dietary consumption, medicine, health and wellness.

Figure 4:
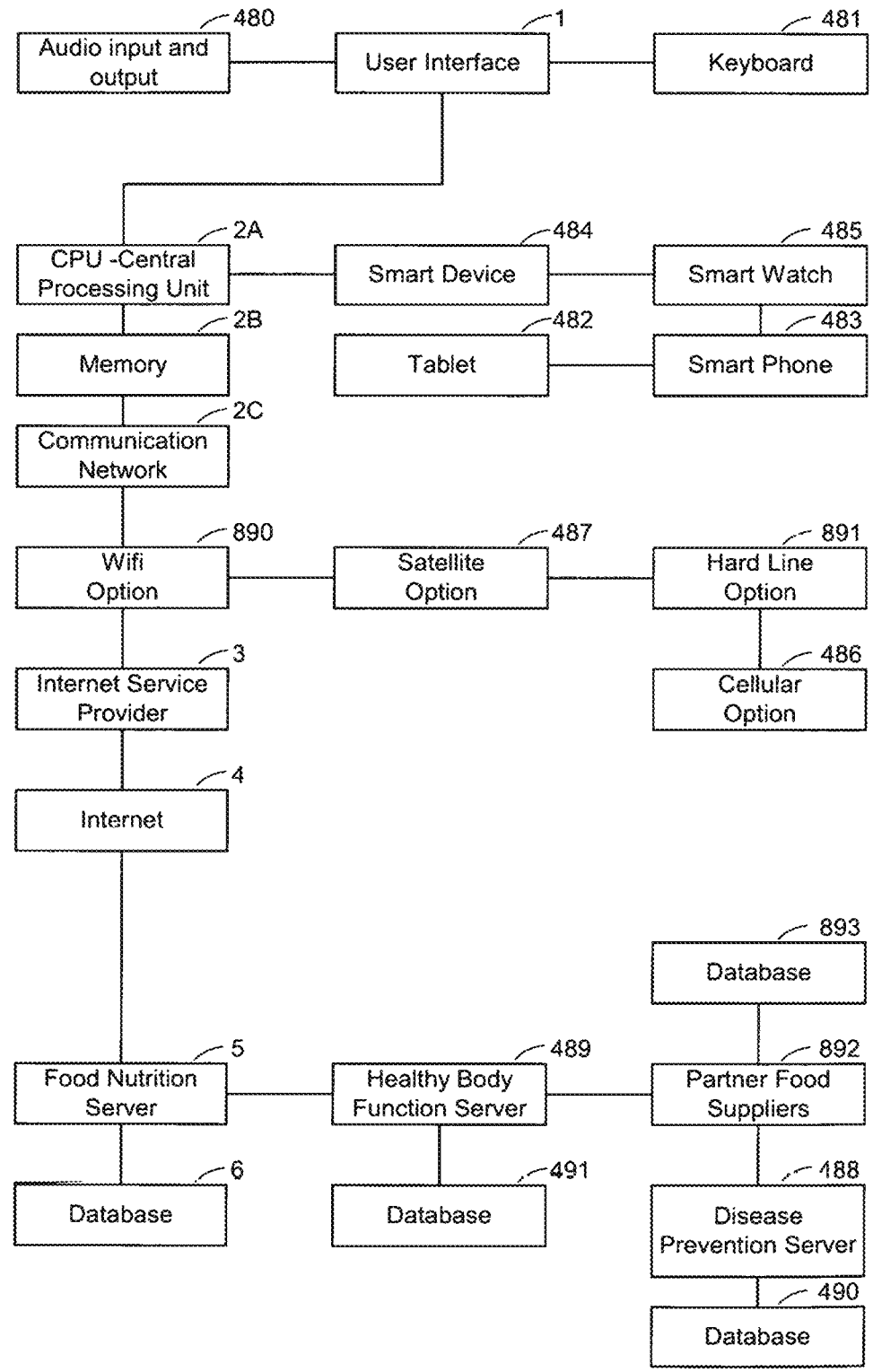
FIG. 4 is a flow chart that shows the computer hardware that is part of the process of allowing the user to interact with the software application in accordance with the present invention.

In FIG. 4 the method by which the user may interact with the algorithm, which is developed as part of a software application, can be visualized. The user interface 1, Audio input and output 480 and Keyboard 481 are part of a Central Processing Unit (CPU) 2A that may include an tablet 482 or smart phone 483 or smart device 484 or smart watch 485 that is connected to a communications network 2C which may include an Internet Service Provider 3, cellular network x, blue tooth network y or any other wireless or hard wired network (not shown). Examples of the communication network 2C may be achieved through a cellular option 486, wifi option 890, satellite option 487 or Hard Line option 891. Once connected to the communications network, the remote Food Nutrition Server 5 and respective Database 6, Disease Prevention Server 488 and respective Database 490, Healthy Body Function Server 489 and respective Database 491, Partner Food Supplier Server 892 and Database 893 can be accessed by the user. Once connected to the communication network 2C, the user may download the present invention, software application, on to their Central Processing Unit (CPU) 2A that may include tablet 482 or smart phone 483 or smart device 484 or smart watch 485. As the user interacts with the software application, data is transmitted between the Central Processing Unit (CPU) 2A or tablet 482 or smart phone 483 or smart device 484 or smart watch 485 and Food Nutrition Server 5 and respective Database 6, Disease Prevention Server 488 and respective Database 490, Healthy Body Function Server 489 and respective Database 491, Partner Food Supplier Server 892 and respective Database 893

Figure 1A:
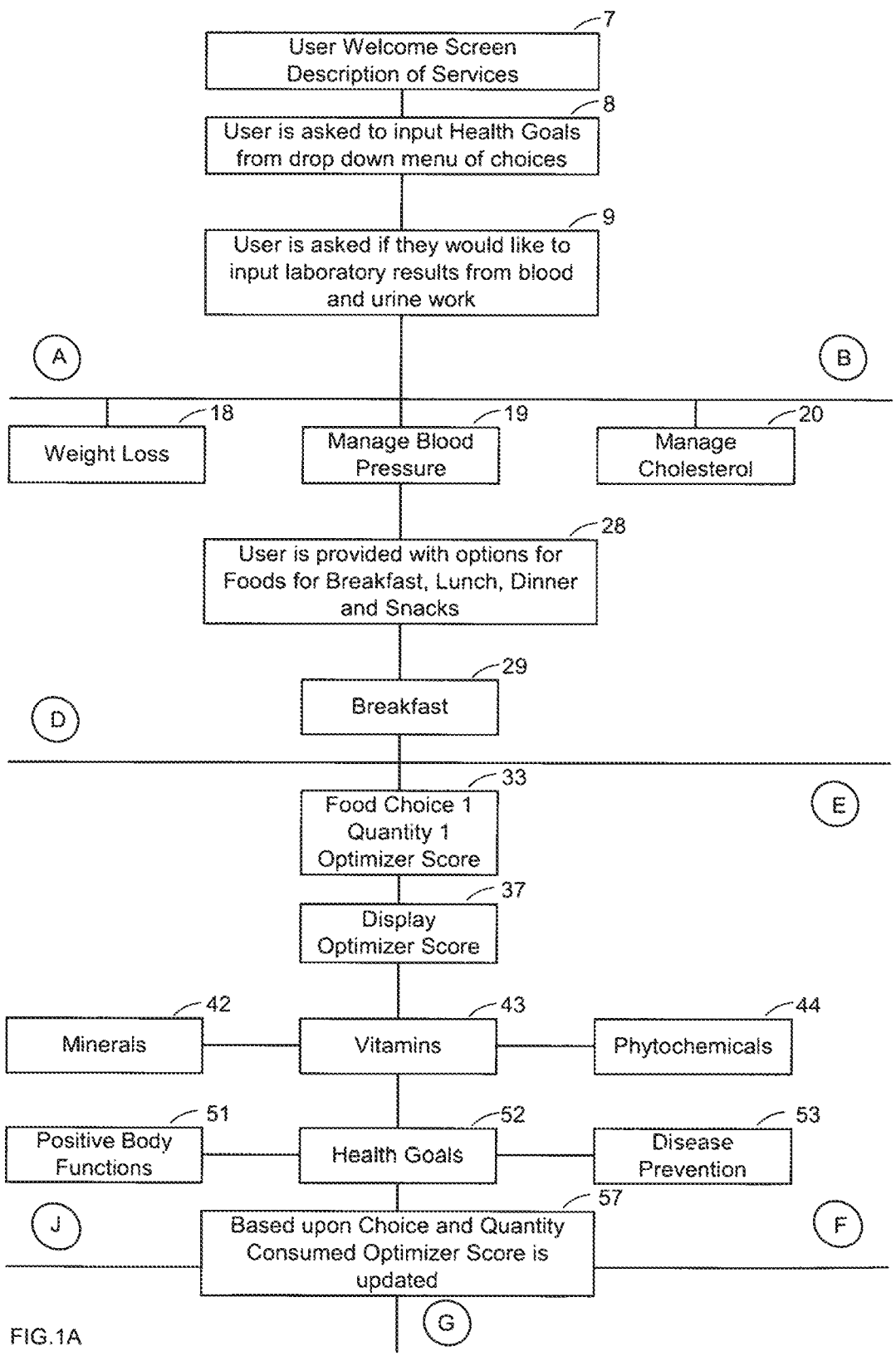
FIGS. 1A-Q are components of a flow chart that shows overall how the user would interact with the software application to select their health goals; how meal selection would take place; the custom options available; the information provided to the user for each food option; the Optimizer Score levels.
Figure 1B:
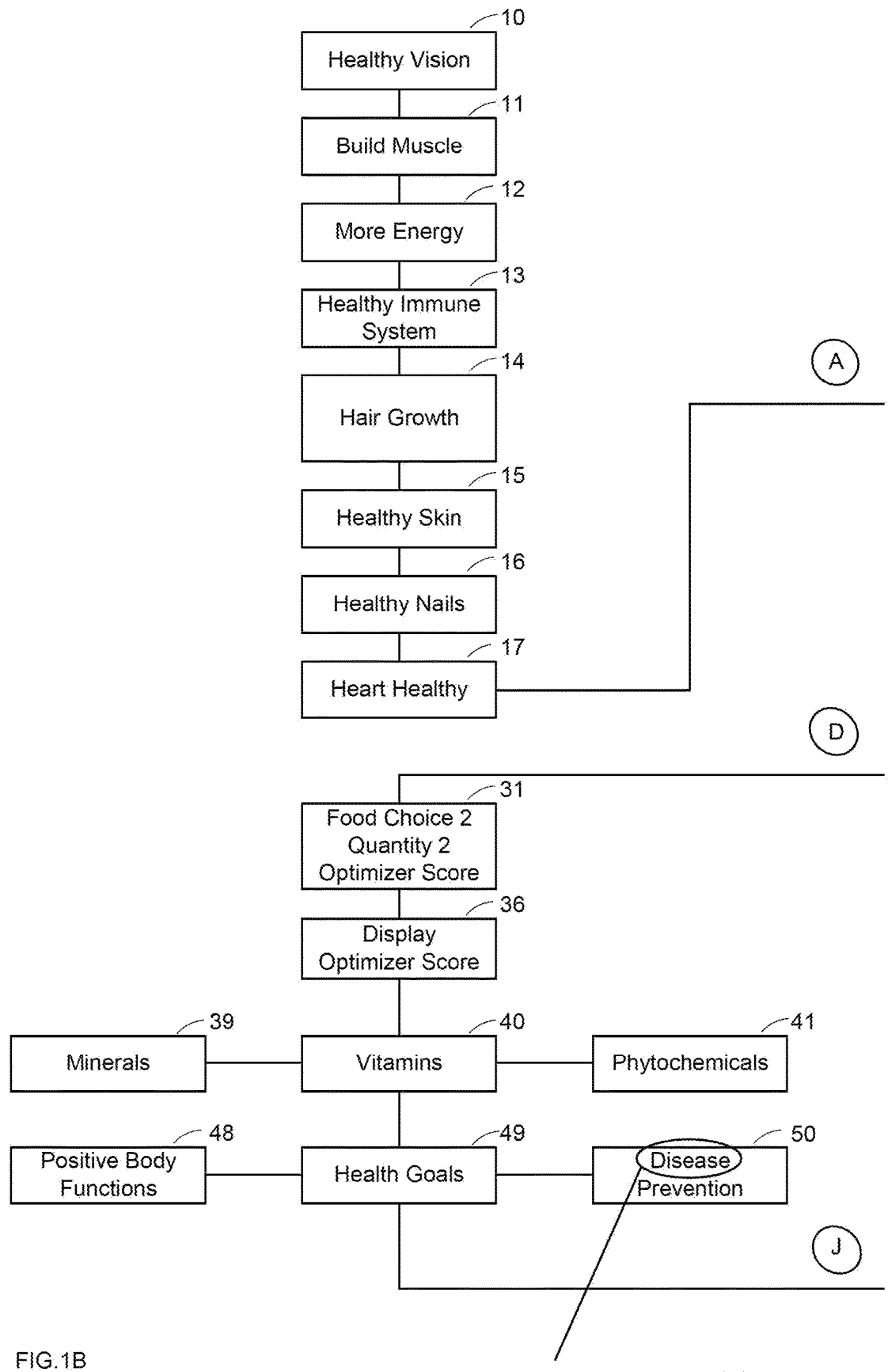
FIG. 1B includes some of the health goals and food choice 2 for breakfast.
Figure 1C:
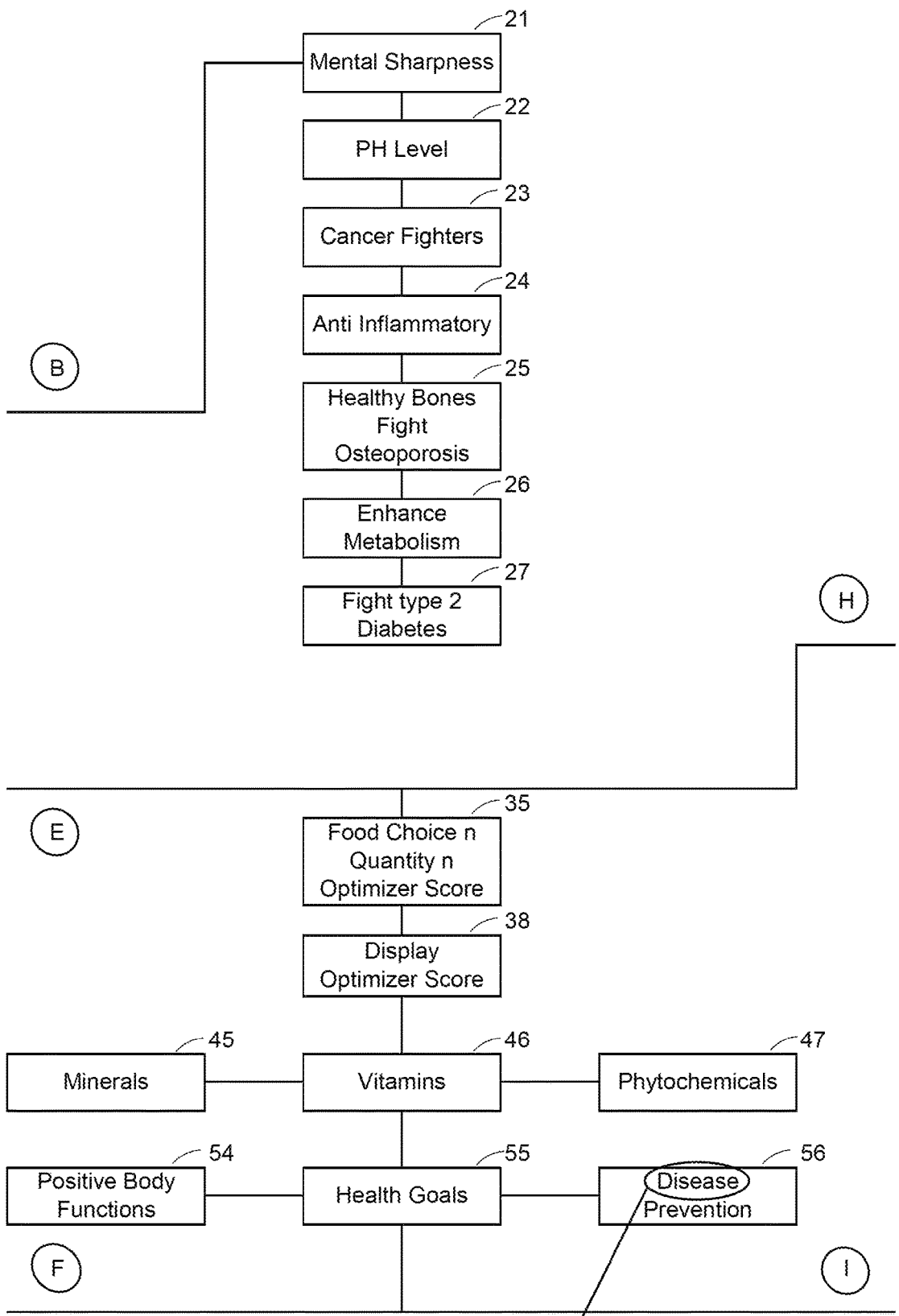
FIG. 1C includes the balance of the health goals and food choice n for breakfast.
Figure 1D:
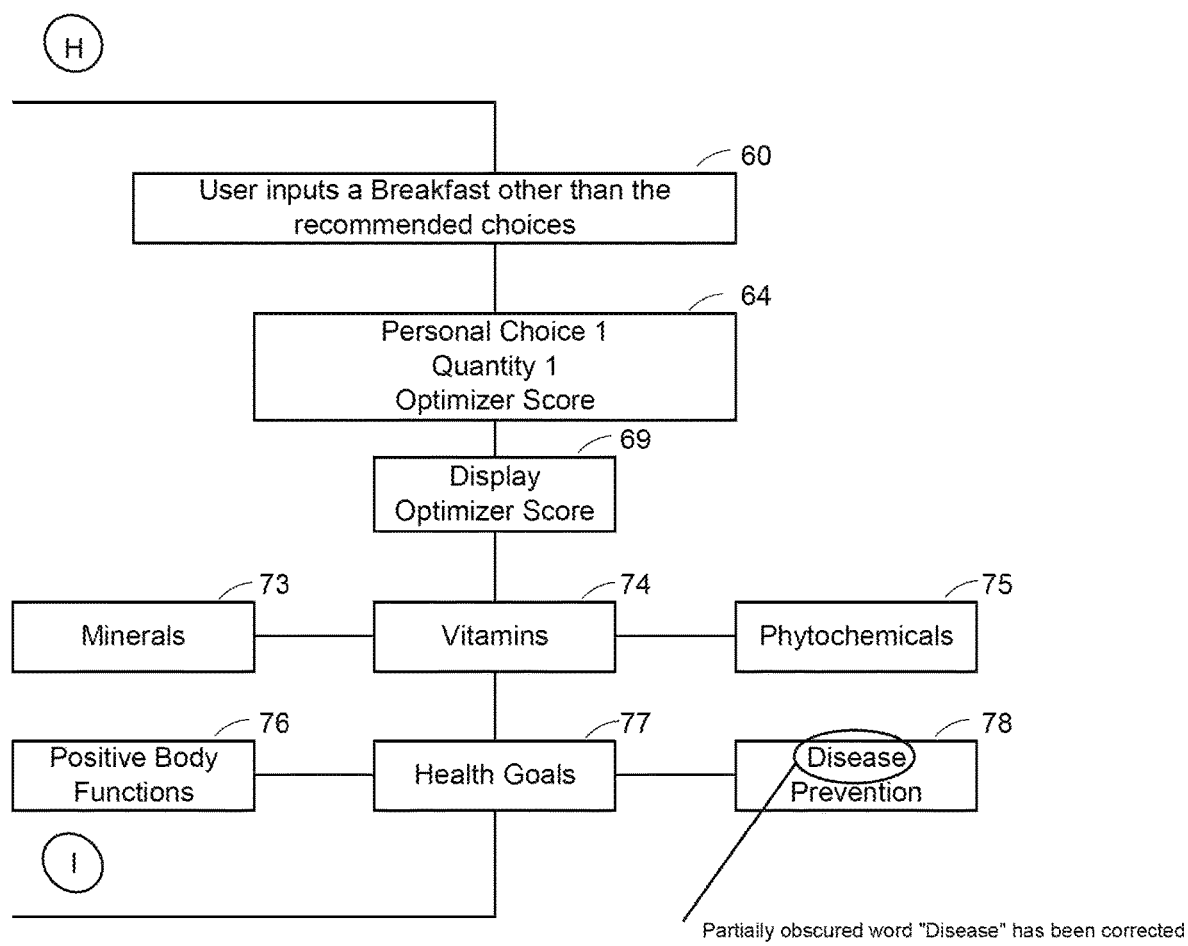
FIG. 1D includes the user's ability to input a food choice other than what is suggested for breakfast.
Figure 1E:
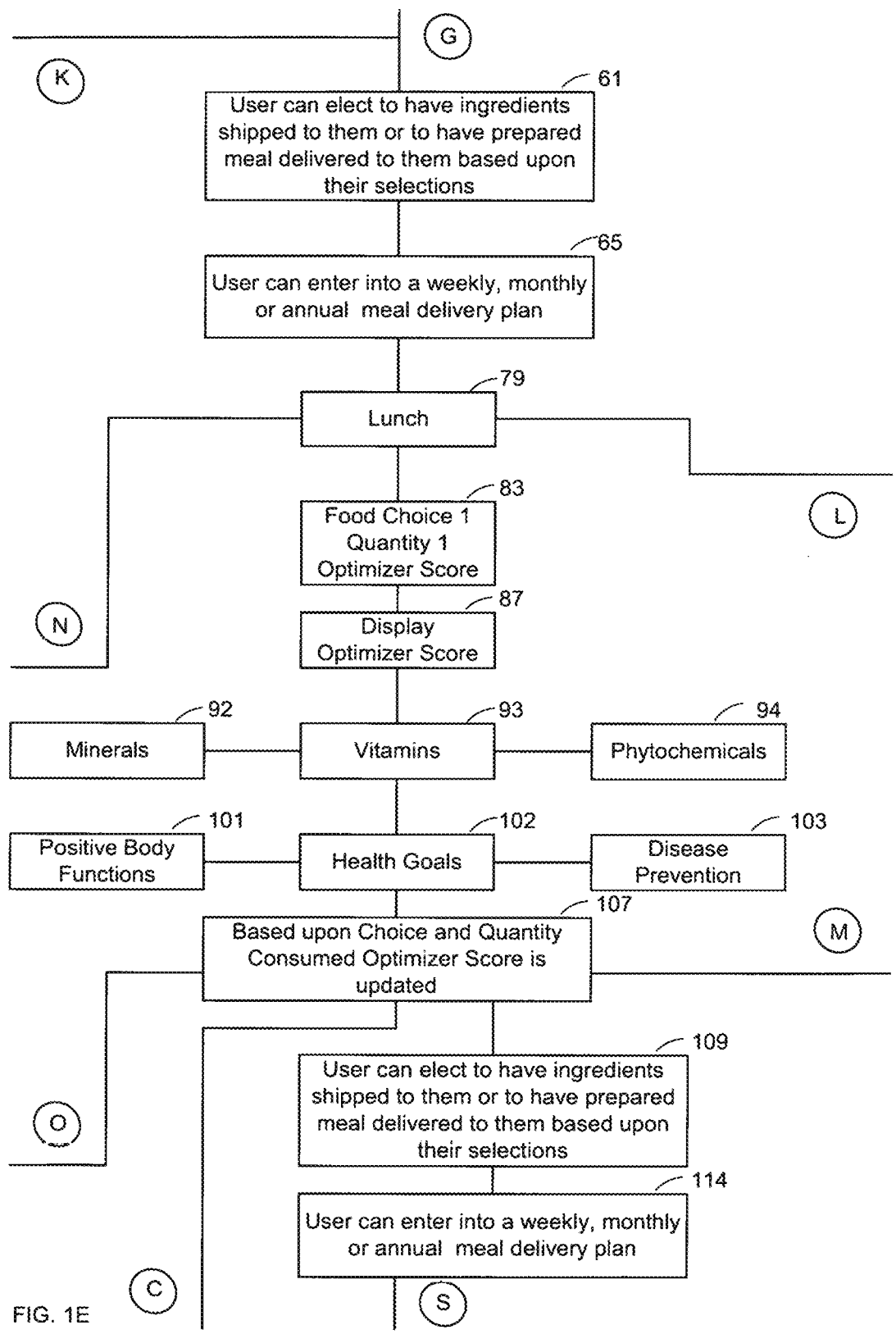
FIG. 1E includes the option to have food shipped to the user from breakfast and the lunch display.
Figure 1F:
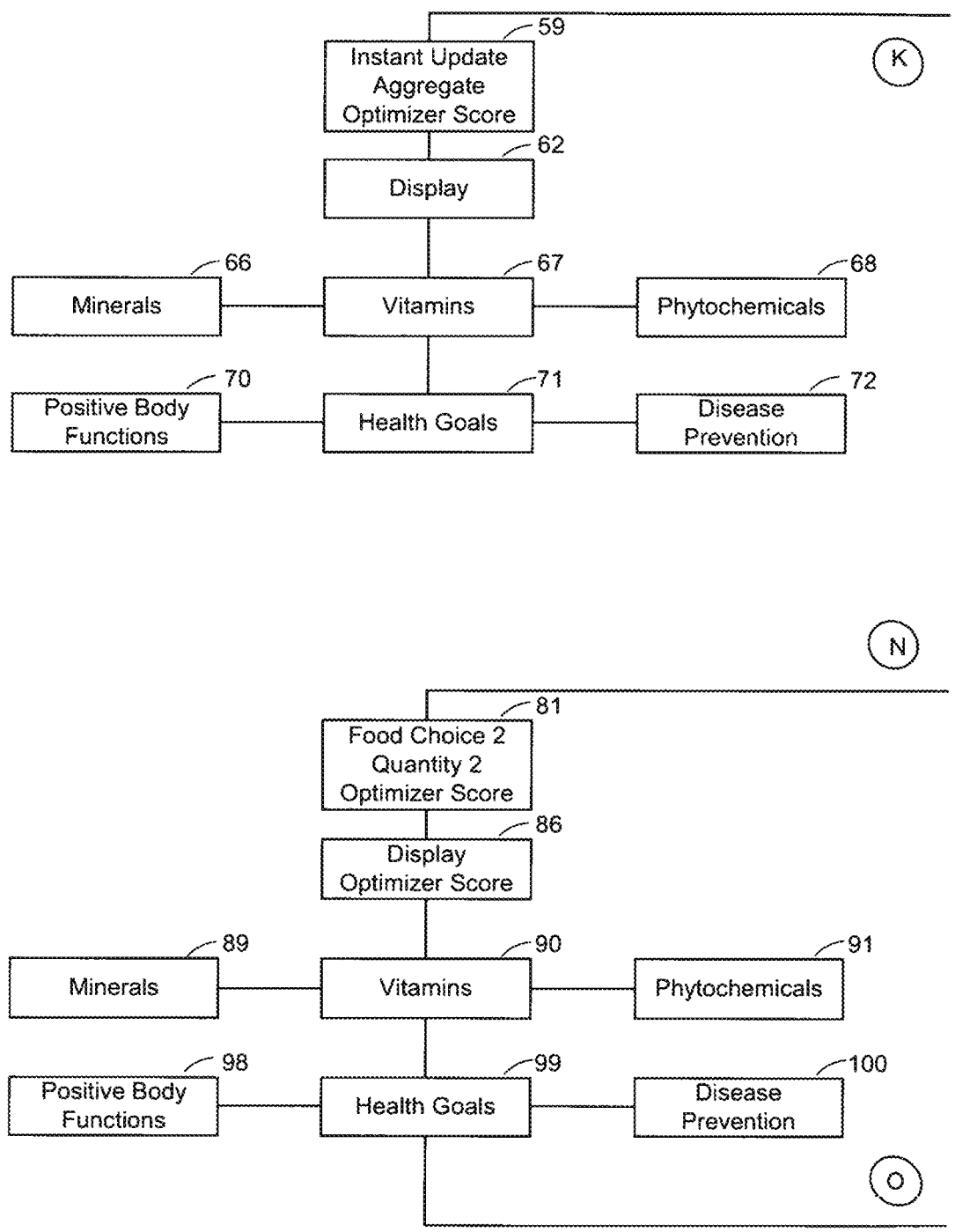
FIG. 1F includes the instant update aggregate optimizer scope after breakfast and food choice 2 for lunch.
Figure 1G:
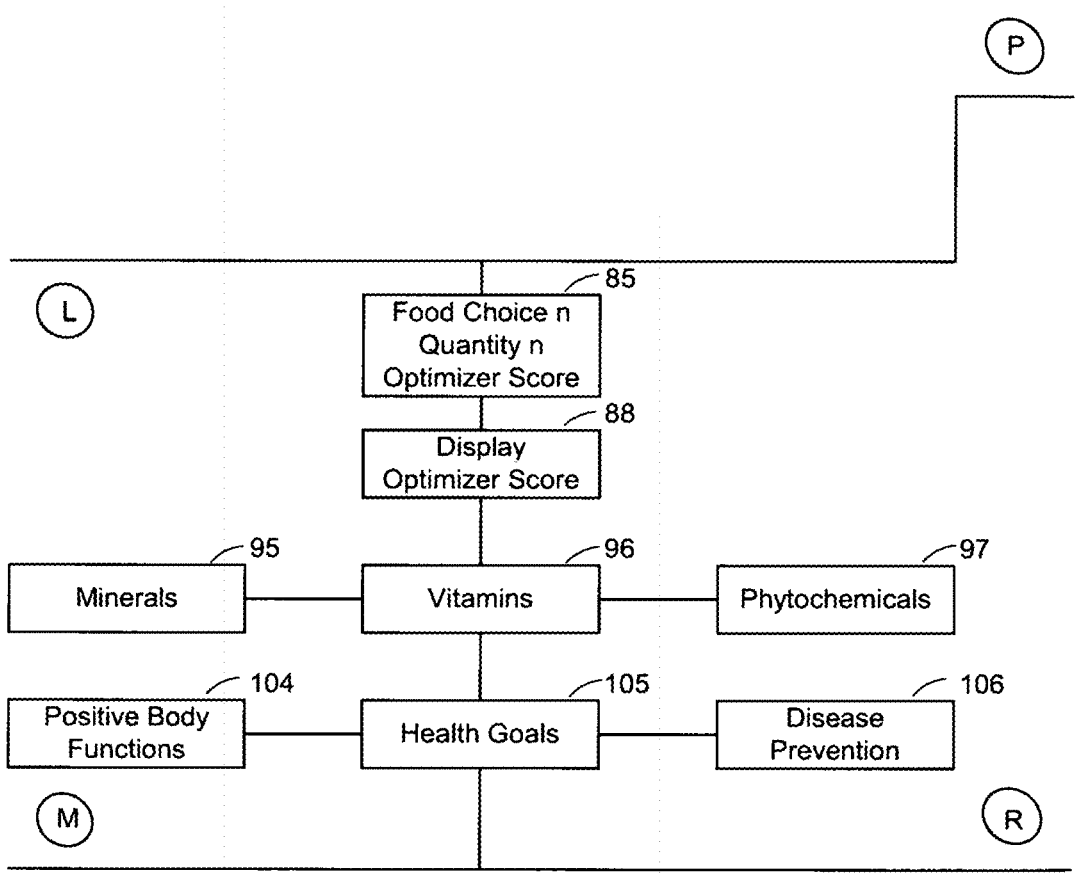
FIG. 1G includes food choice n for lunch.
Figure 1H:
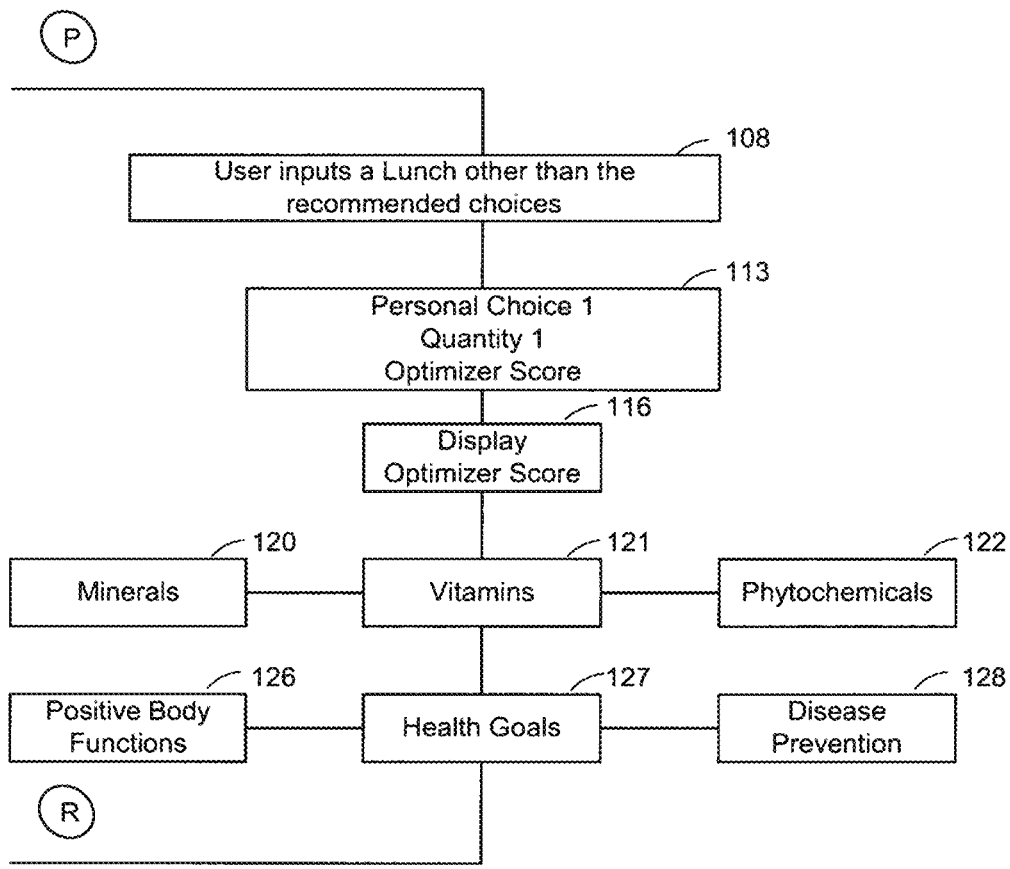
FIG. 1H includes the user's ability to input a food choice other than what is suggested for lunch.
Figure 1J:
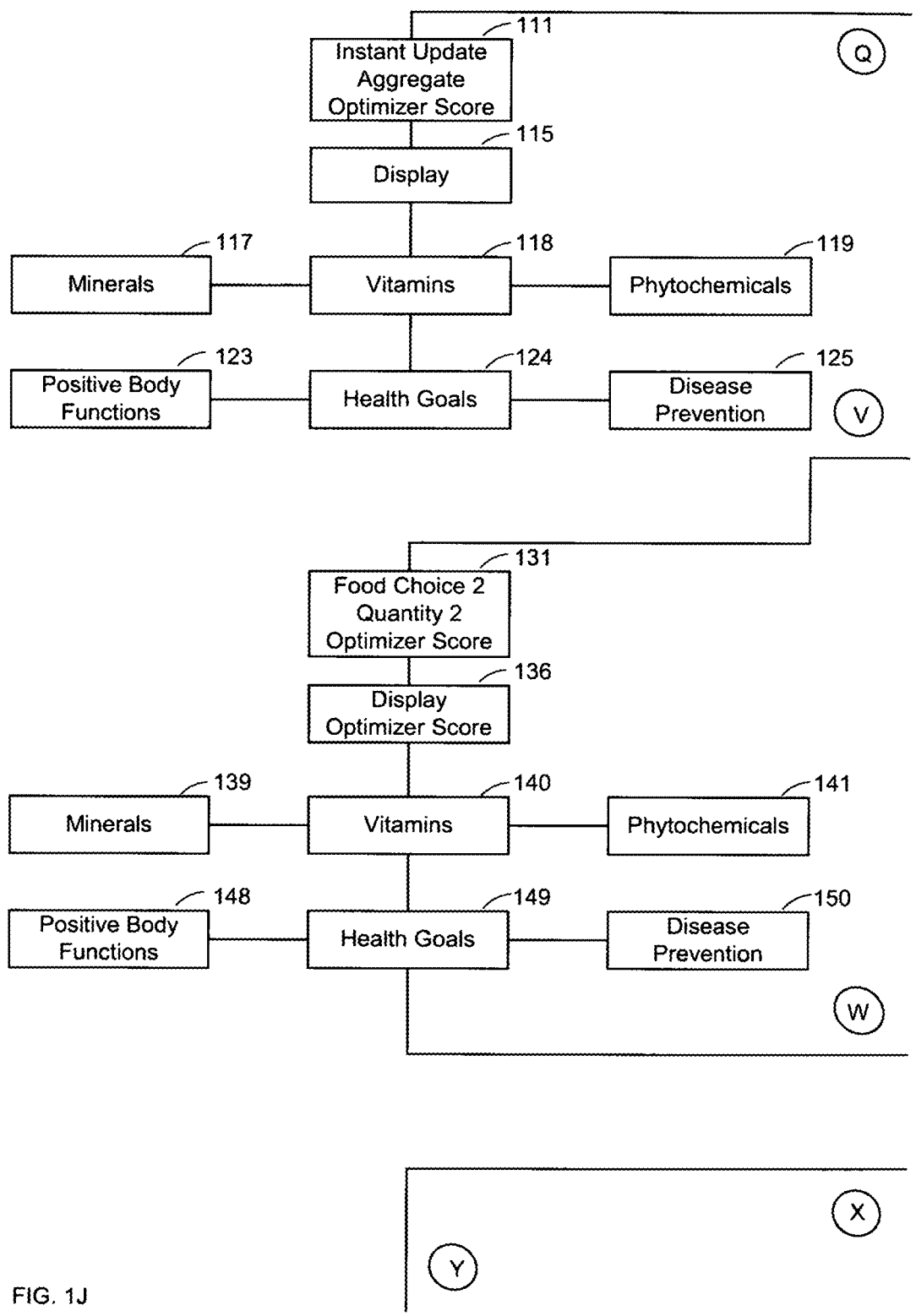
FIG. 1J includes the instant update aggregate optimizer score after lunch and food choice 2 for dinner.
Figure 1K:
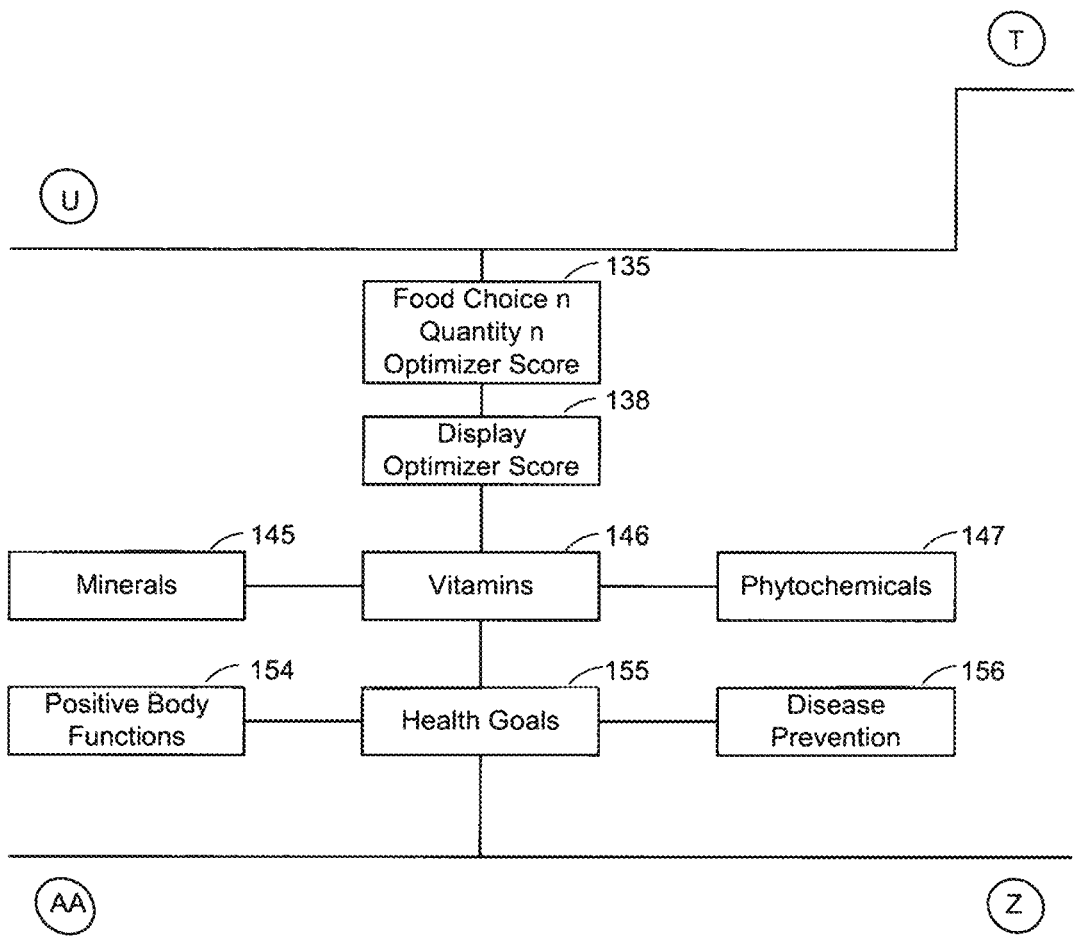
FIG. 1K includes food choice n for dinner.
Figure 1L:
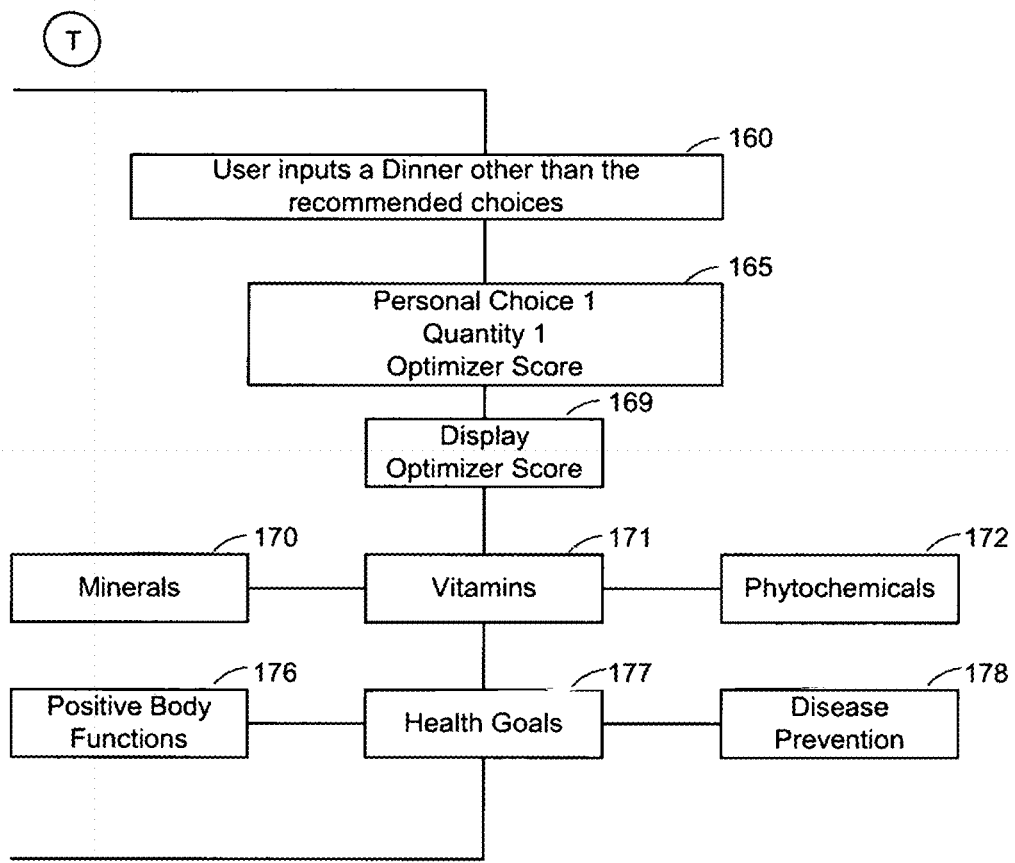
FIG. 1L includes the user's ability to input a food choice other than what is suggested for dinner.
Figure 1M:
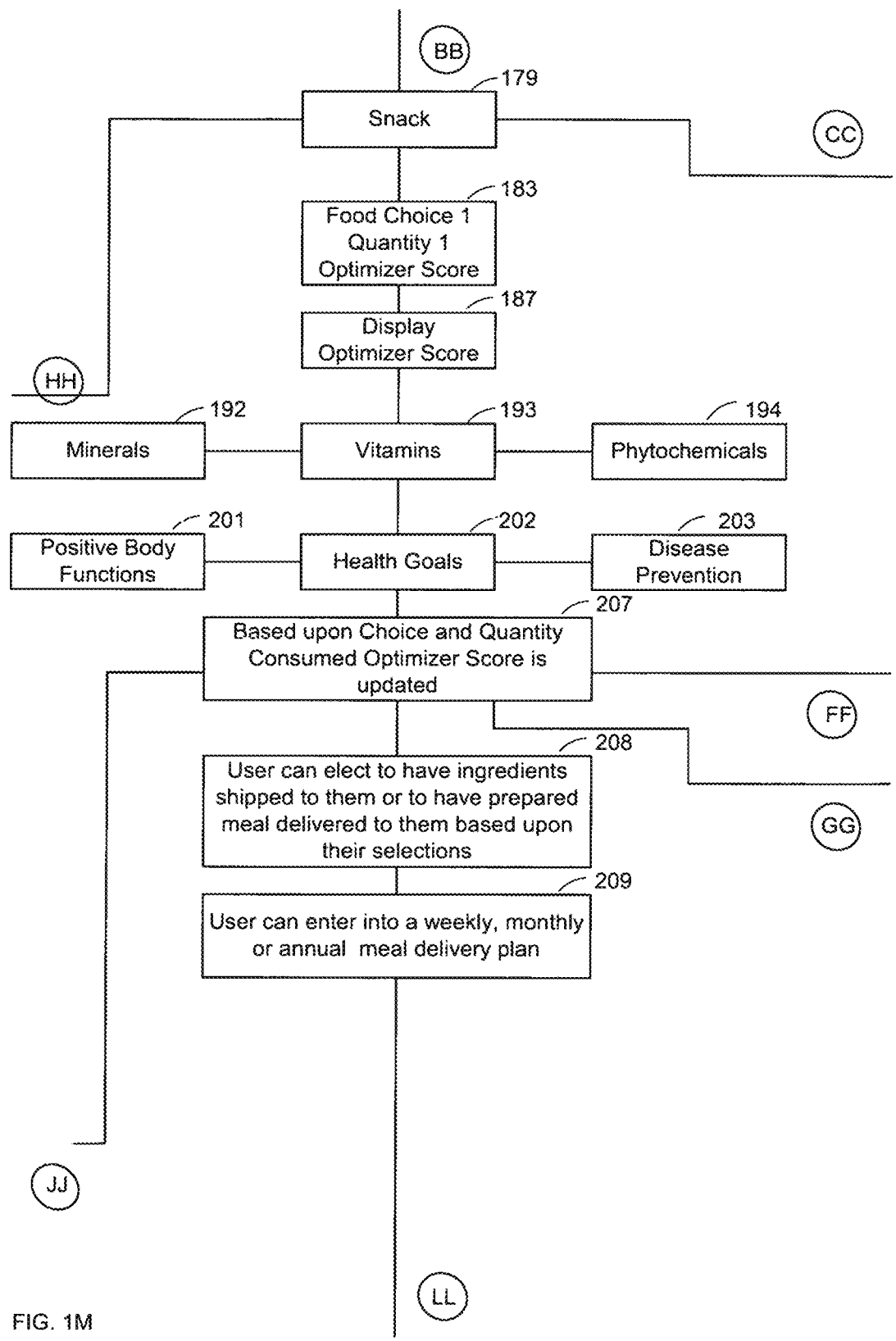
FIG. 1M includes the snack display and the option to have food shipped to the user.
Figure 1N:
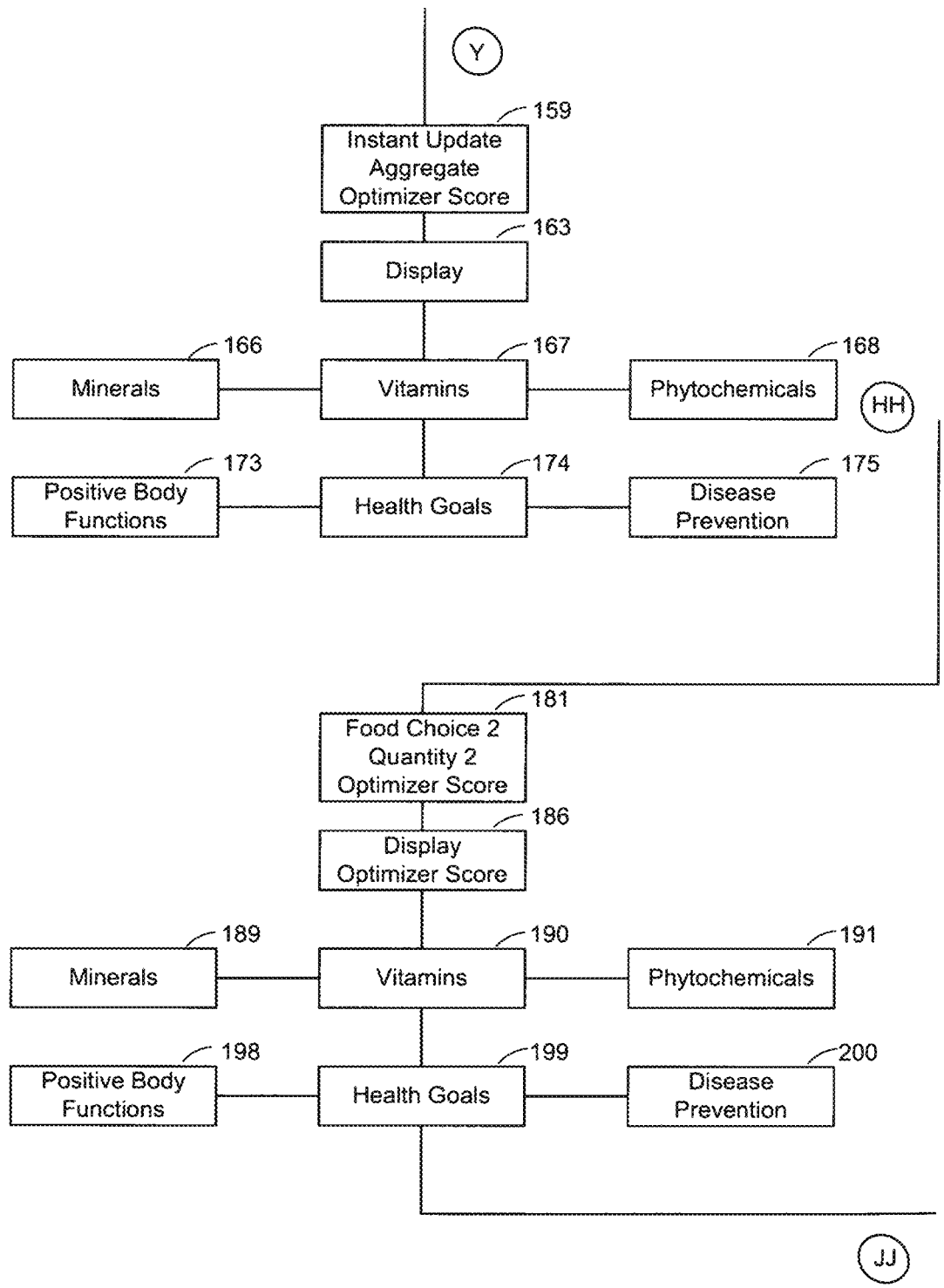
FIG. 1N includes the instant update aggregate optimizer score after dinner and food choice 2 for snack.
Figure 1P:
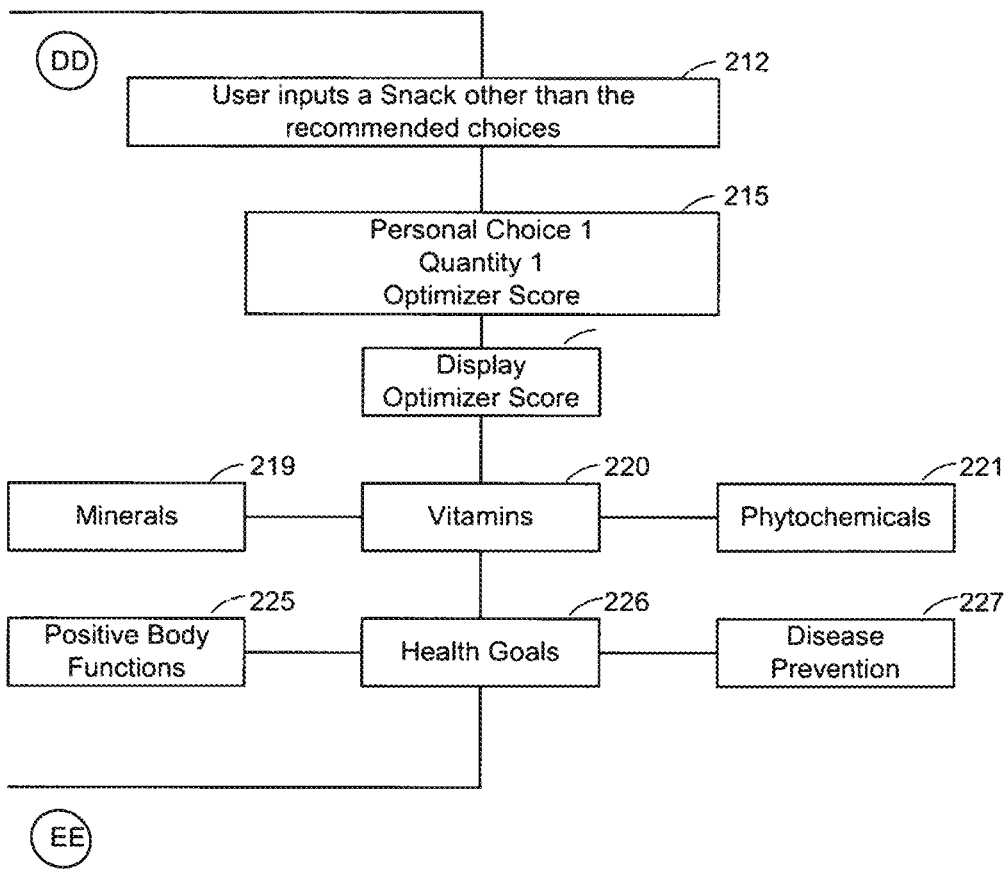
FIG. 1P includes the user's ability to input a food choice other than what is suggested for snack.
Figure 1Q:
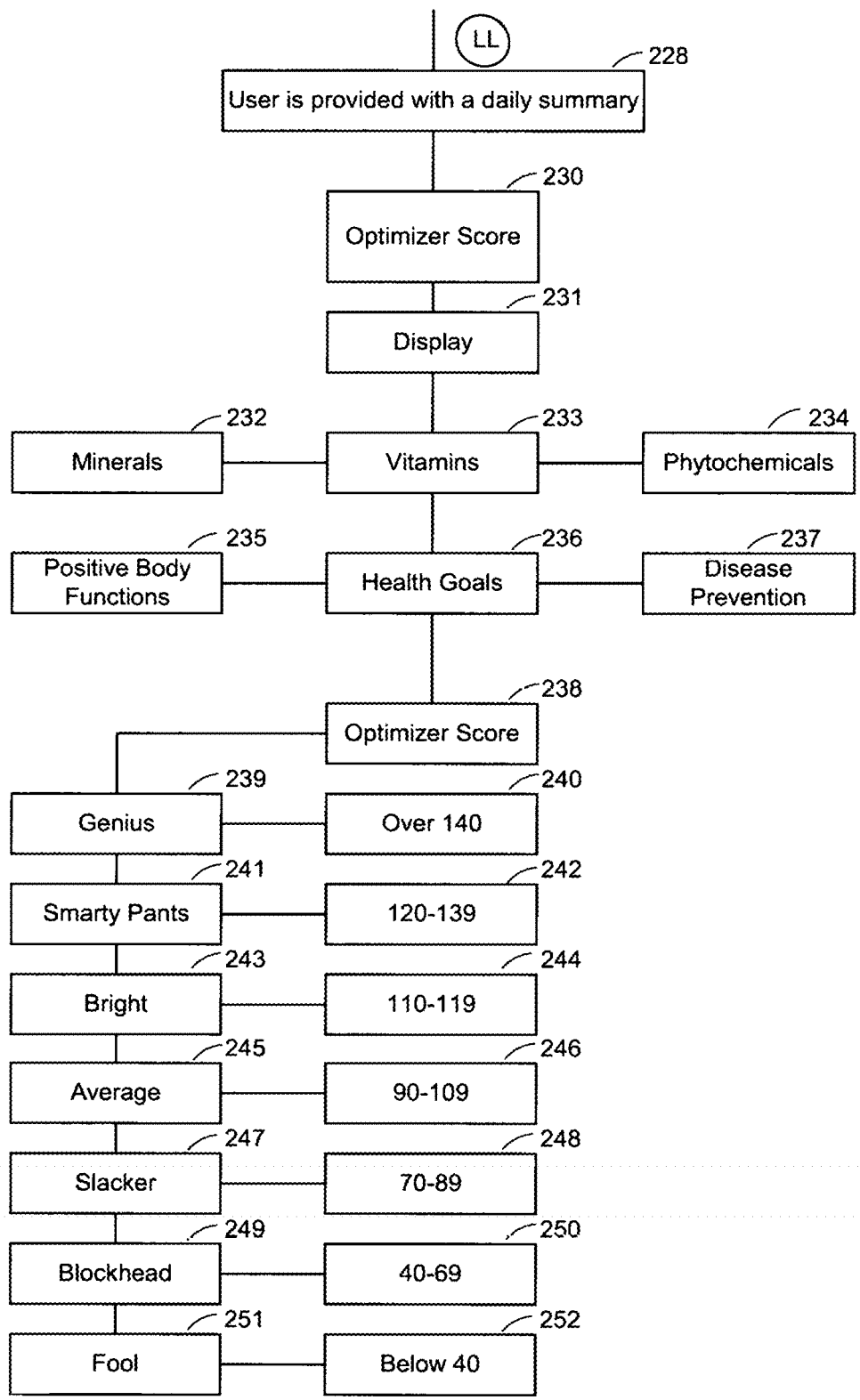

In FIGS. 1A-Q the flow chart describing the overall use of the software application is delineated. A user is presented with a welcome screen 7 and is then asked to select from a variety of health goals from a drop-down menu 8:

10 Healthy Vision
11 Build Muscle
12 More Energy
13 Healthy Immune System
14 Hair Growth
15 Healthy Skin
16 Healthy Nails
17 Heart Healthy
18 Weight Loss
19 Manage Blood Pressure
20 Manage Cholesterol
21 Mental Sharpness
22 PH Level
23 Cancer Fighters
24 Anti Inflammatory
25 Healthy Bones & Fight Osteoporosis
26 Enhance Metabolism
27 Fight type 2 Diabetes Once a user selects various health goals, the algorithm accesses a database of known foods related to improving one's health as it pertains to the selected health goals as well as providing the body with the essential nutrients it requires. The user may be given an option to enter various laboratory information such as their blood and urine work results 9. Some sample questions asked regarding the laboratory information are:

Sodium level
Potassium level
Glucose Level
Total Protein
Calcium, Serum level
Triglyceride Level
Cholesterol Level
HDL Cholesterol level
LDL Cholesterol level
PSA level
TSH level
PH level
Vitamin D level
CRP Based upon the answers to the questions about the laboratory information, the algorithm may access the database of known foods and make selections that can help improve a rating score which in the preferred embodiment may be referenced as an optimizer score.

The present invention includes a proprietary algorithm that accesses a data base of foods, their mineral, vitamin, phytochemical content; their positive health effects on the body; their disease prevention capabilities and the body's required nutrients to Optimize the human body's health. This data is analyzed and incorporated into the algorithm to generate an Optimizer Score for each food. The algorithm is written such that the Optimum daily score is 140 or greater. By achieving an Optimizer Score of 140 or greater, a user has provided the human body with all the essential nutrients that it requires; the user has not exceeded the recommended amounts of foods; the user has avoided foods that are detrimental to human health and the user has selected foods that will help them achieve their health goals.

The user may then prompted to select from a variety of foods for breakfast 29. The foods offered as options to select from 31, 33, 35 (there are more than 3 options offered, option 35 has an "n" written in to represent more options) are derived by the algorithm based upon the health goals selected, the nutritional value of the foods, the body's required minerals, vitamins, and phytochemicals and the disease prevention qualities of the food: Each food offered as an option may have its Minerals 39, 42, 45, Vitamins 40, 43, 46, Phytochemicals 41, 44, 47, Positive Body Function 48, 51, 54, Health Goals 49, 52, 55, Disease Prevention qualities 50, 53, 56 displayed as 36, 37, 38 for the user to review. The Optimizer Score for each food offered may also be displayed as 36,37, 38, based upon quantities entered. Based upon the foods selected and the quantities consumed the Aggregate Optimizer Score may be updated 57, 59.

The user may have the option to enter a food not offered by the algorithm into the application 60 and view its Optimizer Score 69, after entering the quantity, and resulting Minerals 73, Vitamins 74, Phytochemicals 75, Positive Body Function 76, Health Goals 77, Disease Prevention 78 qualities, displayed 69.

Users may have helpful reminders displayed regarding eating habits that are not consistent with the recommended foods, based upon their health goals, laboratory information and overall human body essential nutrient requirements. For example, if a user has a habit of entering red meat as food consumed, but not suggested by the algorithm, they may get a reminder that consuming too much red meat may be contributing to their high cholesterol level.

The user may be offered an option to have the ingredients of their selected breakfast or a prepared meal, from the ingredients selected, delivered to their destination of choice 61. The user may have the option to enter into a weekly, monthly or annual meal delivery plan 65.

After the consumed quantity and specific breakfast food information is entered into the algorithm, the Aggregate Optimizer Score may be updated 59. Also, the aggregate of foods and quantities of foods consumed in that 24-hour period, starting at 12 AM, may have their health data displayed as: Minerals 66, Vitamins 67, Phytochemical 68, Positive Body Functions 70, Health Goals 71 and Disease Prevention 72.

This above process may be repeated for Lunch, Dinner and Snacks 79-227. The algorithm may determine what foods and quantities should be consumed for the balance of the day based upon what has already been consumed; the balance of essential minerals, vitamins, phytochemicals and nutrients that the body requires; the balance of food required to meet the user's health goals; the balance of food required to meet the related Positive Body Function; the balance of foods required to meet the Disease Prevention targets; and the food required to maintain a healthy body PH. The user's Optimize Score may be penalized for exceeded the recommended daily caloric intake, exceeding the daily LDL Cholesterol limit, exceeding the daily Sodium level and exceeding the daily sugar limit.

The Optimizer Score may based upon achieving 100% of the daily required amount of the following categories on a daily basis:

Minerals
Vitamins
Phytochemicals

The Optimizer Score may be based upon achieving 100% of the daily required level of the following categories on a daily basis:
Health Goals
Positive Body Function
Disease Prevention
PH There may also be a negative effect on your Optimizer score for the following categories:
Exceeding the recommended daily Calorie limit
Exceeding the daily LDL Cholesterol limit
Exceeding the daily Sodium (salt) limit
Exceeding the daily Sugar limit $$\text{Optimizer Score} = (\% \text{ daily Minerals Level} \times 20) + (\% \text{ daily Vitamins Level} \times 20) + (\% \text{ daily Phytochemicals Level} \times 20) + (\% \text{ daily Health Goals Level} \times 20) + (\% \text{ daily Positive Body Functions Level} \times 20) + (\% \text{ daily Disease Prevention Level} \times 20) + (\% \text{ daily PH Level} \times 20) - [(\% \text{ over daily recommended calorie intake} \times 10) + (\% \text{ over daily limit for salt} \times 10) + (\% \text{ over daily limit for LDL cholesterol} \times 10) + (\% \text{ over daily limit for sugar} \times 10)]$$

$$OS = (\% \text{ DRA}(M) \times 20) + (\% \text{ DRA}(V) \times 20) + (\% \text{ DRA}(P) \times 20) + (\% \text{ DRL}(PBF) \times 20) + (\% \text{ DRL}(HG) \times 20) + (\% \text{ DRL}(DP) \times 20) + (\% \text{ DRL}(PH) \times 20) - [(\% \text{ over DL}(C) \times 10) + (\% \text{ over DL}(SA) \times 10) + (\% \text{ over DL}(LDL) \times 10) + (\% \text{ over DL}(SU) \times 10)]$$

Figure 6A:
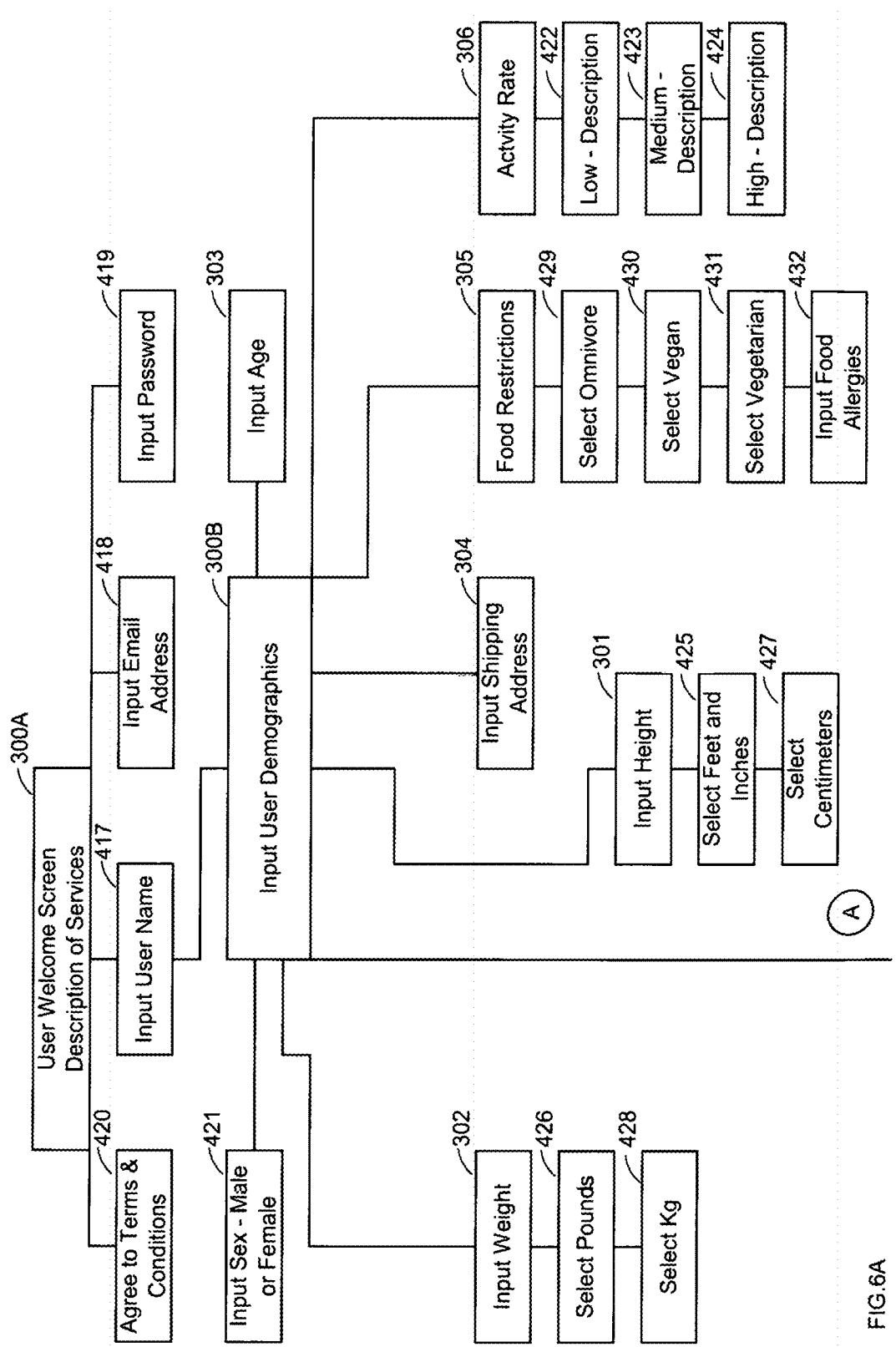
FIGS. 6A-G are components of a flow chart that depicts how the user would make selections from the various health goals displayed.
Figure 6B:
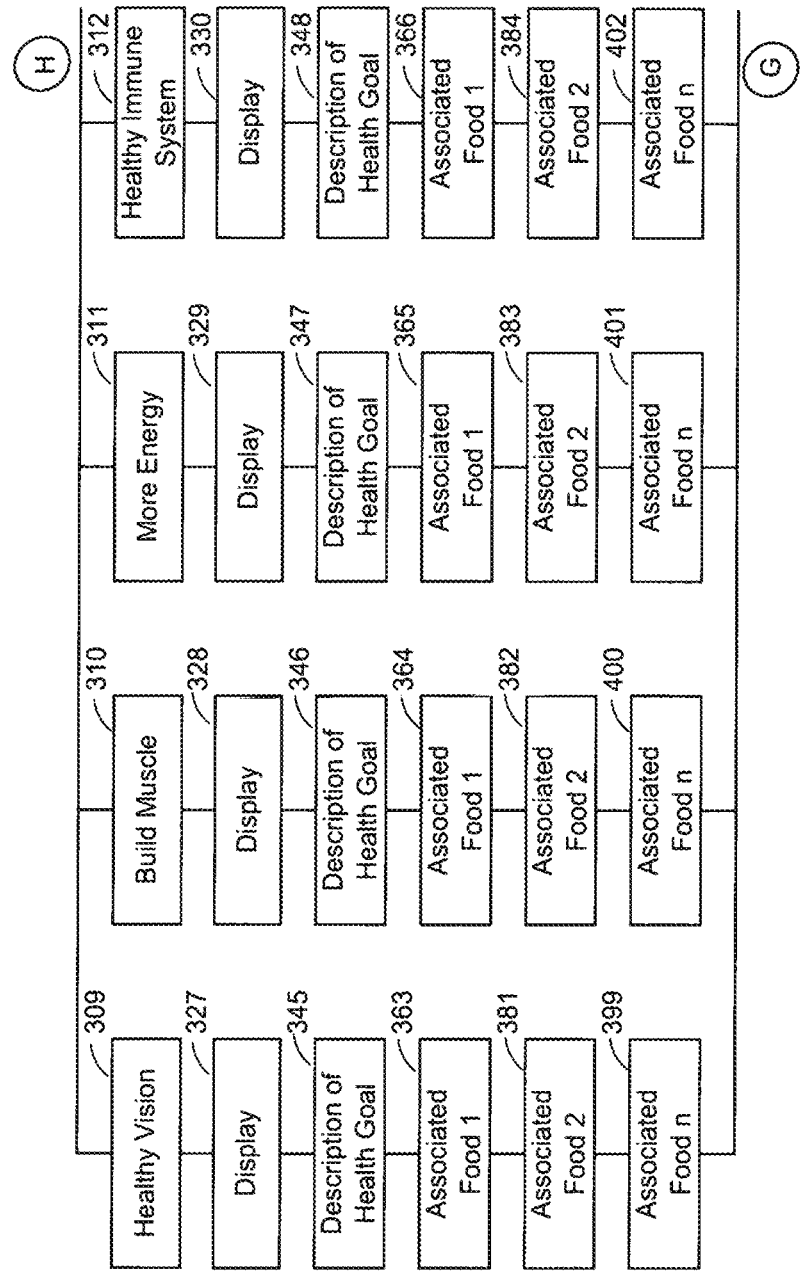
Figure 6C:
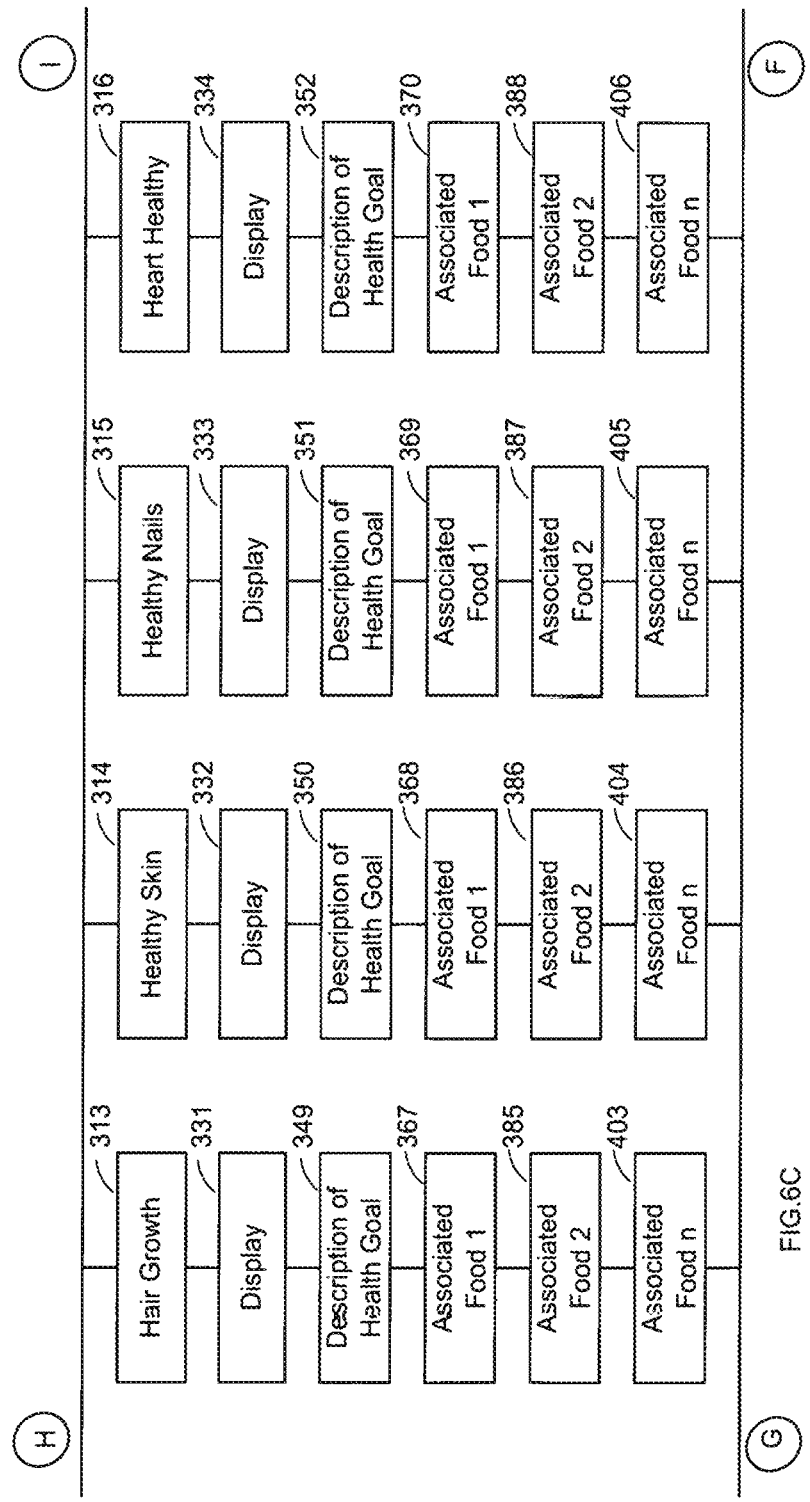
Figure 6D:
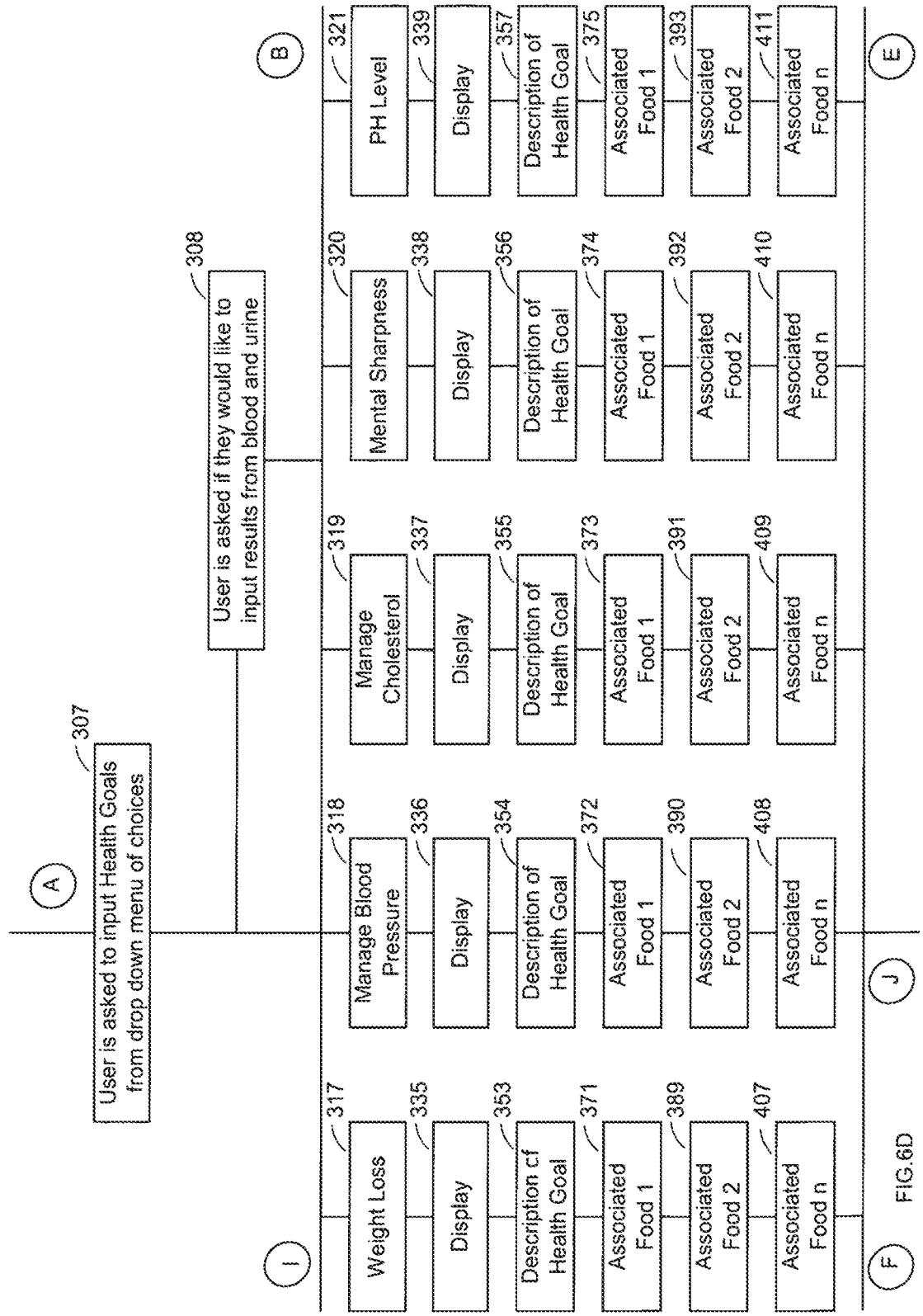
Figure 6E:
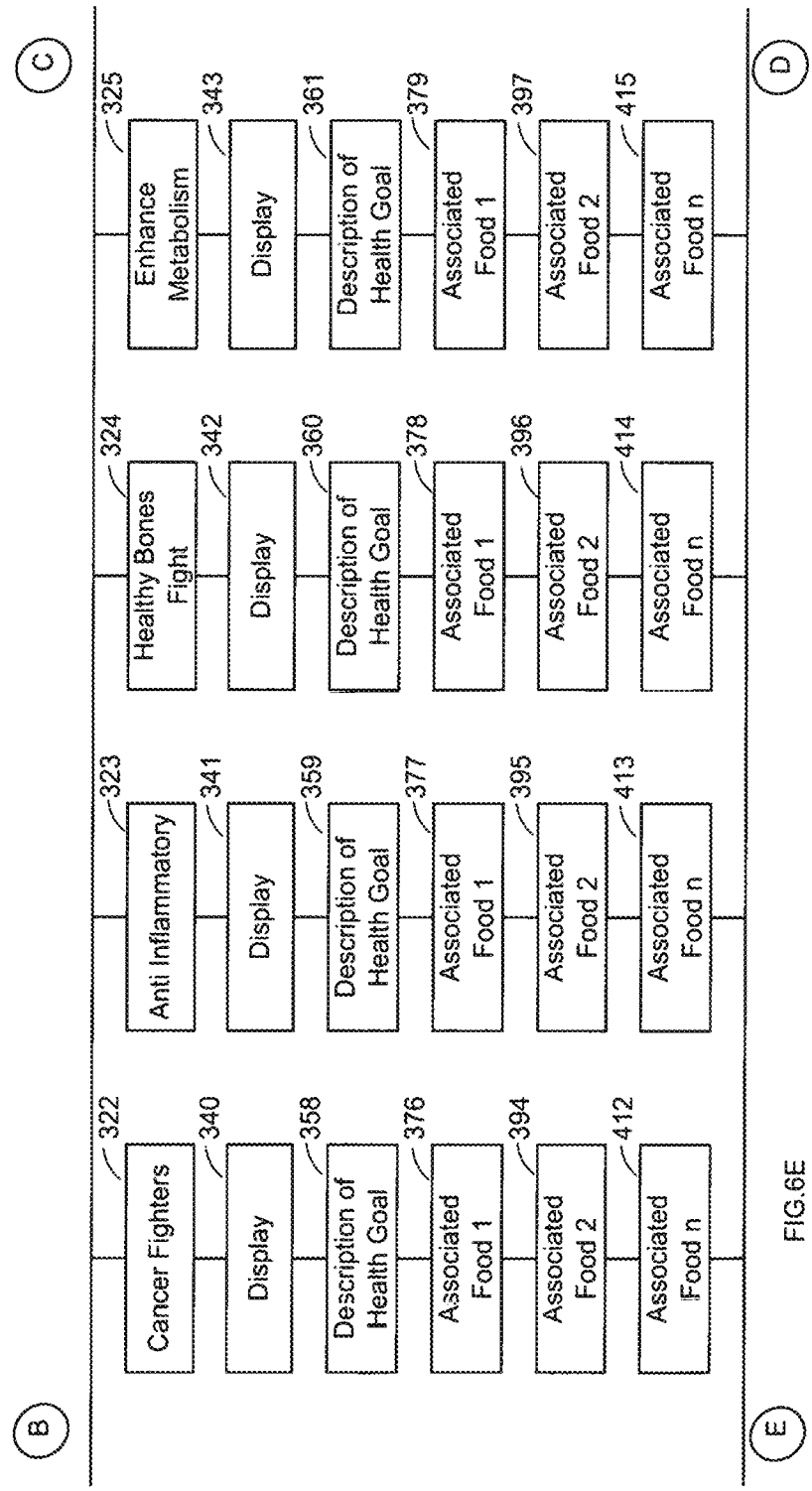
Figure 6F:
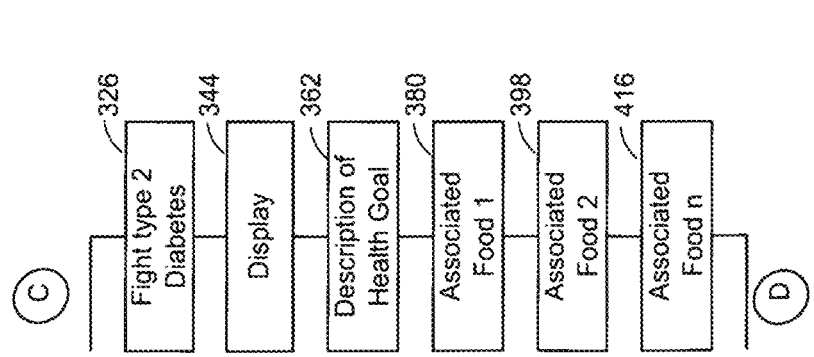
Figure 6G:
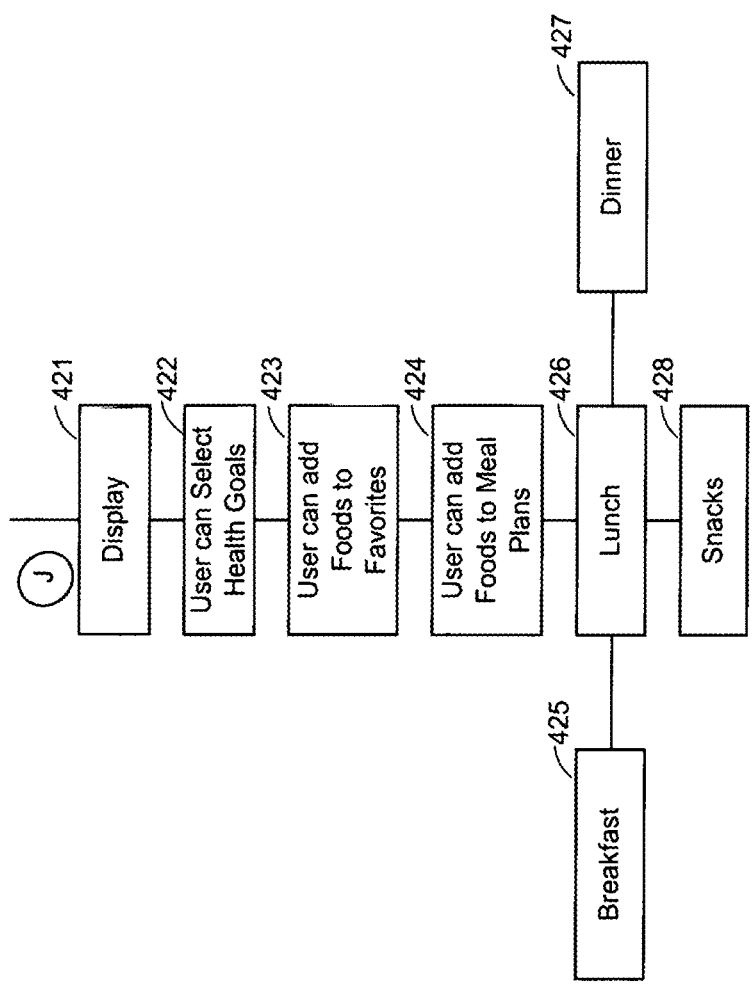
Figure 7A:
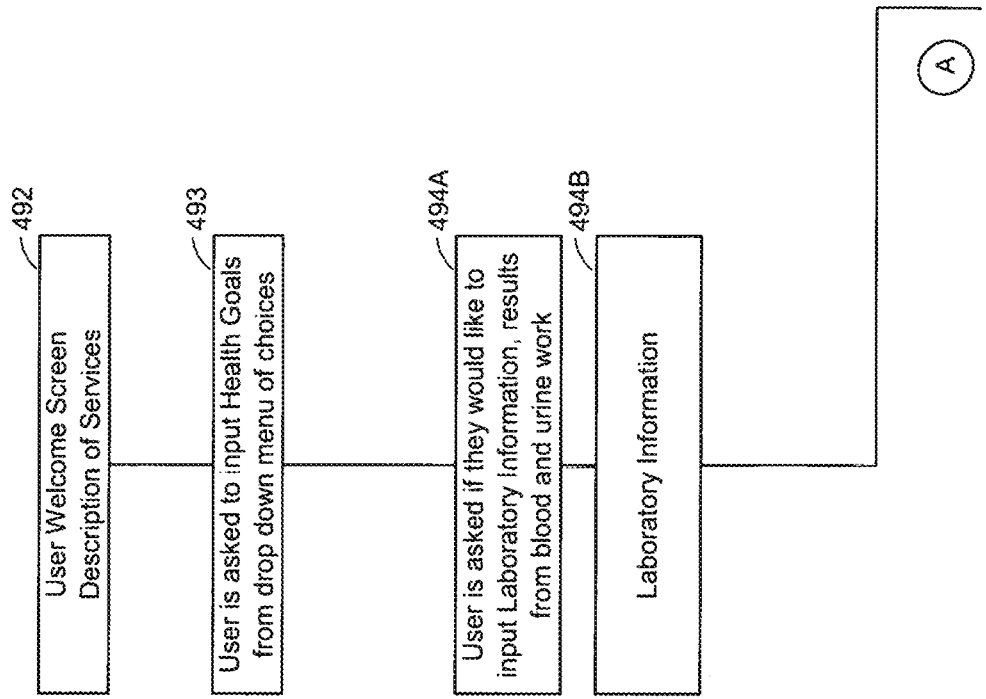
FIGS. 7A-F are components of a flow chart that shows how the user can enter Laboratory Information from their blood and urine work in order to better determine the required health goals, body function and disease prevention.
Figure 7B:
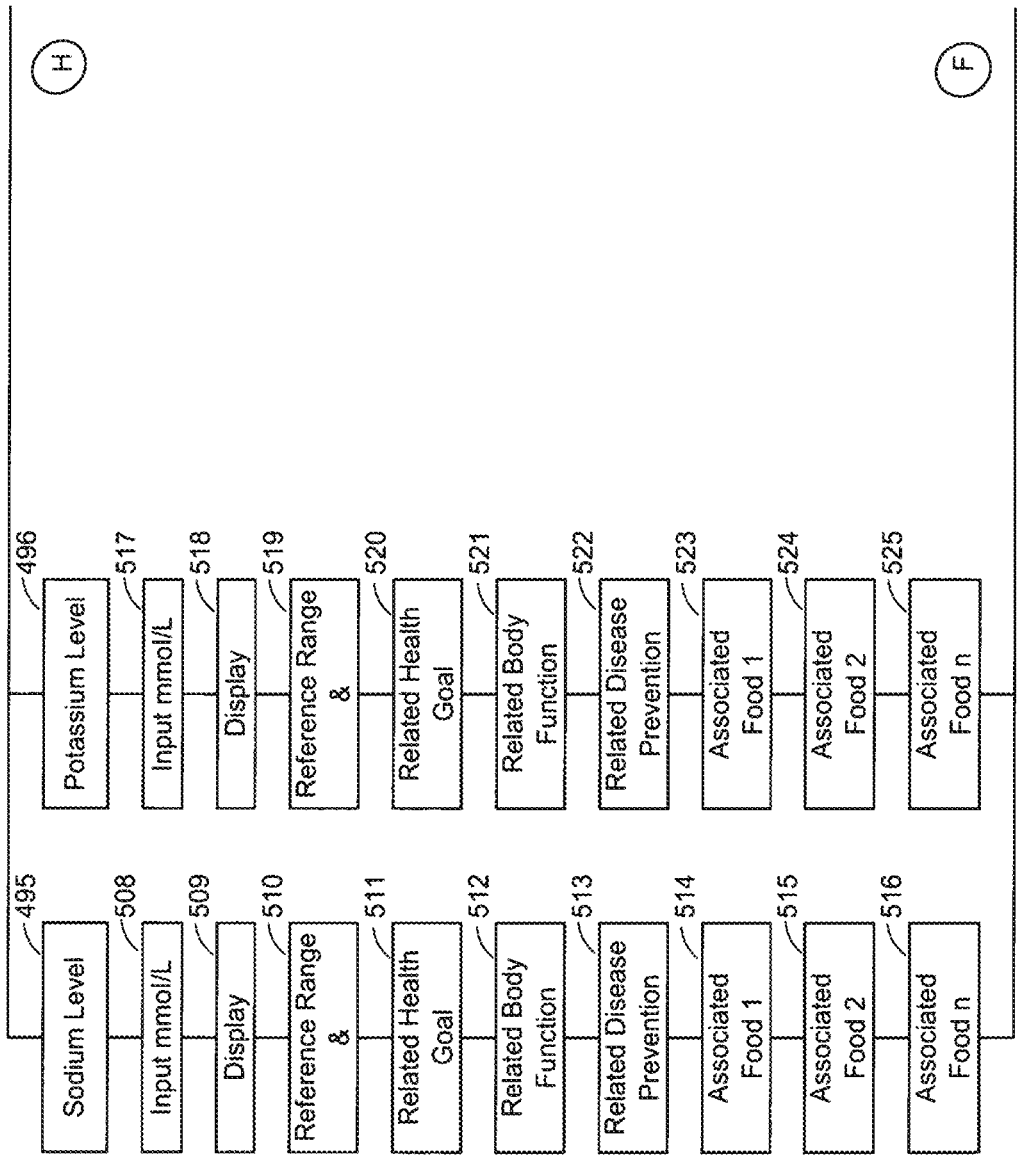
Figure 7C:
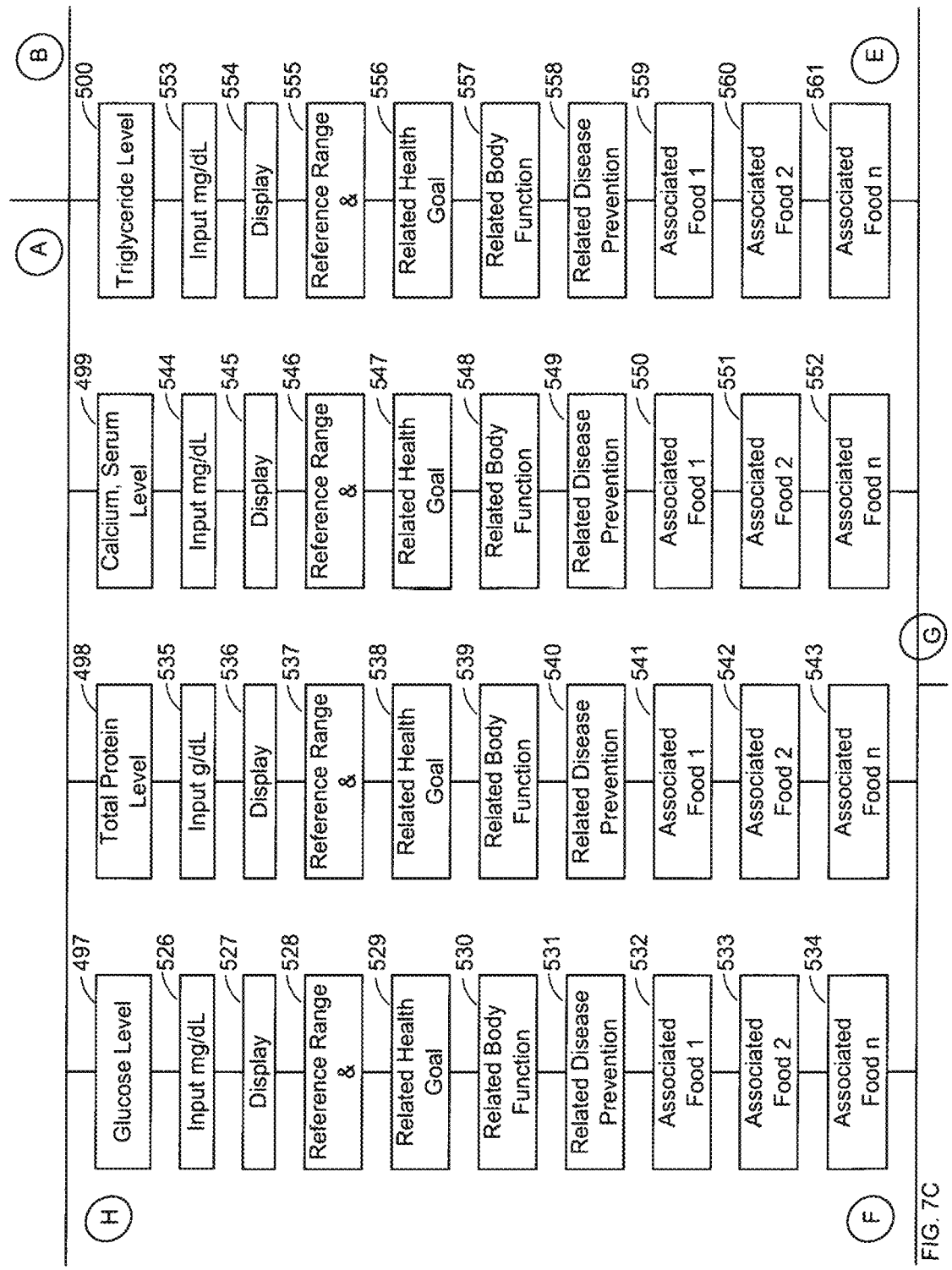
Figure 7D:
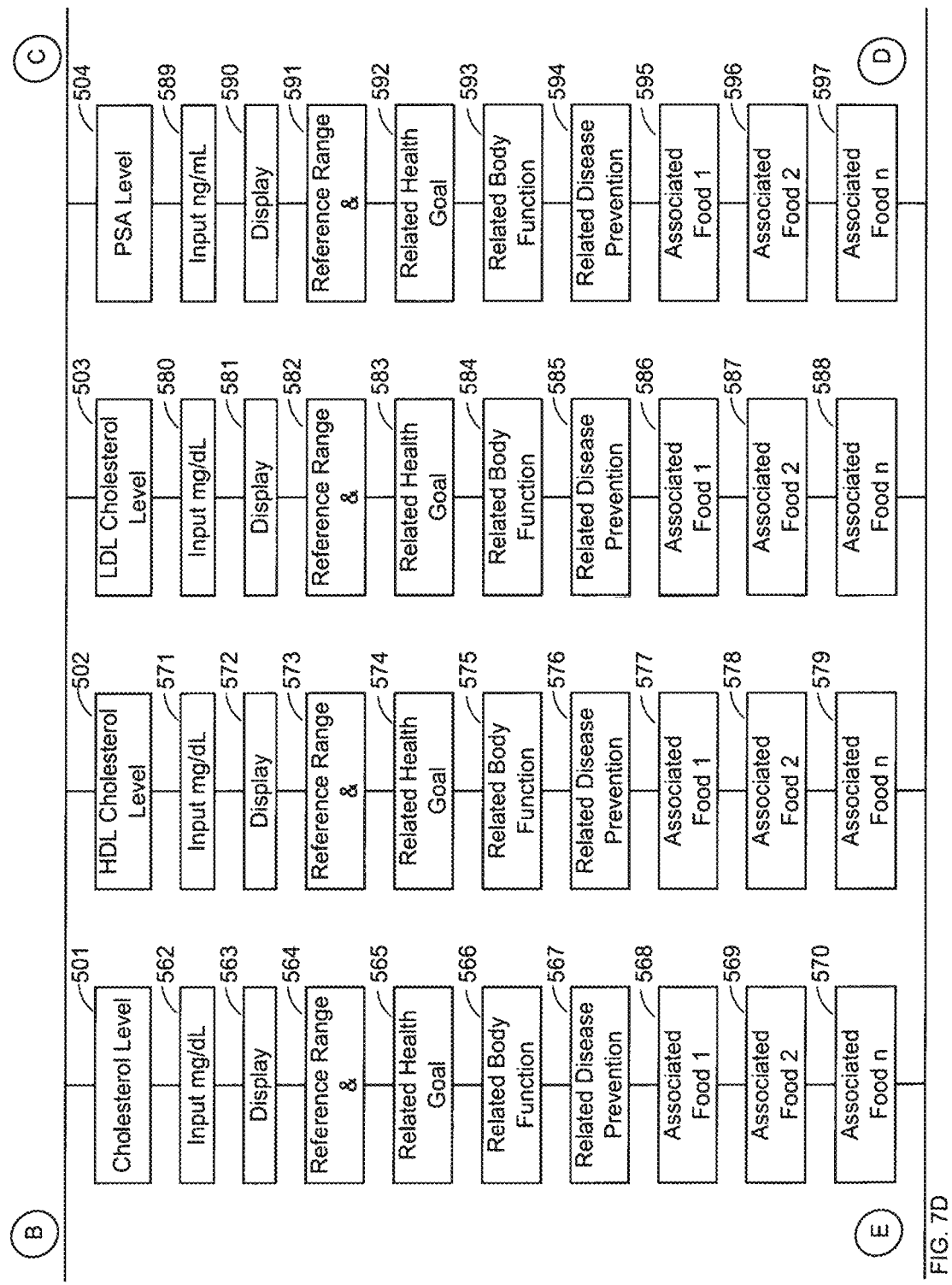
Figure 7E:
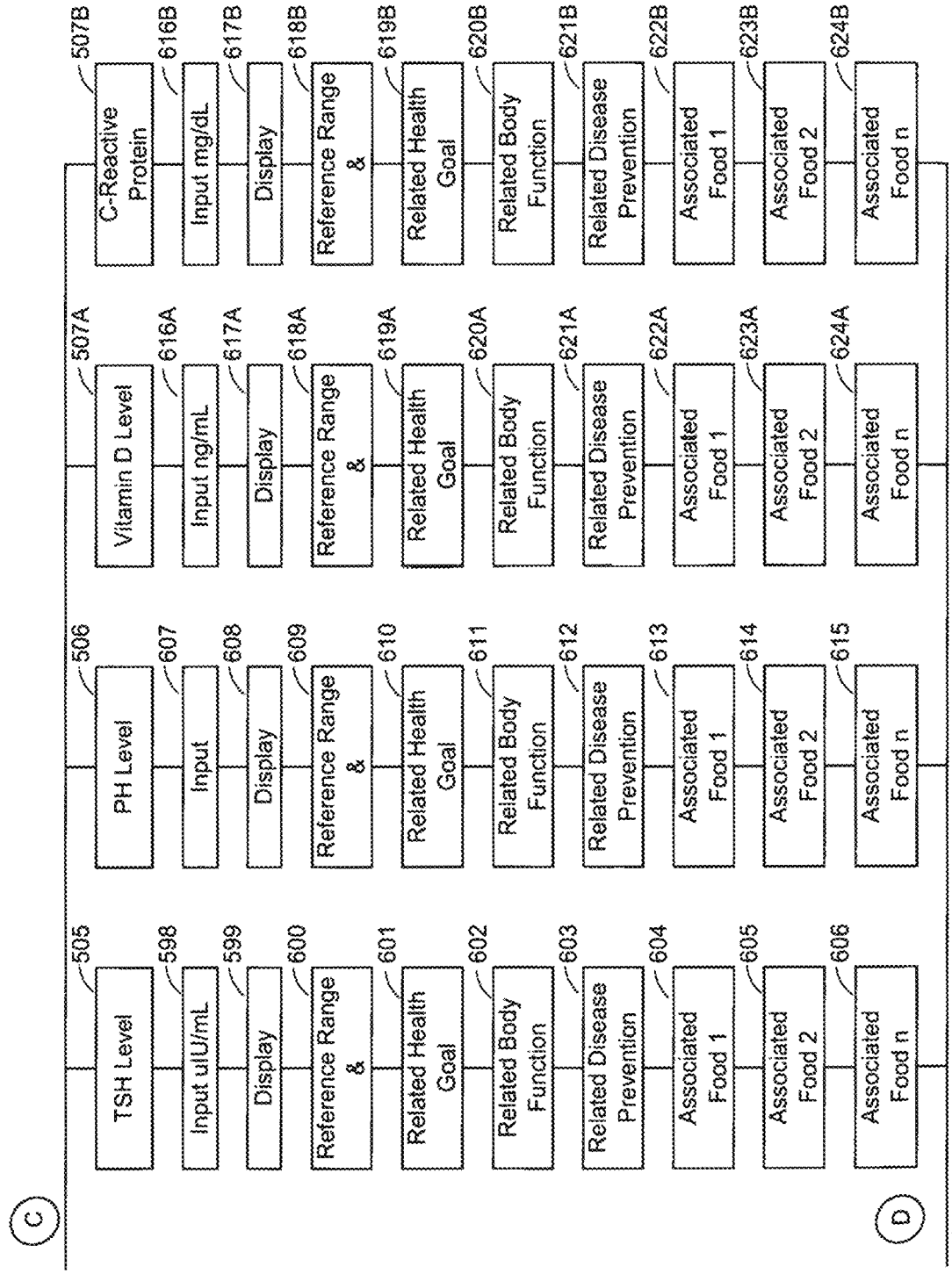
Figure 7F:
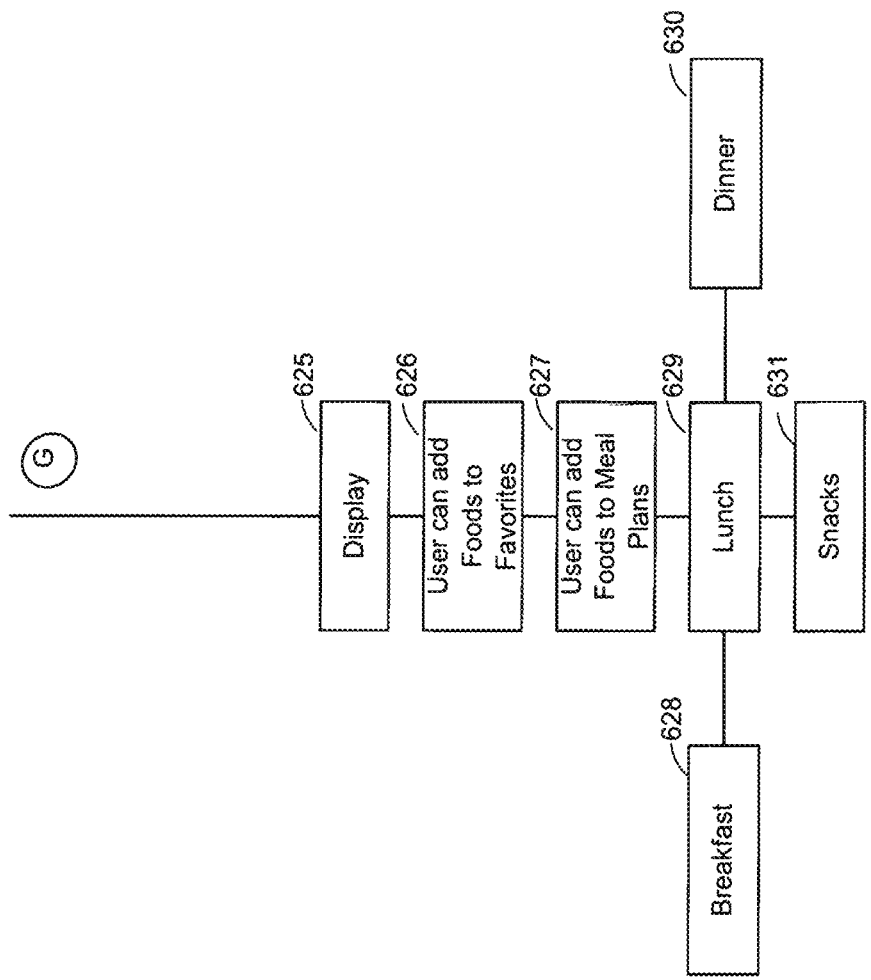
Figure 8A:
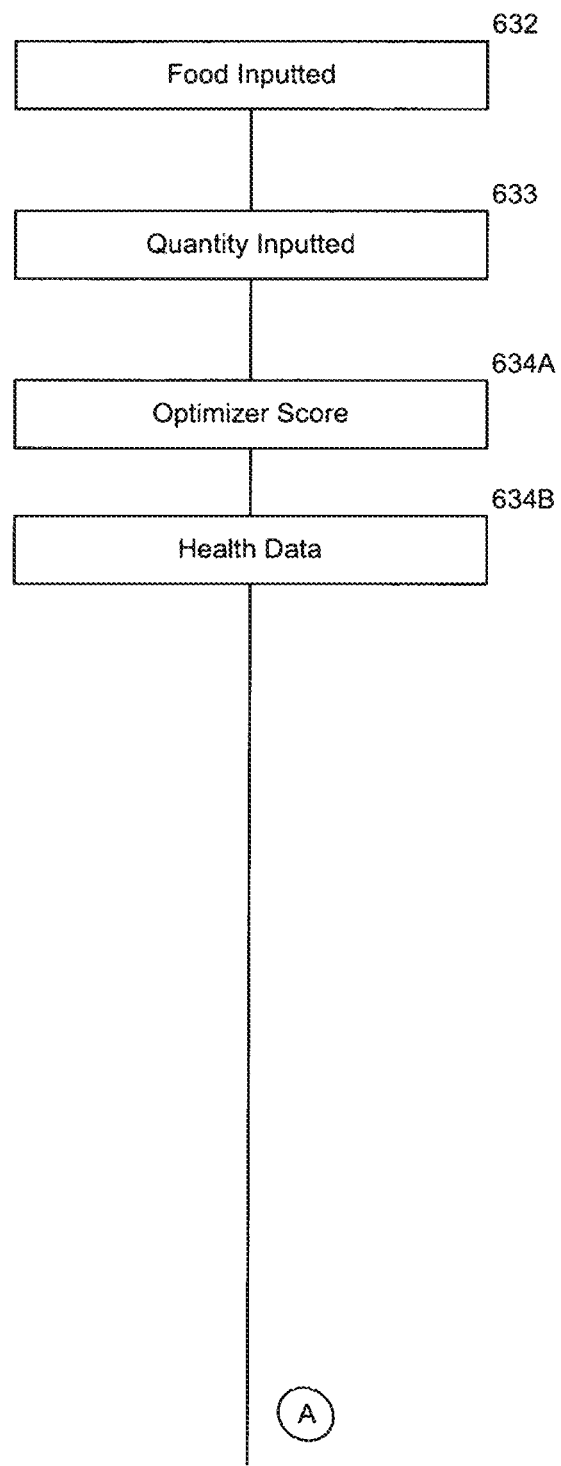
FIGS. 8A-G are components of a flow chart that depicts the detailed data that can be reviewed by the user for specific foods that are inputted: Minerals, Vitamins, Phytochemicals, Positive Body Functions, Health Goals and Disease Prevention.
Figure 8B:
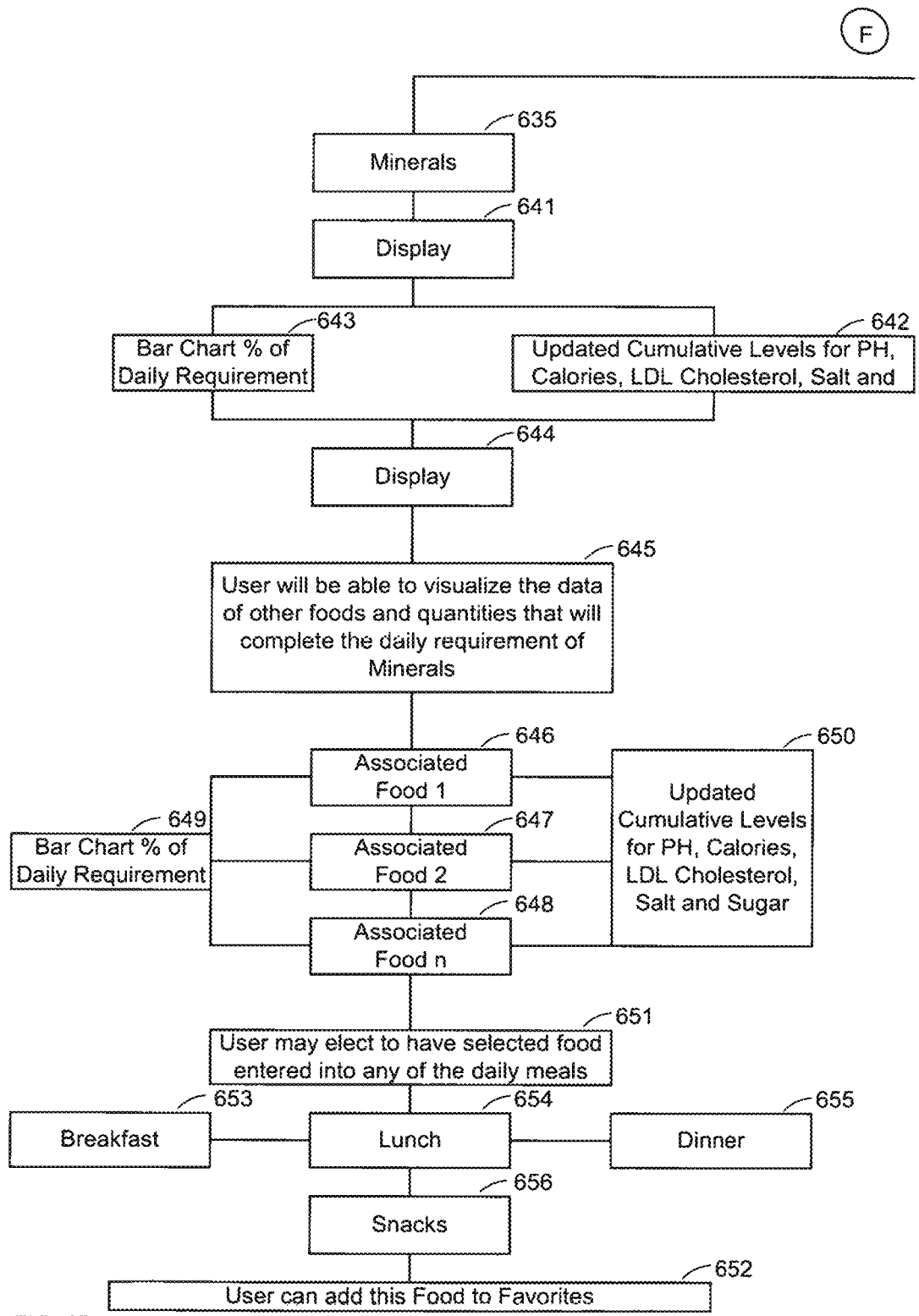
Figure 8C:
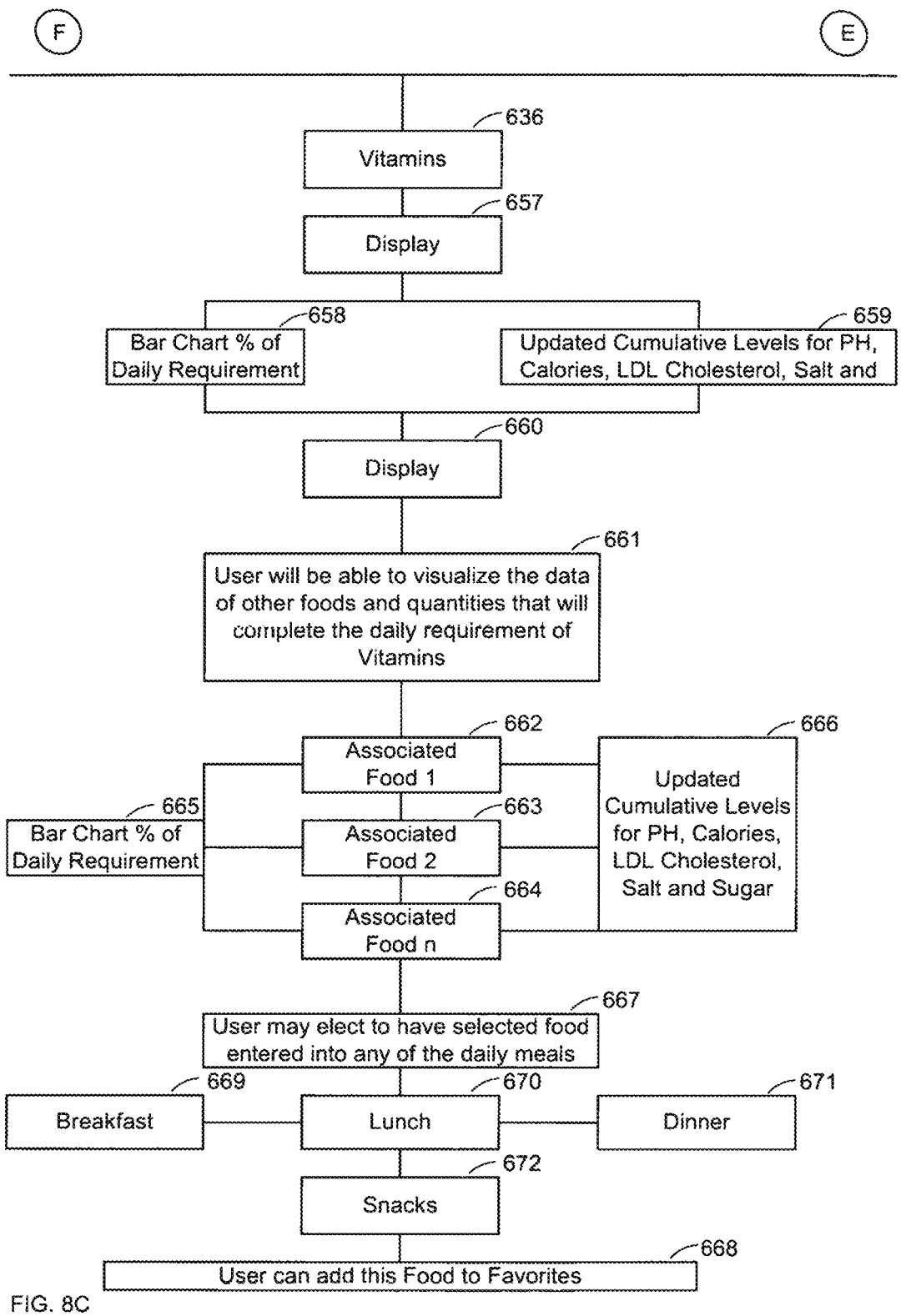
Figure 8D:
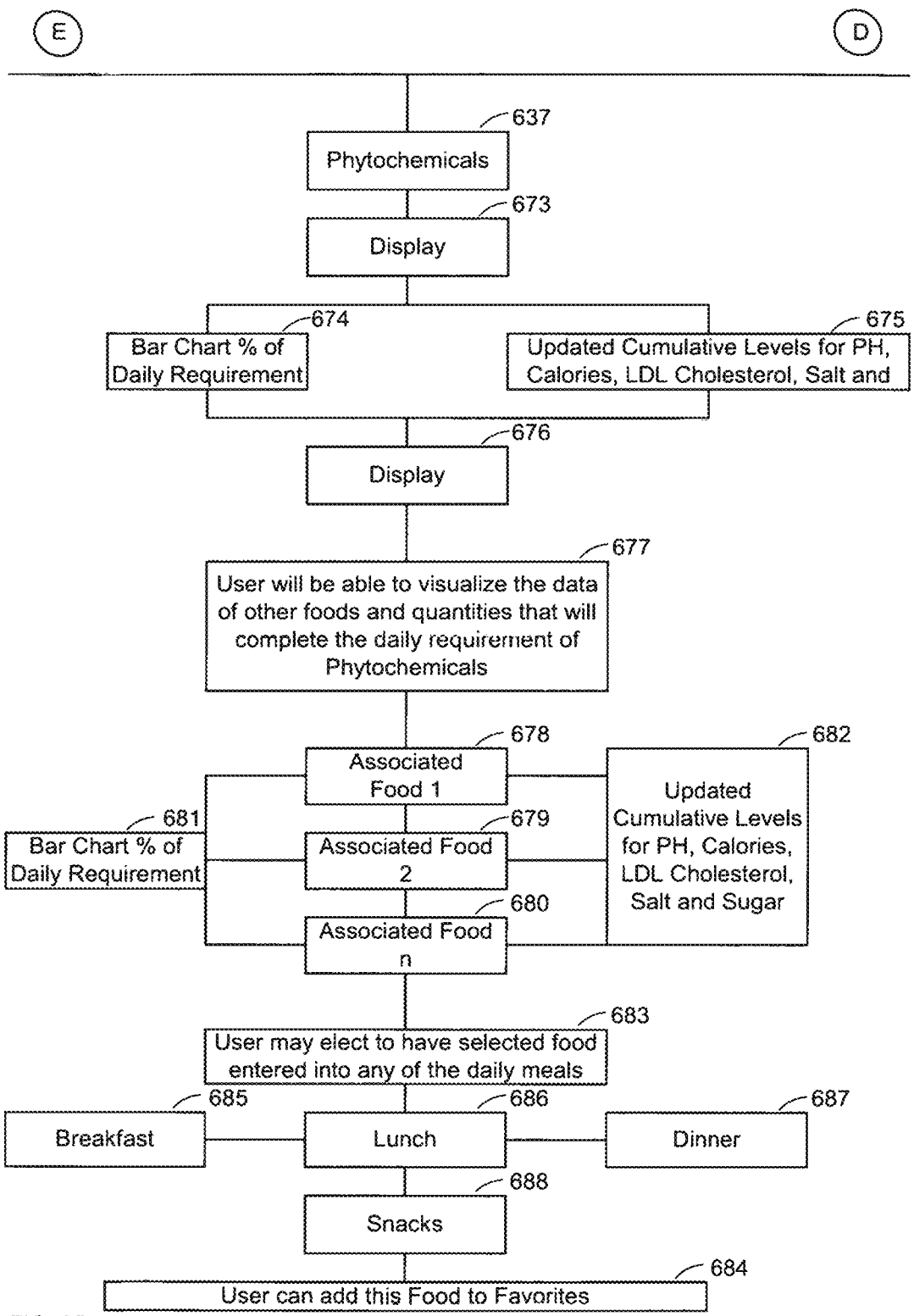
Figure 8E:
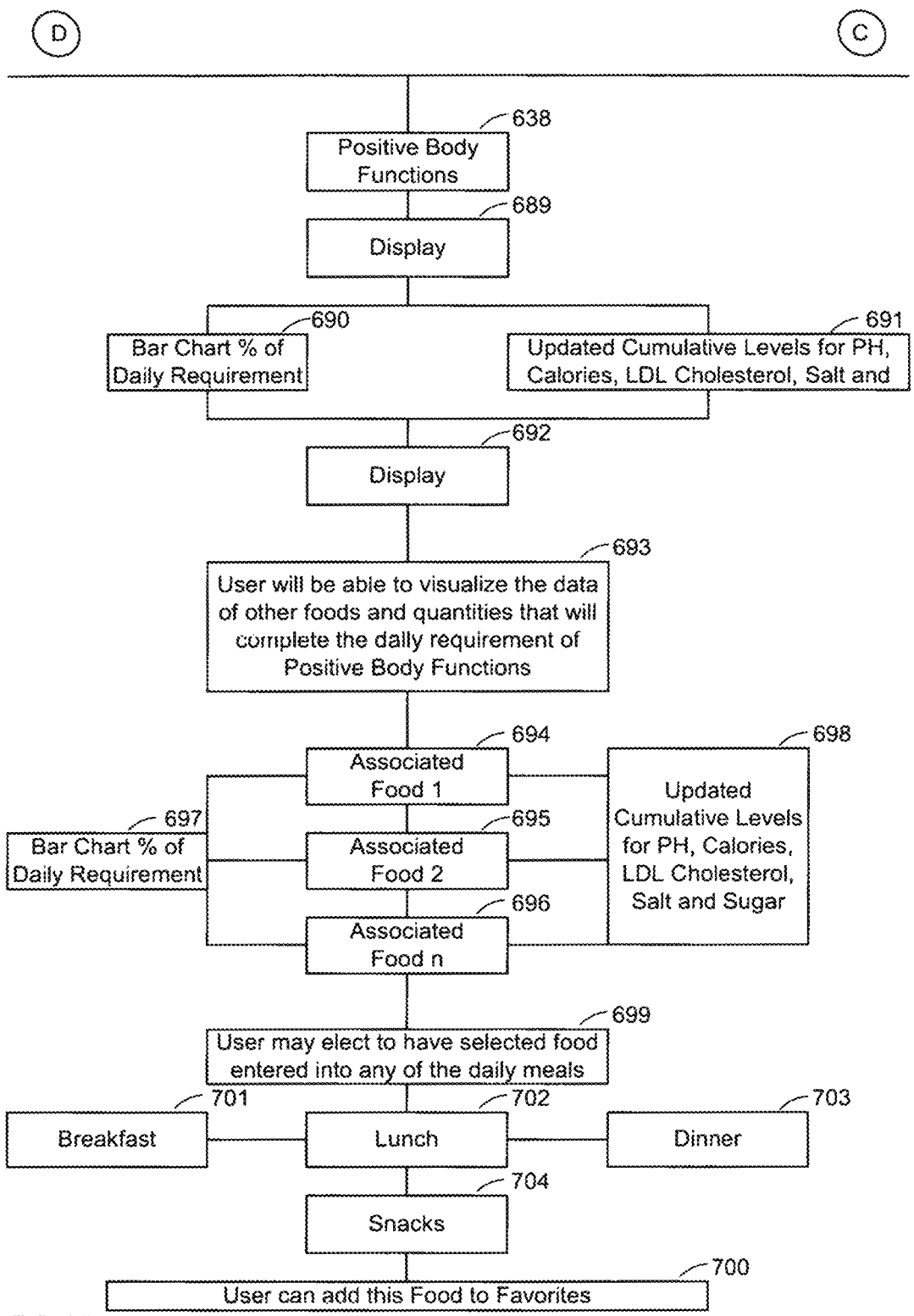
Figure 8F:
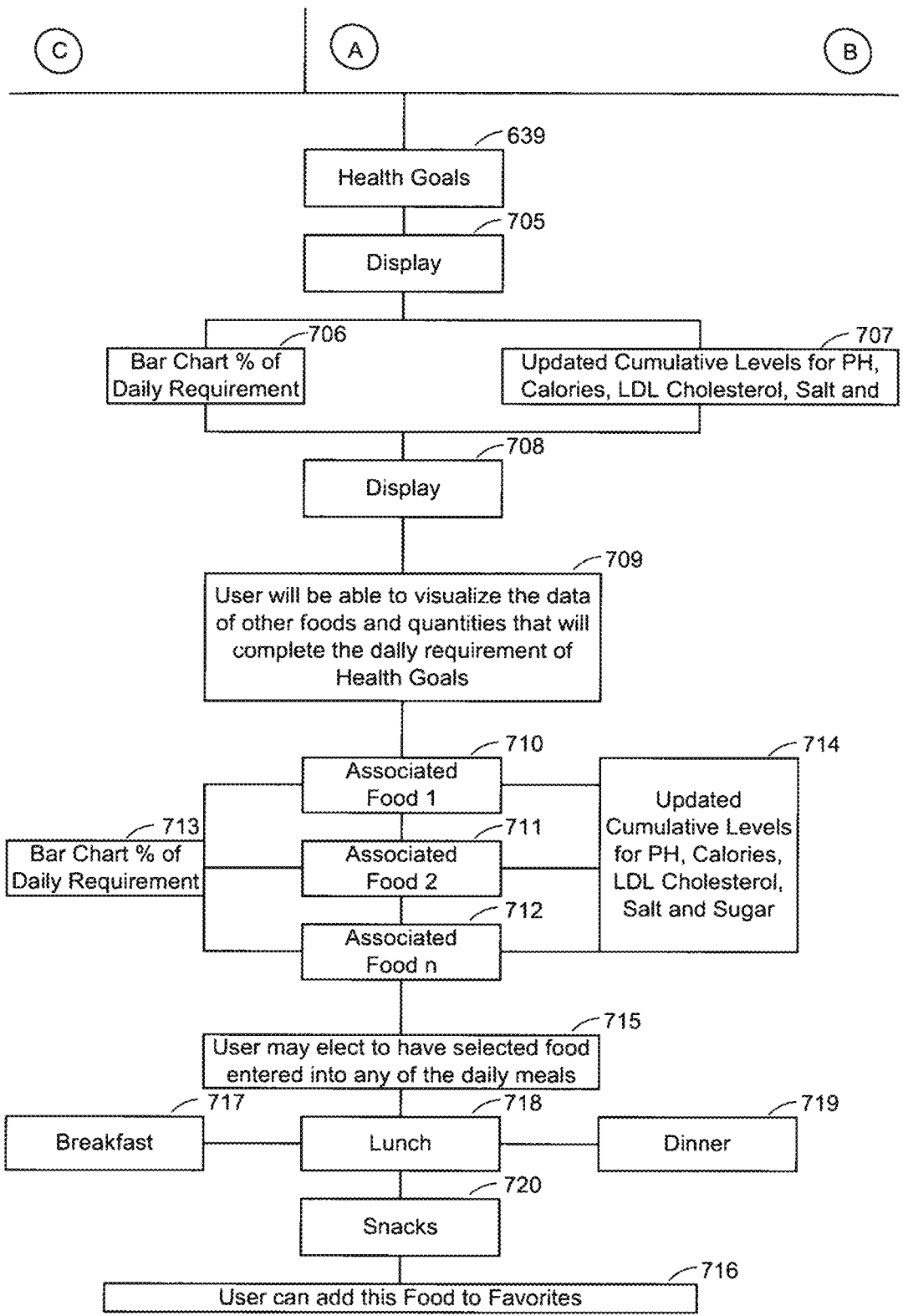
Figure 8G:
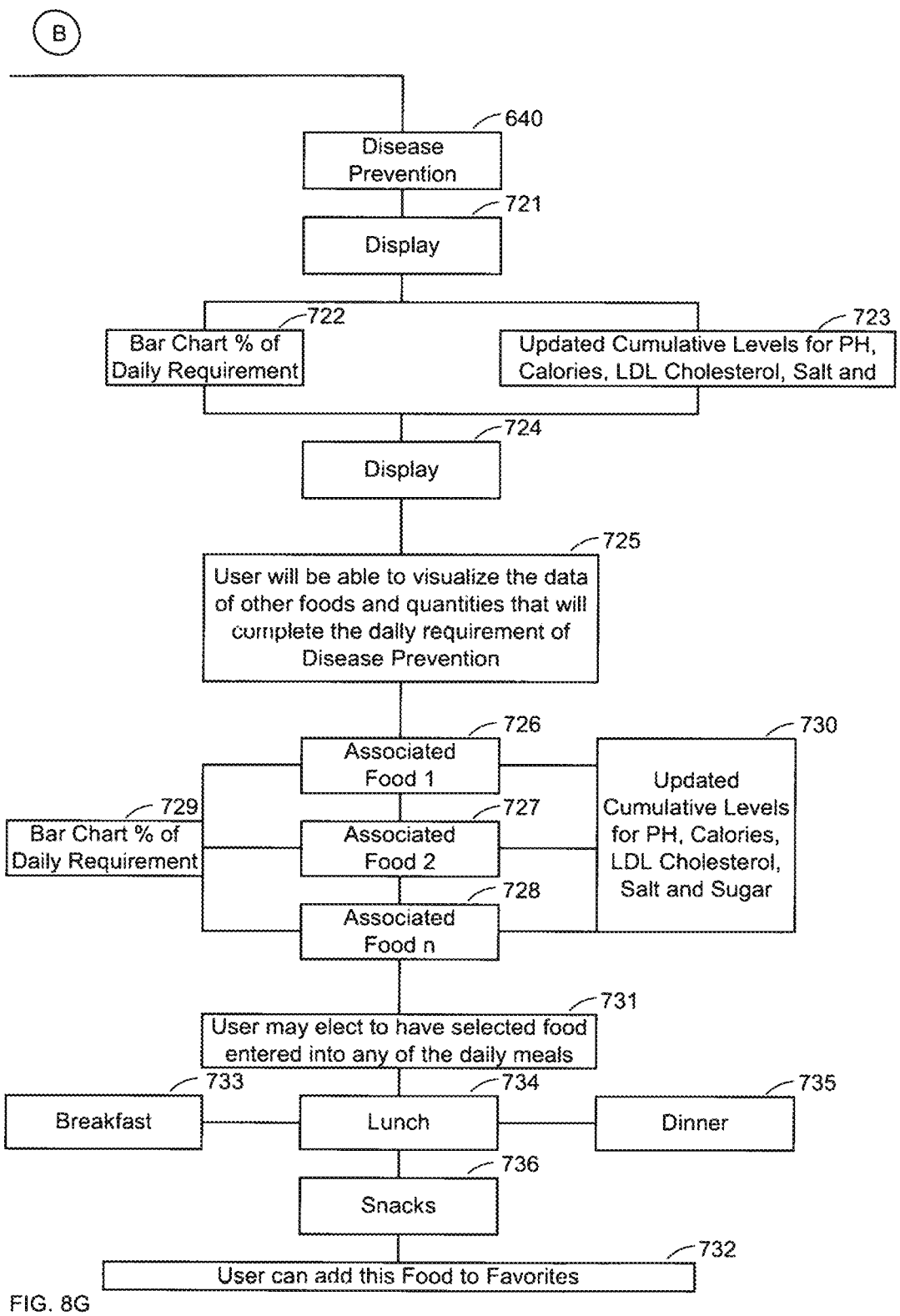
Figure 9A:
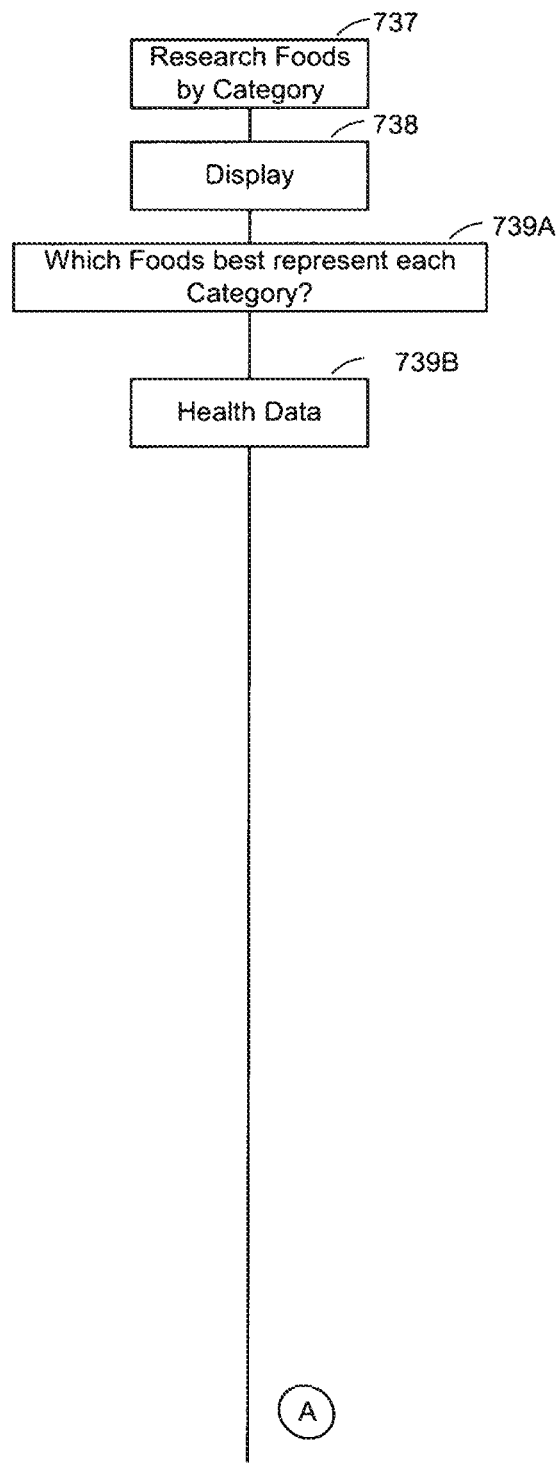
FIGS. 9A-G are components of a flow chart that depicts how a user can research the foods that best represent the various categories: Minerals, Vitamins, Phytochemicals, Positive Body Functions, Health Goals and Disease Prevention.
Figure 9B:
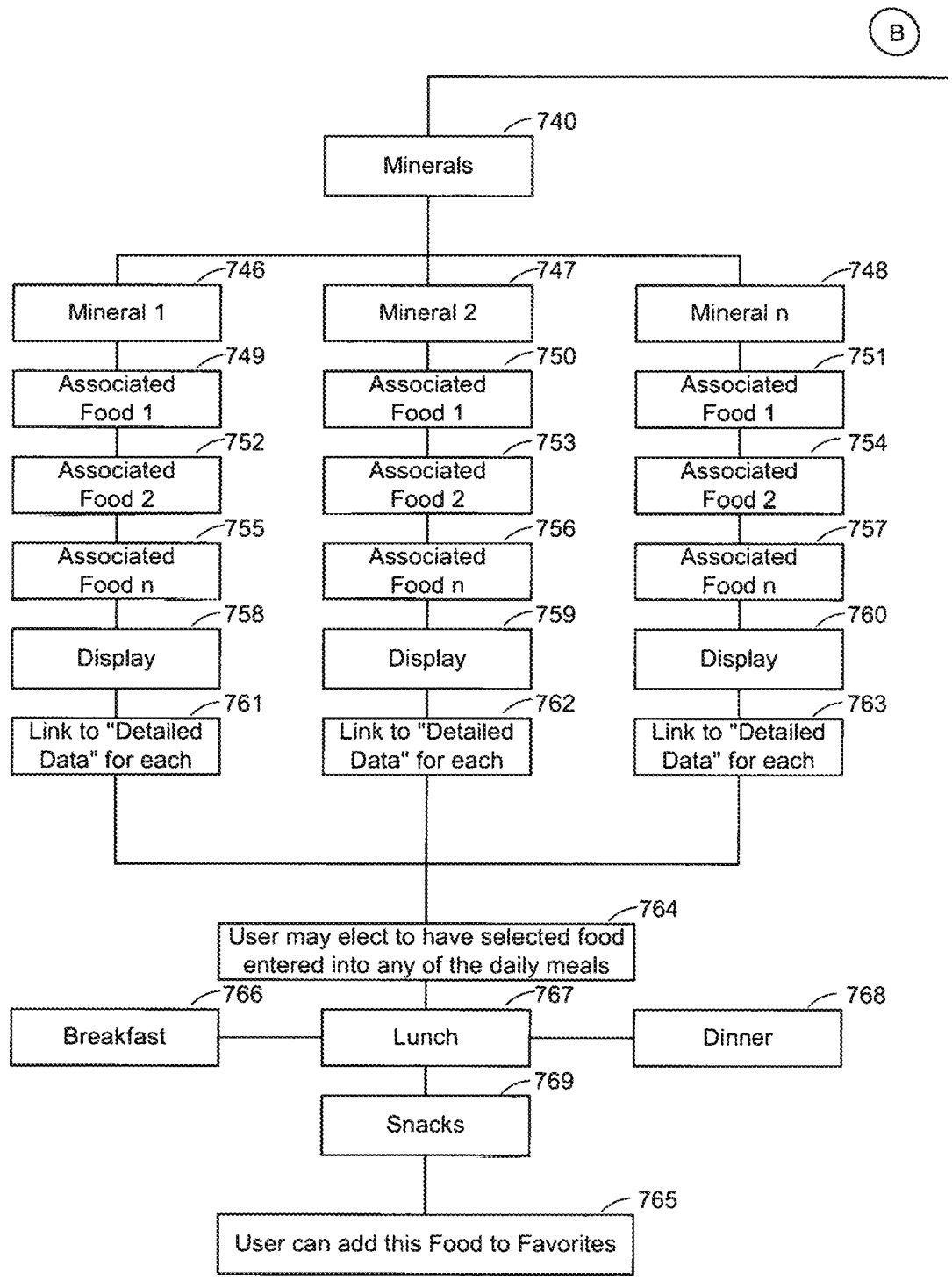
Figure 9C:
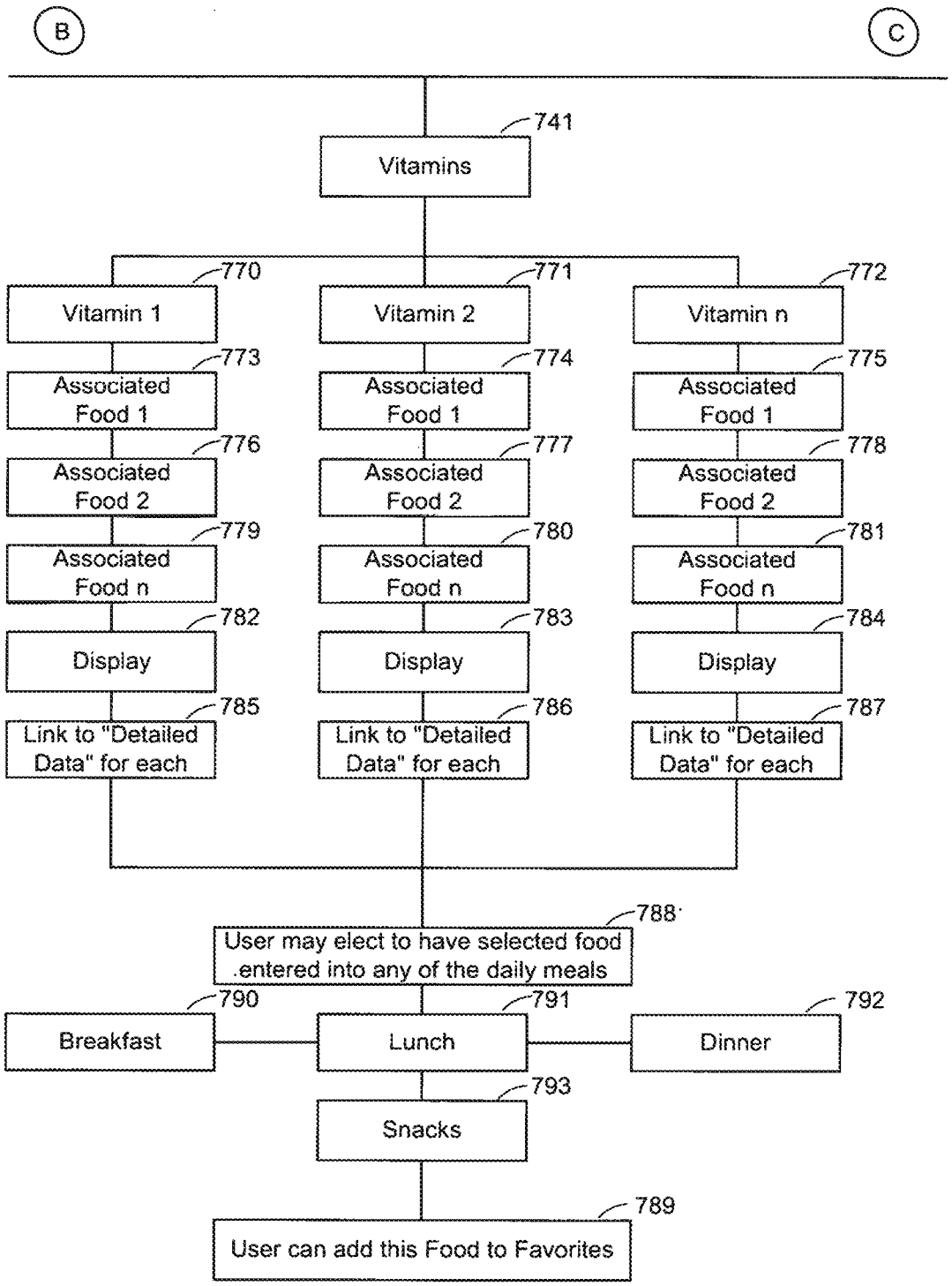
Figure 9D:
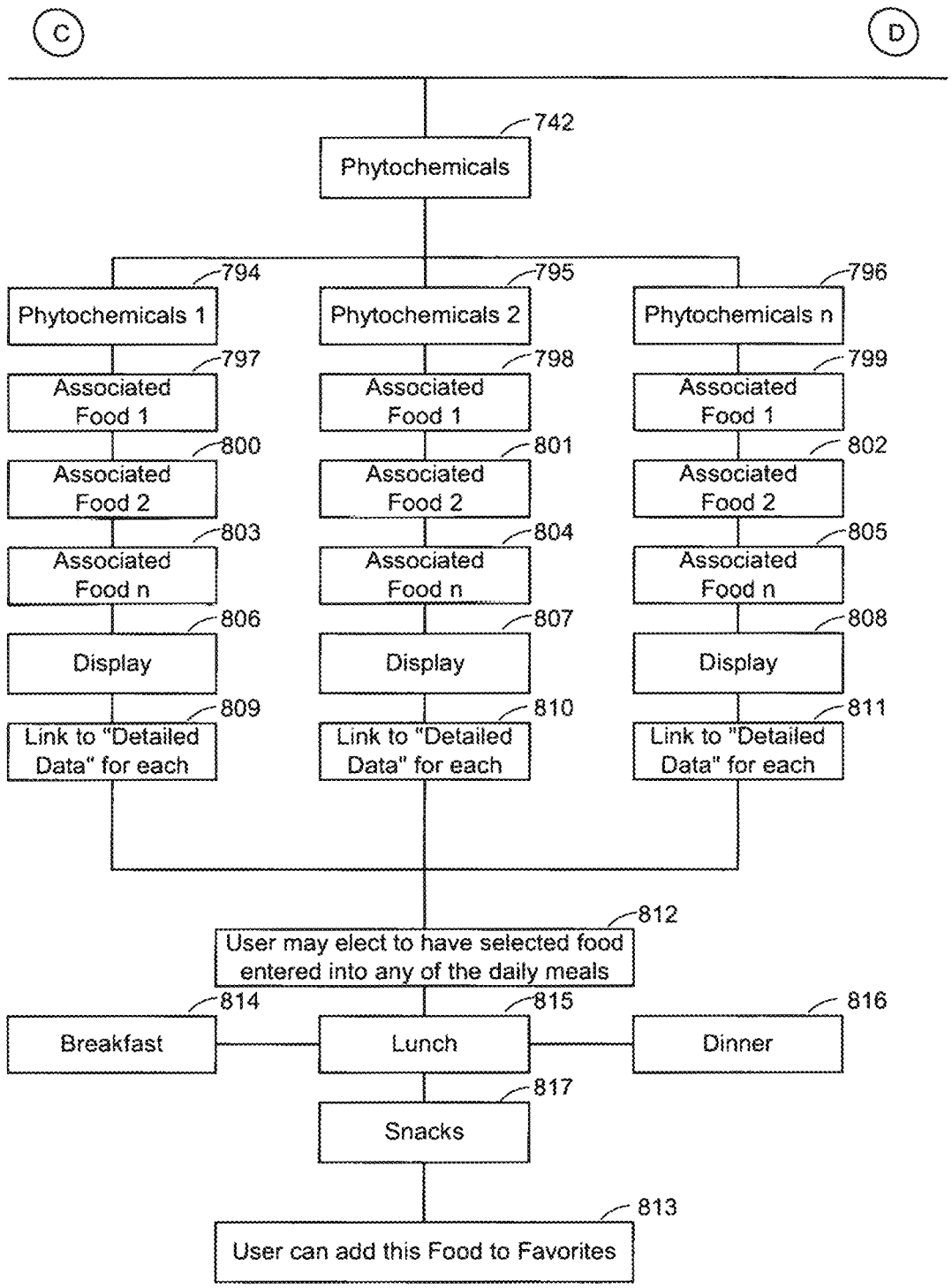
Figure 9E:
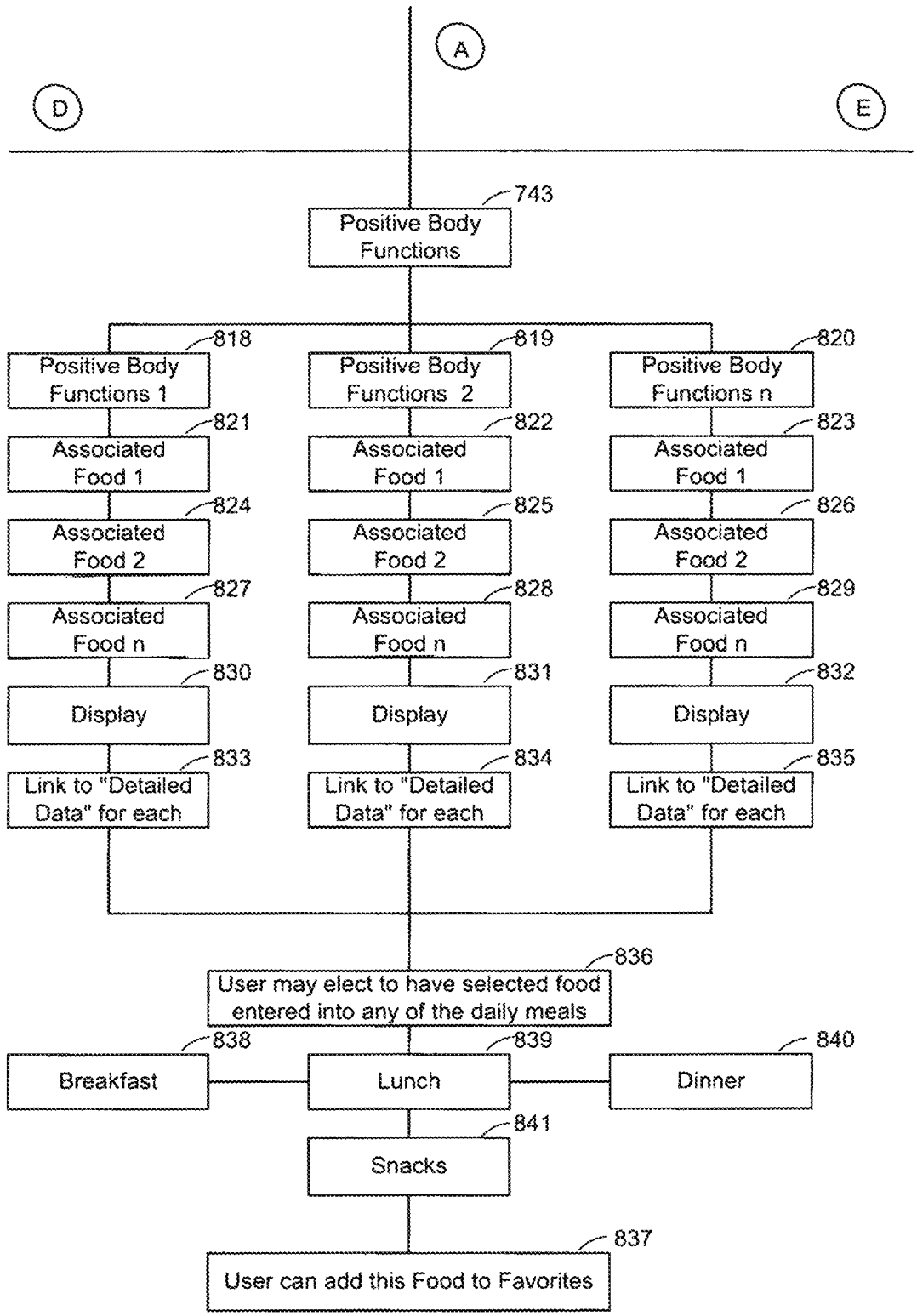
Figure 9F:
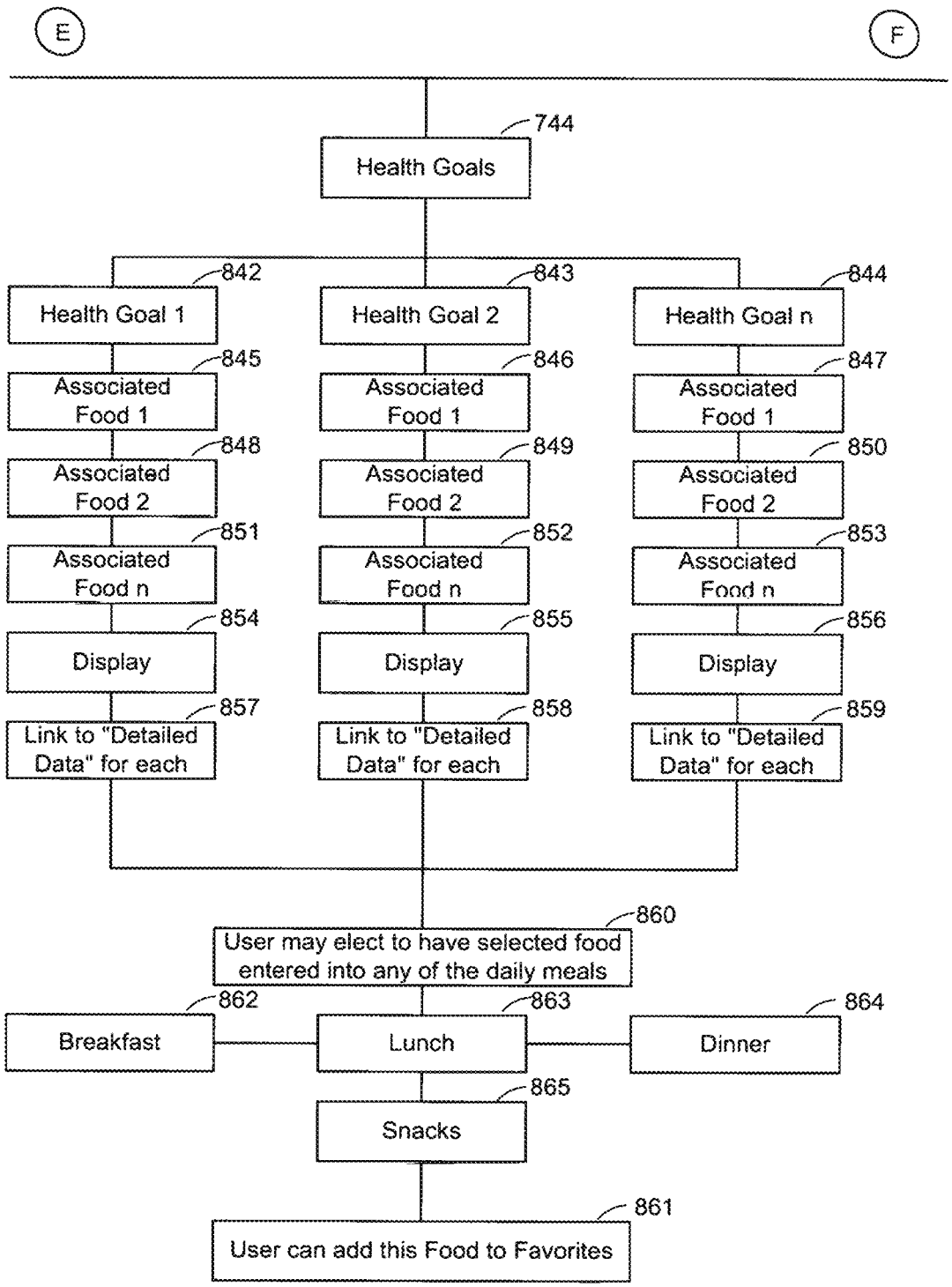
Figure 9G:
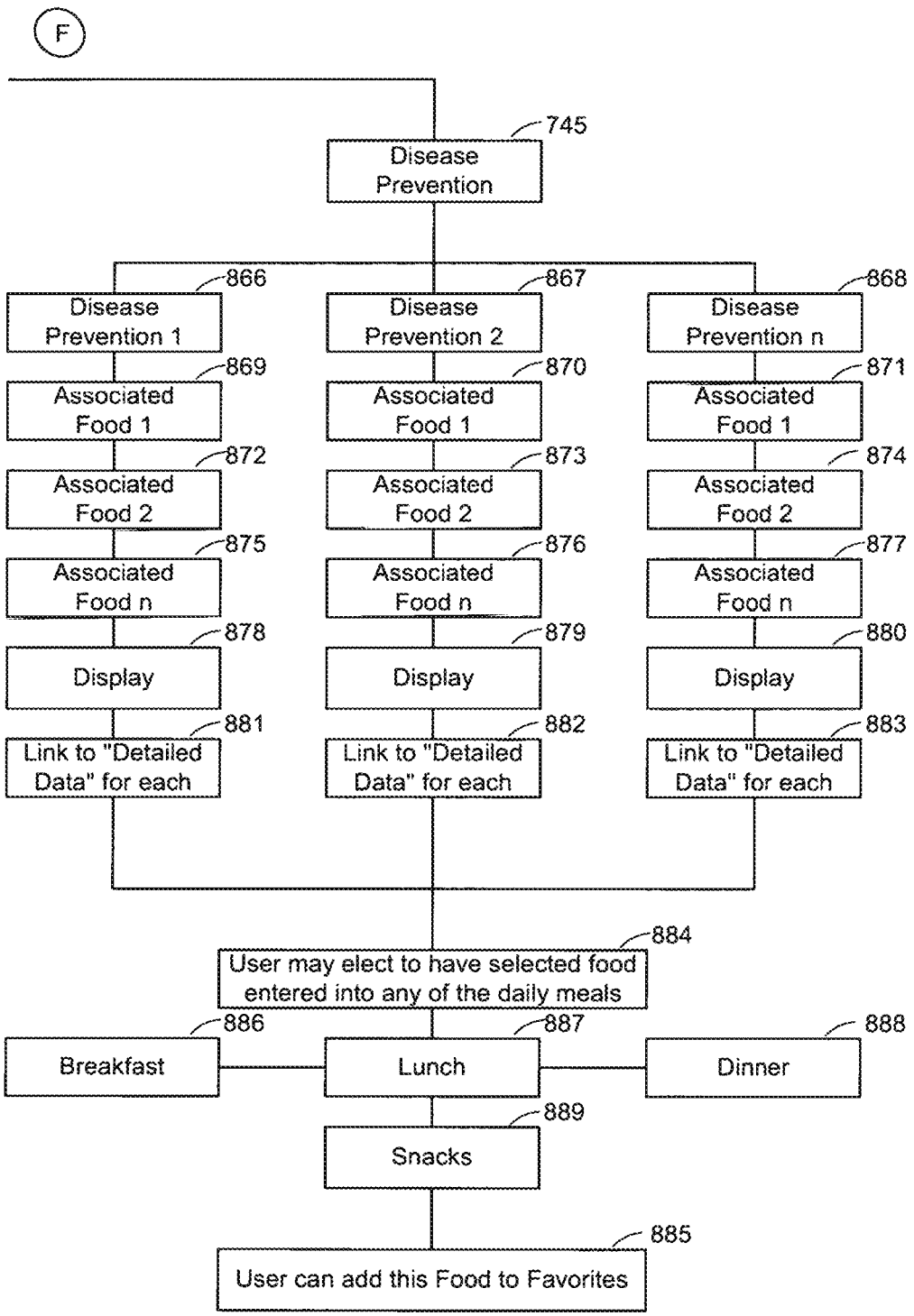

Where:
'OS' is the Optimizer Score
'DRA' is Daily required amount
'M' is Minerals, such as Calcium, Iodine, Iron, Magnesium, Manganese, Phosphorous, Potassium, Selenium, Sodium and Zinc
'V' is Vitamins, such as Vitamin A, Vitamin B1, Vitamin B2, Vitamin B3, Vitamin B6, Vitamin B12, Vitamin C, Vitamin D, Vitamin E and Vitamin K
'P' is Phytochemicals, such as Polyphenols, Lycopene, Lutein, Phytosterols, Saponins, Phenols, Flavonoids, Isothiocyanates, Ferulic Acid, Indoles
'PBF' is Positive Body Function, such as Healthy Vision, Healthy Skin, Healthy Nails, Cancer Protection, Anti Inflammatory, Antioxidant, Reduction in Bone Loss, Immunity Booster, Reduction in LDL Cholesterol and Heart Healthy
'DRL' is Daily Required Level
'HG' is Health Goals, such as Build Muscle, More Energy, Hair Growth, Weight Loss, Manage Blood Pressure, Manage Cholesterol, Mental Sharpness, Cancer Fighter, Enhance Metabolism and Fight Type 2 Diabetes
'DP' is Disease Prevention, such as Cancer, Type 2 Diabetes, Osteoporosis, Cardiovascular, Inflammation and Obesity
'PH' is PH—the acidity or alkalinity measurement
'DL' is Daily Limit
'C' is Calories
'SA' is Salt
'LDL' is LDL Cholesterol
'SU' is Sugar Required levels of the components of the Optimizer Score may be based upon responses to the introductory demographic questions shown in FIG. 6A regarding: Height 301, Weight 302, Age 303 and Activity Rate 306 as well as the Health Goals selected, and the optional laboratory information results inputted.

The user may be provided with an aggregate daily summary 228 at the end of the day.

The aggregate of the foods and quantities of foods consumed in that 24-hour period, starting at 12 AM, may have their health data displayed: Minerals 232, Vitamins 233, Phytochemical 234, Positive Body Functions 235, Health Goals 236 and Disease Prevention 237. Also, the aggregate Optimizer Score for the day may be displayed 238, along with the respective level moniker: Genius 239, Smarty Pants 241, Bright 243, Average 245, Slacker 247, Blockhead 249, Fool 251

Figure 2:
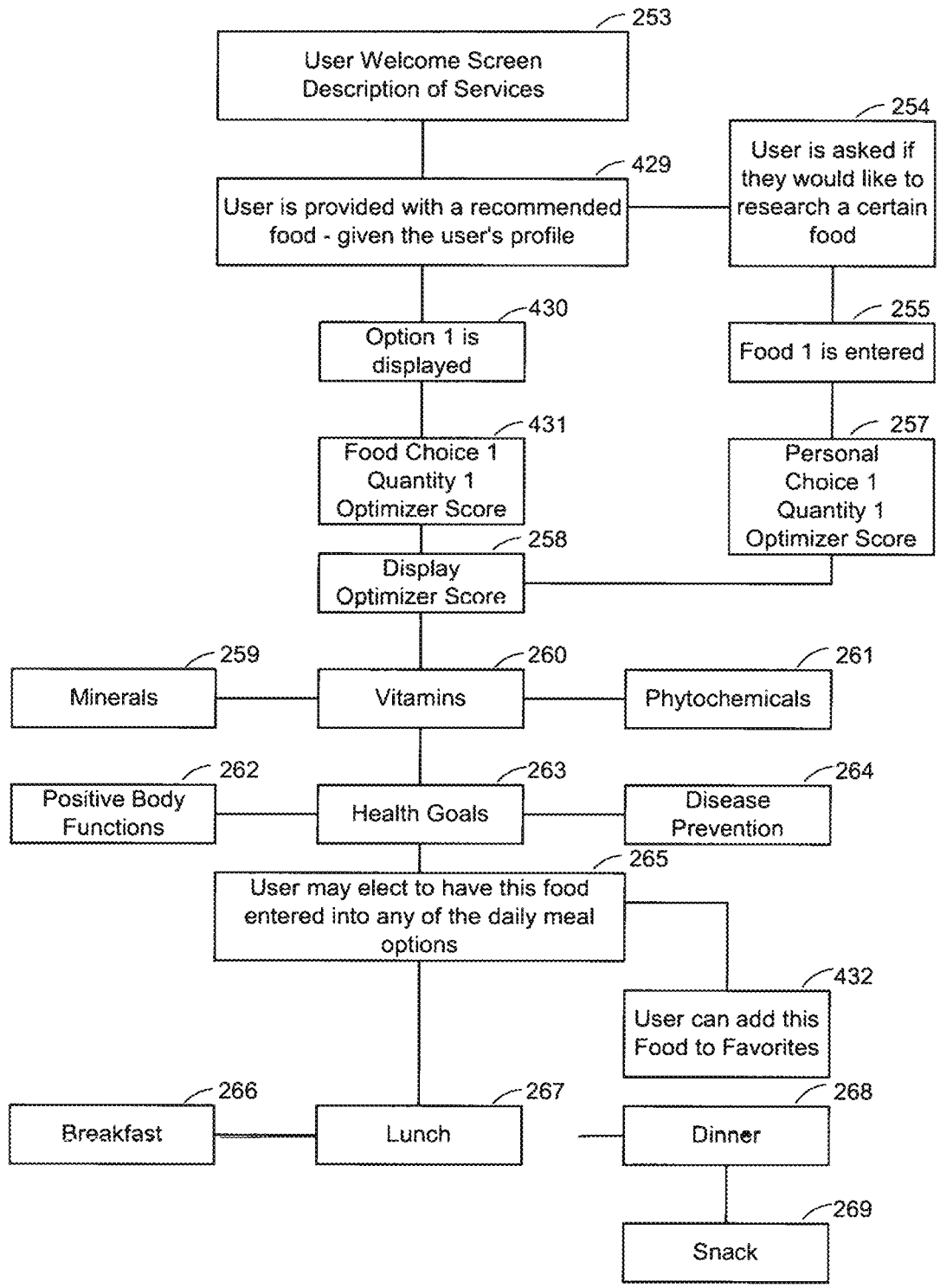
FIG. 2 is a flow chart that shows how a user can interact with the software application and utilize it as a resource for researching the Minerals, Vitamins, Phytochemicals, Supported Body Functions and Disease Prevention qualities of foods that are entered into the software application.
Figure 3A:
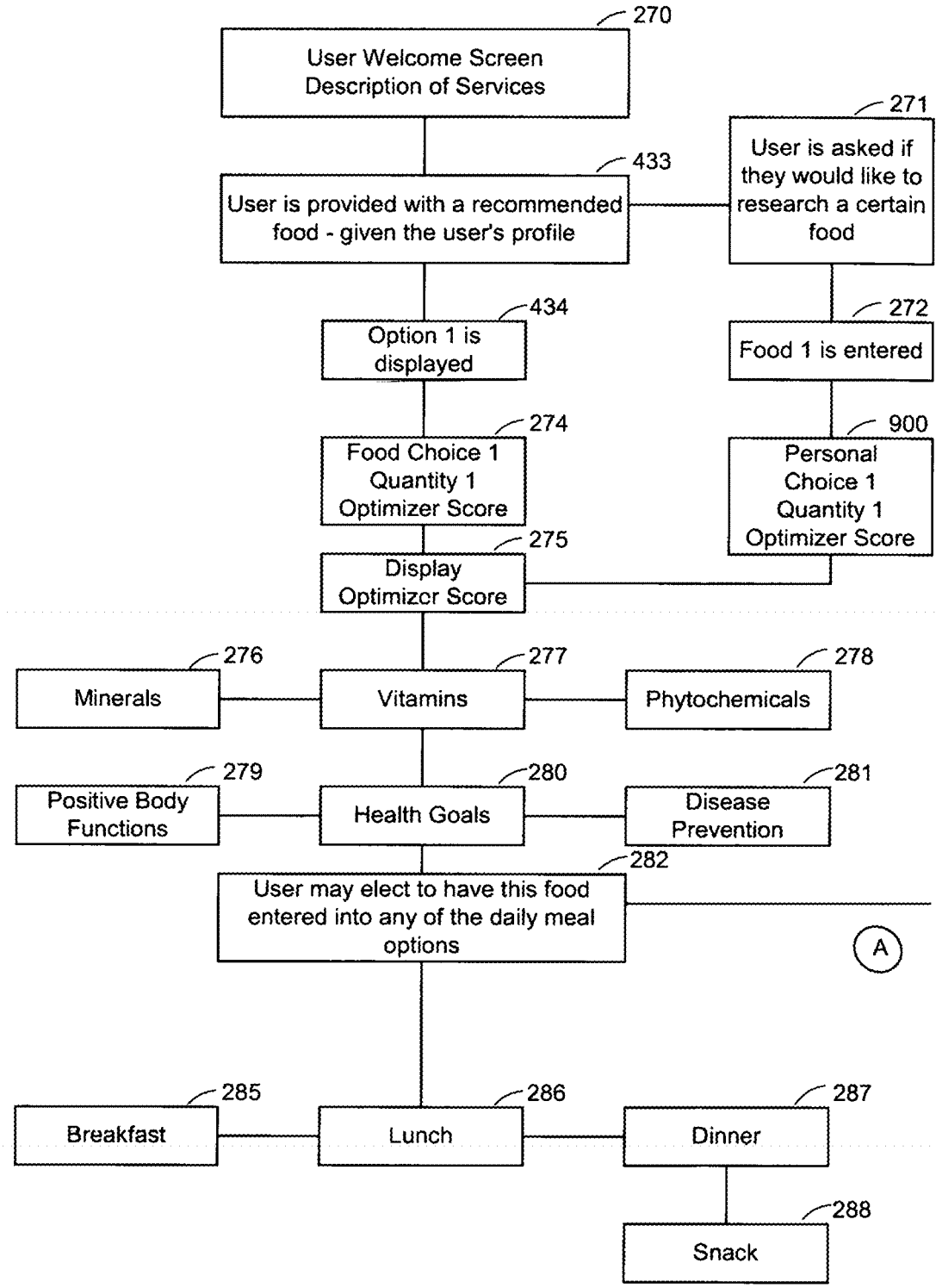
FIGS. 3A-E are components of a flow chart that shows how a user can elect to have foods, either raw ingredients or prepared meals, shipped to them directly based upon their food research.
Figure 3B:
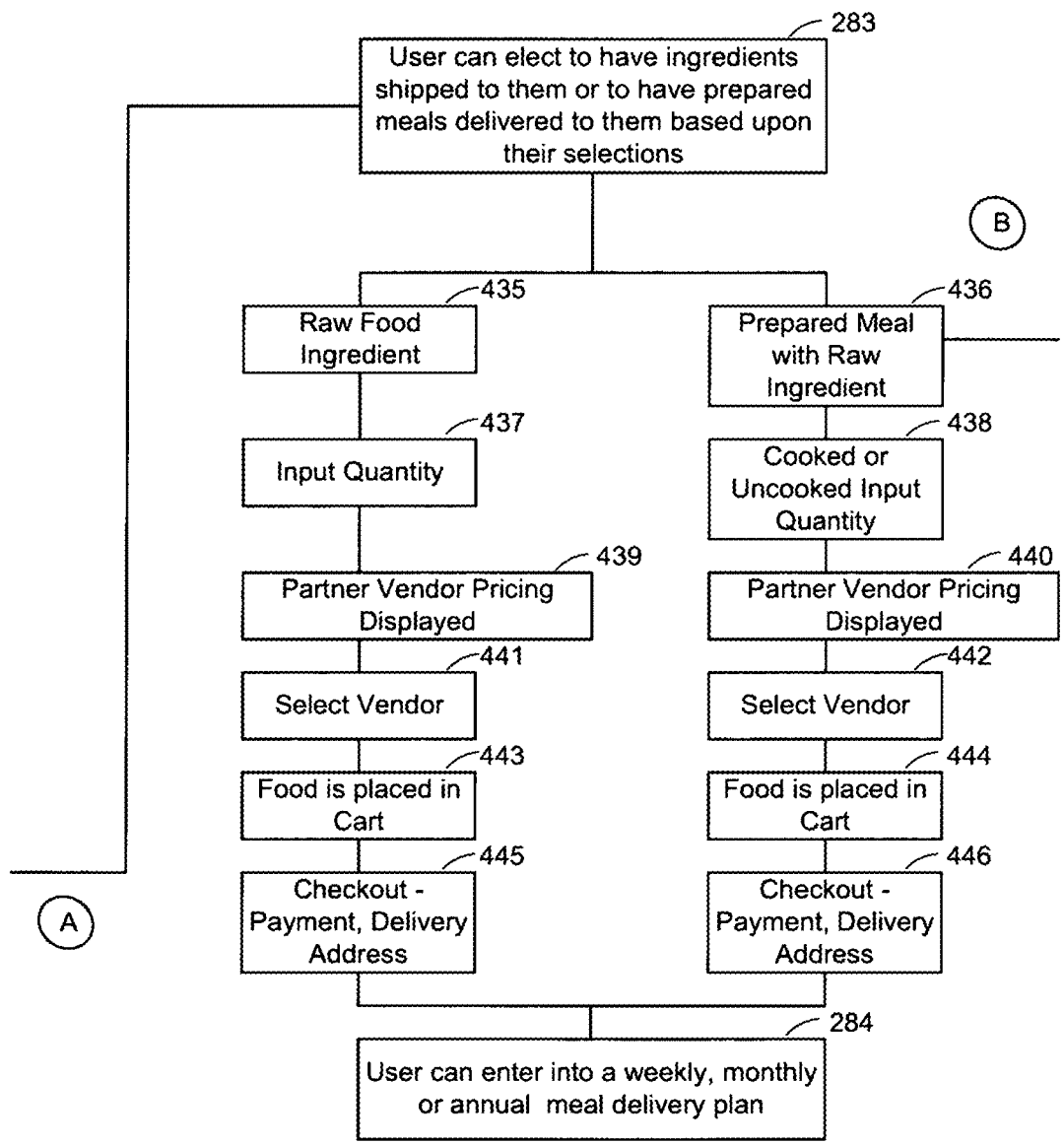
Figure 3C:
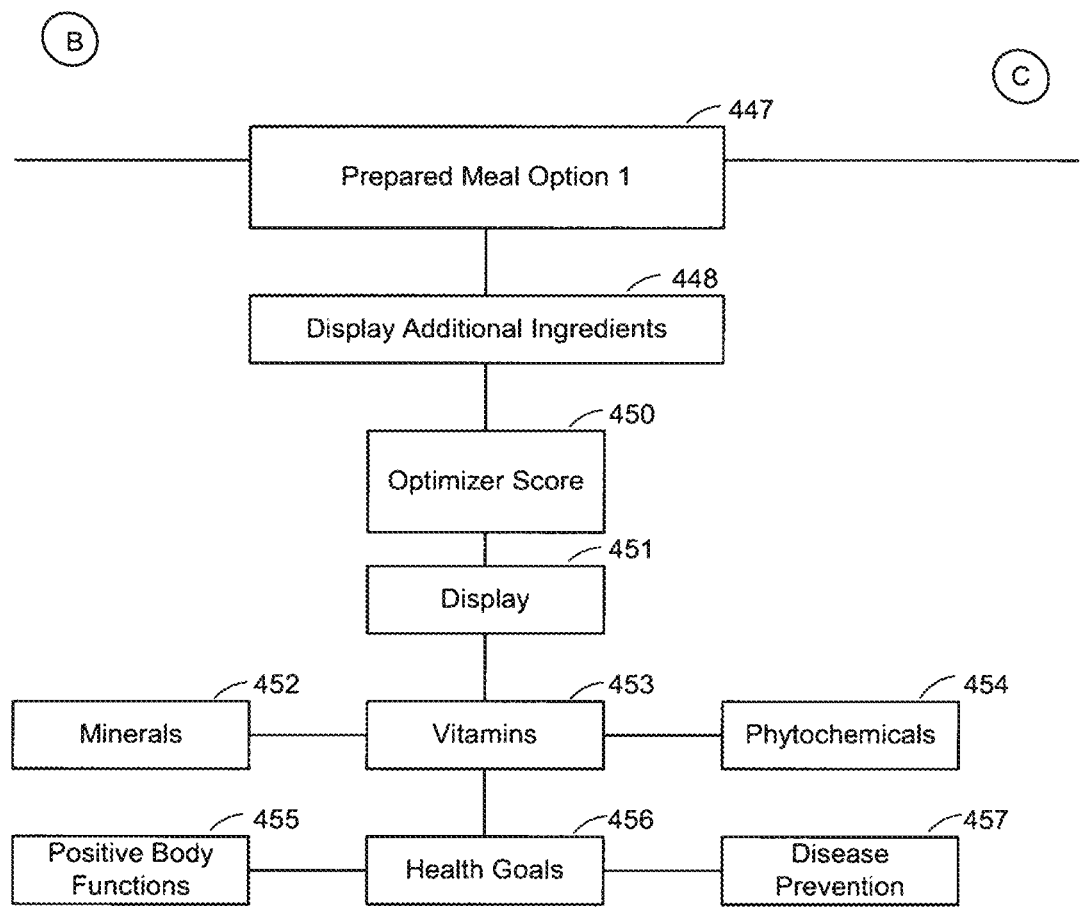
Figure 3D:
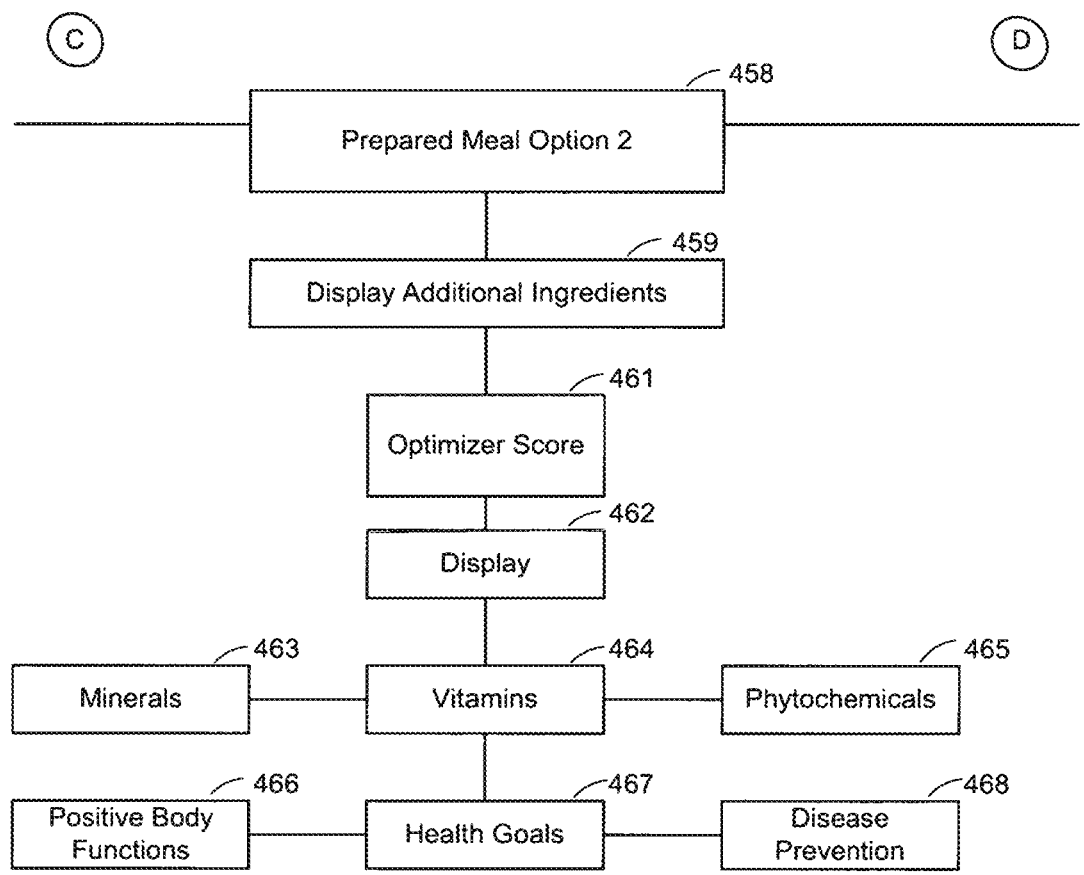
Figure 3E:
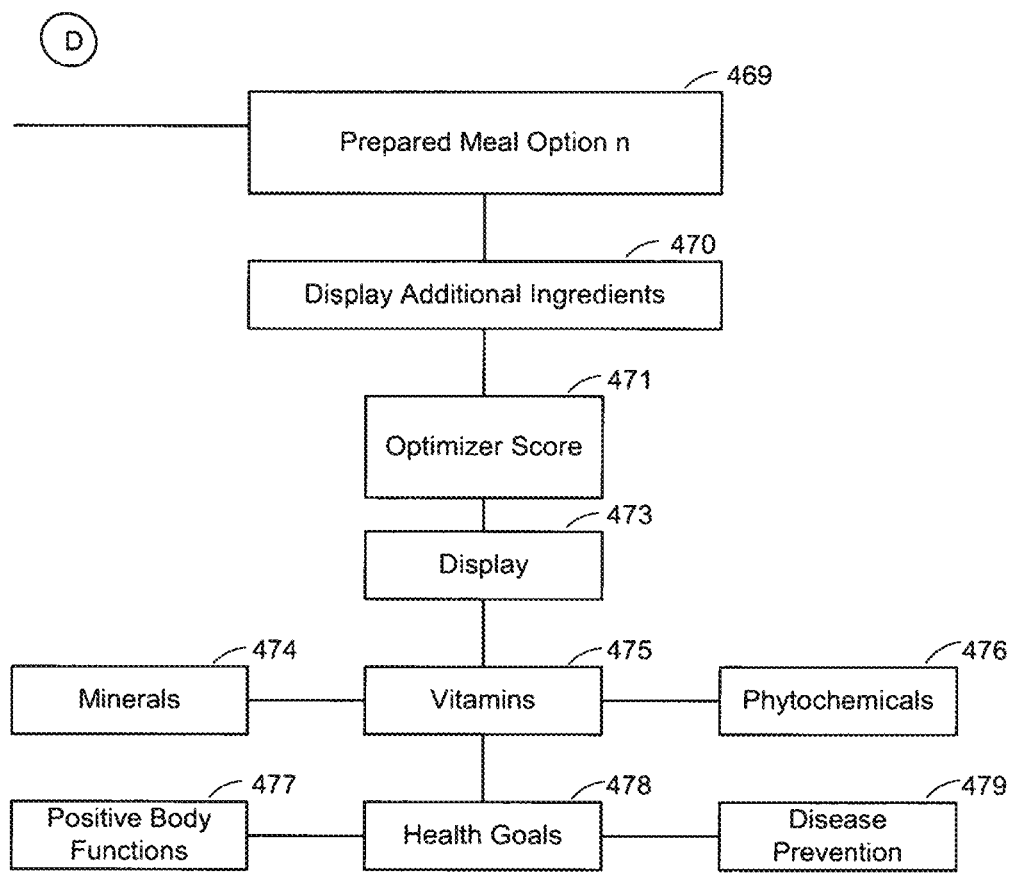

FIG. 2 is a flow chart that may depict the data on each food that a user is provided with each time they are prepared to make a decision on a meal. The user may see a display of a recommended food 429 for a particular meal: Breakfast, Lunch, Dinner or Snack. The user may also be provided with the option to enter their own choice into the software application 254. For each choice of food and quantity made 431 or 257 the user may see the respective Optimizer Score for that food displayed 258, as well as the respective health data which may include Minerals 259, Vitamins 260, Phytochemical 261, Positive Body Functions 262, Health Goals 263 and Disease Prevention 264. The user may elect to have the researched food entered into any one of the daily meal options 265: Breakfast 266, Lunch 267, Dinner 268 and Snack 269. A detailed flow chart, depicting the extent of research data for each food, is set forth in FIGS. 8A-G.

FIGS. 3A-E is a flow chart that depicts how a user may elect 282 to have certain foods or a prepared meal, with the selected ingredients, delivered to their destination of choice 283. The user can enter into a weekly, monthly or annual meal delivery plan 284.

The user may have the option to have the raw ingredients 435 delivered or the raw ingredients included in a prepared meal with other ingredients 436 delivered. If the user elects to have the raw ingredient delivered, they may enter the quantity they are looking to have delivered 437. Partner Vendors may provide competing pricing 439. The user may select a vendor 441 and have the food placed in a virtual cart 443 and checkout by providing payment information and delivery address 445.

If the user elects to view prepared meals 436, with the main ingredient included, they may elect to do so. The prepared meals may be displayed for the user to select from 447, 458, 469 ('n' used to designate from 1 to 'n' selections). Each meal will display the additional ingredients 448, 459, 470 and the meal's combined respective Optimizer Score 450, 461, 471. The health data for each respective prepared meal may then be displayed: Minerals 452, 463, 474, Vitamins 453, 464, 475, Phytochemicals 454, 465, 476, Positive Body Function 455, 466, 477, Health Goals 456, 467, 478 and Disease Prevention 457, 468, 479.

The user may then decide whether to have the prepared meal shipped cooked or to have the combined raw ingredients shipped uncooked 438. Partner Vendors may provide competing pricing 440. The user may select a vendor 442 and have the food placed in a virtual cart 444 and checkout by providing payment information and delivery address 446.

Figure 5:
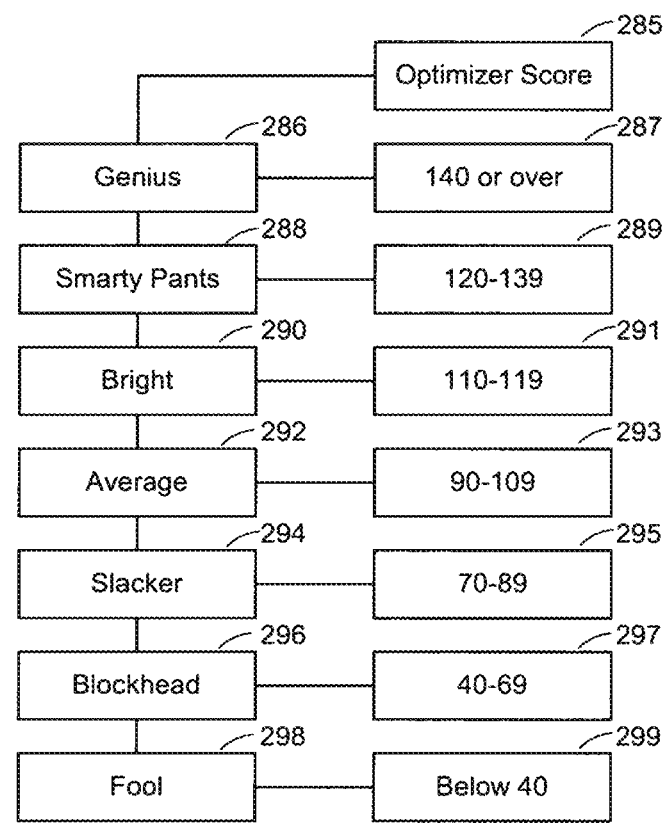
FIG. 5 is a description of the various levels of the MychewIQ Optimizer scores.

FIG. 5 delineates the various levels of the MychewIQ Optimizer Score: Genius 286, Smarty Pants 288, Bright 290, Average 292, Slacker 294, Blockhead 296, Fool 298; it should be understood that these characterization are a matter of choice and substitute characterization may be used with diverging from the overall intent of the present invention. In one embodiment the Optimizer Score may be designed to mimic an IQ score. Over time, a user may realize that eating just to satisfy hunger, without taking into account the nutritional value and positive health effects of foods, may be less than optimal. A higher MychewIQ score may be associated with a person that is very knowledgeable about the foods they are eating, the quantity of foods they are eating and how they can positively affect the human body. The algorithm, which is an integral part of the present invention, may be designed around having an Optimizer score of 140 or above. The algorithm may pull nutritional information from databases, incorporate health data such as health goals, positive body function and disease prevention into a complex formula which is then translated into an easy to follow score. If one is scoring 140 or above, user may be ensuring that all of ones body's nutritional needs are being met; user is not consuming more food on a daily basis than is required and user is not consuming too much of foods that are not beneficial to ones health. There may be a negative score associated with consuming foods that are not beneficial to user's health. This negative score may get incorporated into the algorithm that computes the Optimizer Score.

Foods and their respective quantities may have an Optimizer Score. Each 24 hour period may have an Aggregate Optimizer Score. Also, each user may have a cumulative Optimizer Score that takes into account all the consumed food and respective quantities for the days that data was inputted.

The Optimizer Score may based upon achieving 100% of the daily required amount of the following categories on a daily basis:
  Minerals
  Vitamins
  Phytochemicals The Optimizer Score may be based upon achieving 100% of the daily required level of the following categories on a daily basis:
  Health Goals
  Positive Body Function
  Disease Prevention
  PH There may also a negative effect on your Optimizer score for the following categories:
  Exceeding the recommended daily Calorie limit
  Exceeding the daily LDL Cholesterol limit
  Exceeding the daily Sodium (salt) limit
  Exceeding the daily Sugar limit Optimizer Score=(% daily Minerals Level×20)+(% daily Vitamins Level×20)+(% daily Phytochemicals Level×20)+(% daily Health Goals Level×20)+(% daily Positive Body Functions Level×20)+(% daily Disease Prevention Level×20)+(% daily PH Level×20)[(% over daily recommended calorie intake×10)+(% over daily limit for salt×10)+(% over daily limit for LDL cholesterol×10)+(% over daily limit for sugar×10)]

OS=(% DRA(M)×20)+(% DRA(V)×20)+(% DRA(P)×20)+(% DRL(PBF)×20)+(% DRL(HG)×20)+(% DRL(DP)×20)+(% DRL(PH)×20)−[(% over DL(C)×10))+(% over DL(SA)×10)+(% over DL(LDL)×10)+(% over DL(SU)×10)]

Where:
'OS' is the Optimizer Score
'DRA' is Daily required amount
'M' is Minerals, such as Calcium, Iodine, Iron, Magnesium, Manganese, Phosphorous, Potassium, Selenium, Sodium and Zinc
'V' is Vitamins, such as Vitamin A, Vitamin B1, Vitamin B2, Vitamin B3, Vitamin B6, Vitamin B12, Vitamin C, Vitamin D, Vitamin E and Vitamin K
'P' is Phytochemicals, such as Polyphenols, Lycopene, Lutein, Phytosterols, Saponins, Phenols, Flavonoids, Isothiocyanates, Ferulic Acid, Indoles
'PBF' is Positive Body Function, such as Healthy Vision, Healthy Skin, Healthy Nails, Cancer Protection, Anti Inflammatory, Antioxidant, Reduction in Bone Loss, Immunity Booster, Reduction in LDL Cholesterol and Heart Healthy
'DRL' is Daily Required Level
'HG' is Health Goals, such as Build Muscle, More Energy, Hair Growth, Weight Loss, Manage Blood Pressure, Manage Cholesterol, Mental Sharpness, Cancer Fighter, Enhance Metabolism and Fight Type 2 Diabetes
'DP' is Disease Prevention, such as Cancer, Type 2 Diabetes, Osteoporosis, Cardiovascular, Inflammation and Obesity
'PH' is PH—the acidity or alkalinity measurement
'DL' is Daily Limit
'C' is Calories
'SA' is Salt
'LDL' is LDL Cholesterol
'SU' is Sugar Required levels of the components of the Optimizer Score may be based upon responses to the introductory user demographic inquiries shown in FIG. 6A regarding: Height 301, Weight 302, Age 303 and Activity Rate 306 as well as the Health Goals selected, and the optional laboratory information, such as blood and urine work, results inputted.

FIGS. 6A-G are components of a flow chart that takes the user through the process of selecting Health Goals. In order to get a better profile of the user, the user may be asked to provide answers to the following demographic inquires: What is your Height 301, What is your current Weight 302, What is your Age 303, Do you have any Food Restrictions 305, choices include Omnivore 429, Vegan 430, Vegetarian 431, Food Allergies 432, Activity Rate 306, choices include Low—description of low included 422, Medium—description of medium included 423, and High—description of high included 424, their Shipping address 304 and user's Sex—Male or Female 421.

The user may then decide to select from the Health Goals from a menu 307. The user may be provided with the option to enter laboratory information, such as recent blood and urine work 308. This is explained in greater detail in FIGS. 7A-F. This option allows the algorithm to determine what some of the user's health deficiencies and strengths are.

The user may select from the following Health Goals:
309 Healthy Vision
310 Build Muscle
311 More Energy
312 Healthy Immune System
313 Hair Growth
314 Healthy Skin
315 Healthy Nails
316 Heart Healthy
317 Weight Loss
318 Manage Blood Pressure
319 Manage Cholesterol
320 Mental Sharpness
321 PH Level
322 Cancer Fighters
323 Anti Inflammatory
324 Healthy Bones & Fight Osteoporosis
325 Enhance Metabolism
326 Fight type 2 Diabetes As the user peruses a Health Goal, the user may see a display 327-344 of the respective description of the Health Goals 345, 346, 347, 348, 349, 350, 351, 352, 353, 354, 355, 356, 357, 358, 359, 360, 361 and 362 as well as various foods that are associated with the respective Health Goals 363-416.

For example, the user may elect to peruse the Health Goal, Healthy Vision 309 and then may elect to see the description of Healthy Vision 345. The description may set forth how certain foods can reduce the risk of age-related eye disease, such as cataracts, cloudy areas in the lens of the eye, and age related macular degeneration, a condition where the macula, which controls central vision, degenerates to the point where vision is lost. Lutein and Zeaxanthin are carotenoids with antioxidant qualities. Vitamins A, C, E and the mineral Zinc may also have antioxidant qualities. These antioxidants may be needed to fight off free radicals that can damage the eye. Omega-3 fatty acid DHA (docosahexaenoic acid), which has an anti-inflammatory property, may be present in high concentrations in the outer segments of retinal photoreceptors. Inflammation, a common denominator with many illnesses, plays a role in age related macular degeneration.

The foods that contain the nutrients, minerals, vitamins and phytochemicals that may help maintain Health Vision are displayed such as Spinach, rich in Lutein, Zeaxanthin and Vitamins—Associated Food 363, Salmon—rich in Omega-3 fatty acids, Associated Food 381 and Almonds, rich in Vitamin E—Associated Food 399. The algorithm may show more than three Associated Foods. Associated Food n 399 uses the 'n' to designate up to "n" different associated foods. The options of foods displayed may take into account the profile questions answered, specifically the ones concerning Food Restrictions 305, choices include Omnivore 429, Vegan 430, Vegetarian 431 and Food Allergies 432.

A display 421 may then provide the user with the choice to select the Health Goal 422. Also, if the user is interested in some of the foods listed under the Health Goal, user may elect to include some or all of them in their favorites 423. The algorithm may access from the user's favorites when suggesting foods. The user may also determine 424 if they want to include certain foods for Breakfast 425, Lunch 426, Dinner 427 or Snacks 428.

In FIGS. 7A-F the flow chart shows how a user may input results from recent laboratory information 494, in order to have the algorithm better determine what health goals should be included in the user's profile.

The user may be asked to input results for the following categories:
495 Sodium level
496 Potassium level
497 Glucose Level
498 Total Protein
499 Calcium, Serum level
500 Triglyceride Level
501 Cholesterol Level
502 HDL Cholesterol level
503 LDL Cholesterol level
504 PSA level
505 TSH level
506 PH level
507A Vitamin D level
507B C-Reactive Protein Based upon where the inputted results fall in each respective reference range 510, 519, 528, 537, 546, 555, 564, 573, 582, 591, 600, 609, 618A, 618B a related health goal may be recommended 511, 520, 529, 538, 547, 556, 565, 574, 583, 592, 601, 610, 619A, 619B a related body function may be displayed 512, 521, 530, 539, 548, 557, 566, 575, 584, 593, 602, 611, 620A, 620B a related disease prevention may be displayed 513, 522, 531, 540, 549, 558, 567, 576, 585, 594, 603, 612, 621A, 621B. For each category, there may be several foods listed that will help improve results. For example, Sodium level 495 may have Associated Foods listed 514, 515, 516. There may be more than three foods listed. The 'n' in Associated Food 516 is meant to designate up to "n" different associate foods. If the user likes the foods, they may have the option 625 to enter the foods as a favorite 626 and or into their meal plan 627: Breakfast 628, Lunch 629, Dinner 630 or Snack 631.

For example, the user may enter their LD Cholesterol level 503 at 155 mg/dL. The reference range 582 displayed is <=129. The recommendation displayed may be that you should work to lower your LDL Cholesterol. The related Health Goal 583 displayed may be 'Manage Cholesterol'. The user may have an option to select this Health Goal. The related Body Function 584 may be displayed: Too much LDL Cholesterol in the body can cause the buildup of plaque in the arteries and the hardening and narrowing of the arteries, known as Atherosclerosis, which may lead to reduced blood flow, heart attacks, strokes, gallstones. The related disease prevention 585 displayed may be high blood pressure, coronary heart disease and peripheral vascular disease. The foods that can help reduce your LDL Cholesterol may be displayed as: Artichoke 586—Cynarin is a compound found in Artichokes that helps increase the production of bile in the liver and gall bladder. Bile may help remove excess cholesterol from the body; Walnuts 587—are rich in polyunsaturated fats and a great source of plant based omega 3 fatty acids; Black Beans 588—rich source of soluble fiber; Oats 588$n$—contains soluble fiber, which may reduce the absorption of LDL Cholesterol into your bloodstream; Garbanzo beans 588$n$—high in fiber, antioxidant phytochemicals and minerals and the like.

In FIGS. 8A-G, the flow chart components illustrate what the user may visualize when analyzing a particular food. The food may be inputted 632 along with the quantity 633. The Optimizer Score may be displayed 634A. The user may then visualize 641, 657, 673, 689, 705, 721 a graphical 643, 658, 674, 690, 706, 722 display of the percent of daily requirement, the food and quantity inputted meets of the following health data categories: Minerals 635, Vitamins 636, Phytochemicals 637, Positive Body Function 638, Health Goal 639 and Disease Prevention 640 as well as a cumulative update on PH level, Calories, LDL Cholesterol, Salt and Sugar 642, 659, 675, 691, 707, 723.

The user may then see a display 644, 660, 676, 692, 708, 724, of the foods in each category and their respective quantity and Optimizer Score 646, 647, 648, 662, 663, 664, 678, 679, 680, 694, 695, 696, 710, 711, 712, 726, 727, 728 that will allow the user to meet the balance of the 100 percent of the daily requirement, in a graphical chart 649, 665, 681, 697, 713, 729 and the cumulative update on PH level, Calories, LDL Cholesterol, Salt and Sugar 650, 666, 682, 698, 714, 730 display.

The user may then be given the option to include these foods in to their daily meal plans 651, 667, 683, 699, 715, 731 for either Breakfast 653, 669, 685, 701, 717, 733, Lunch 654, 670, 686, 702, 718, 734, Dinner 655, 671, 687, 703, 719, 735 or Snack 656, 672, 688, 704, 720, 736.

The user may also elect to include any of the foods in their favorites 652, 668, 684, 700, 716, 732.

This analysis takes place every time a user is deciding on what foods to consume throughout the day. Also, the user may access this feature of the software application at any time to visualize the full data for a particular food and respective quantity of that food.

Figure 10A:
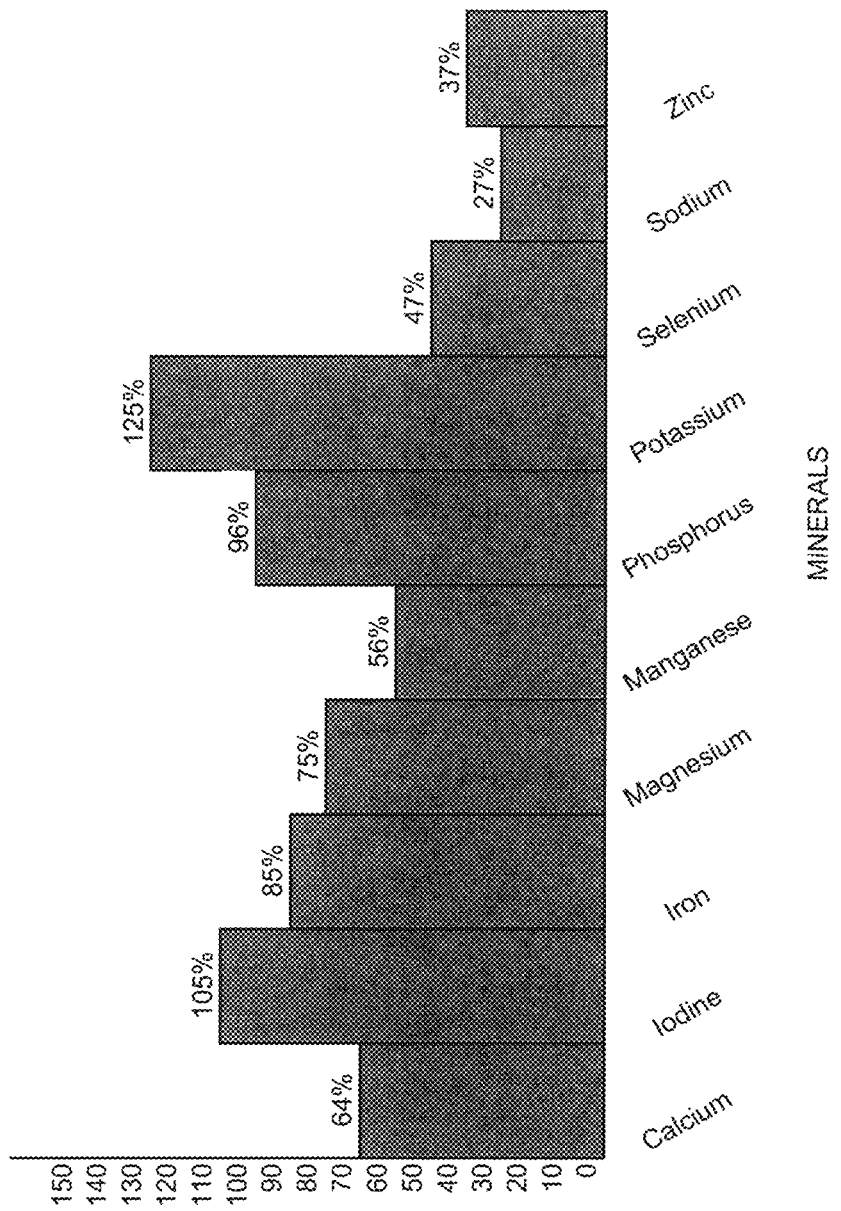
Figure 10B:
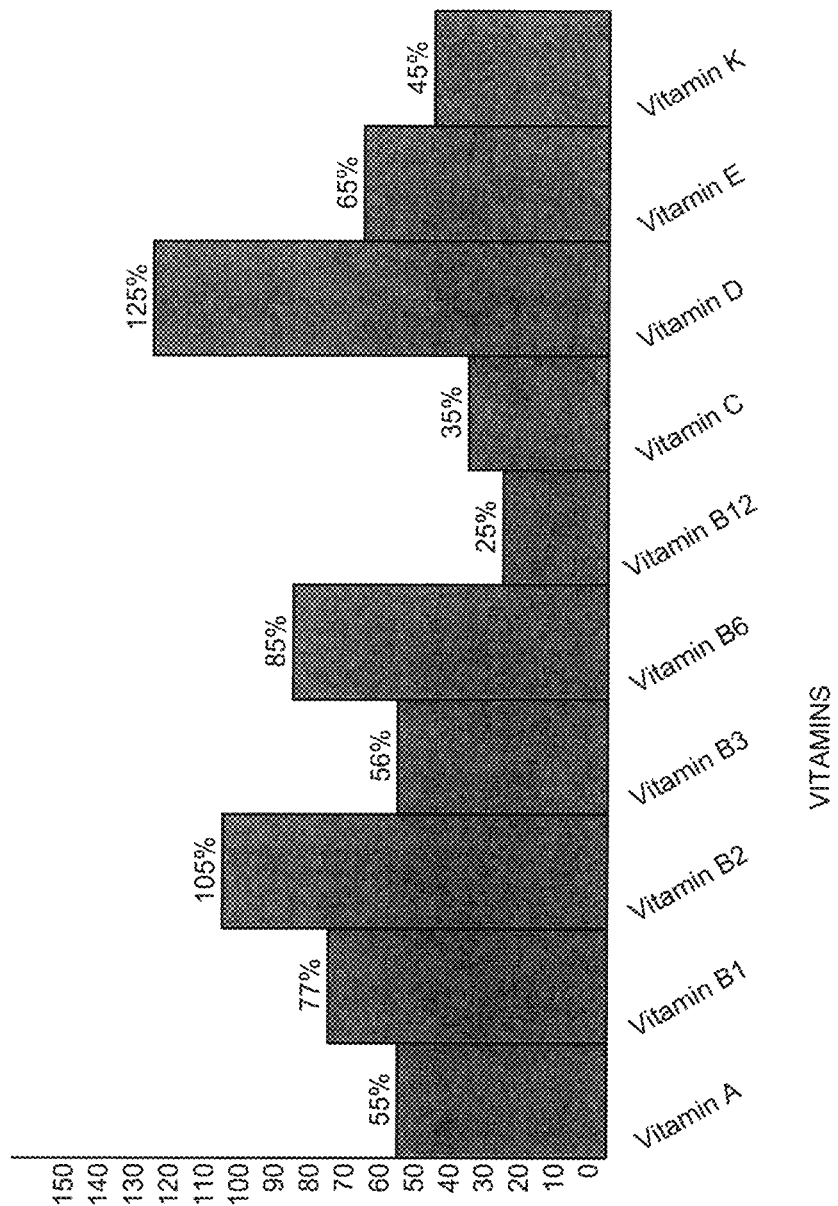
Figure 10C:
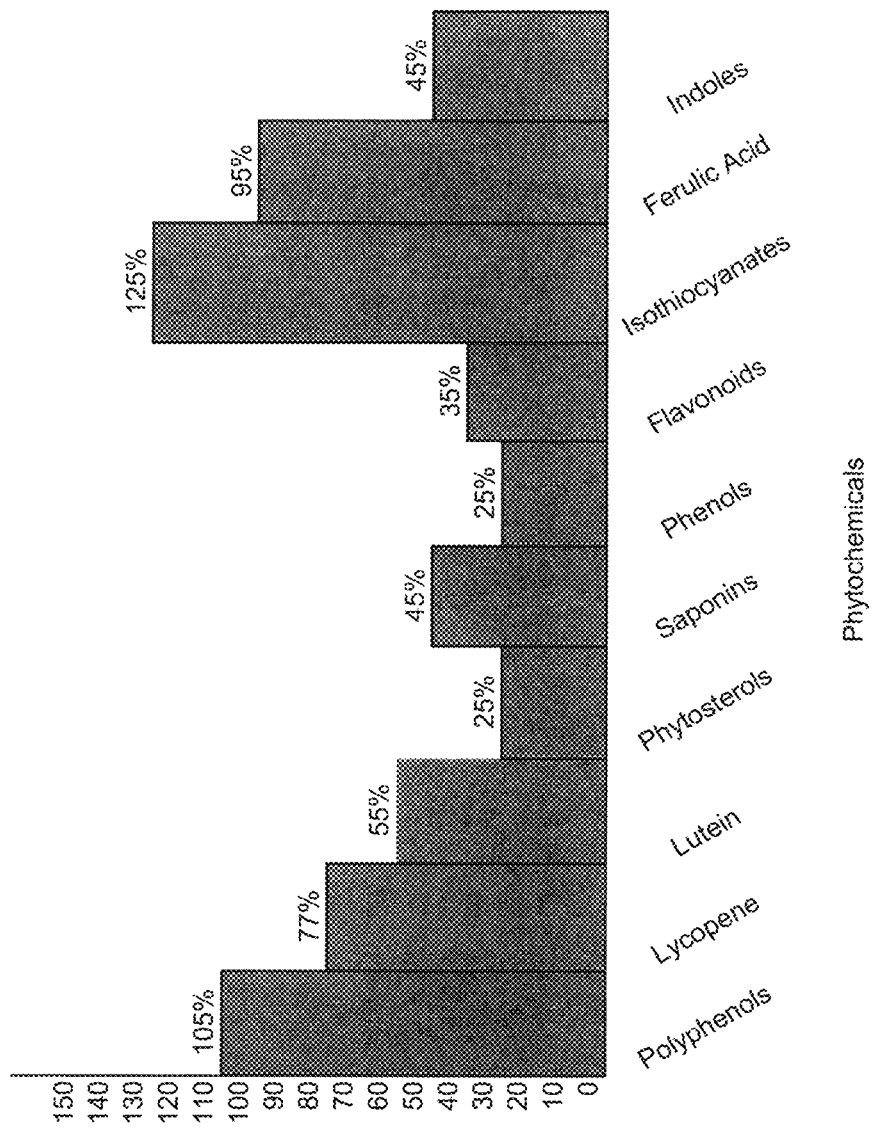
Figure 10D:
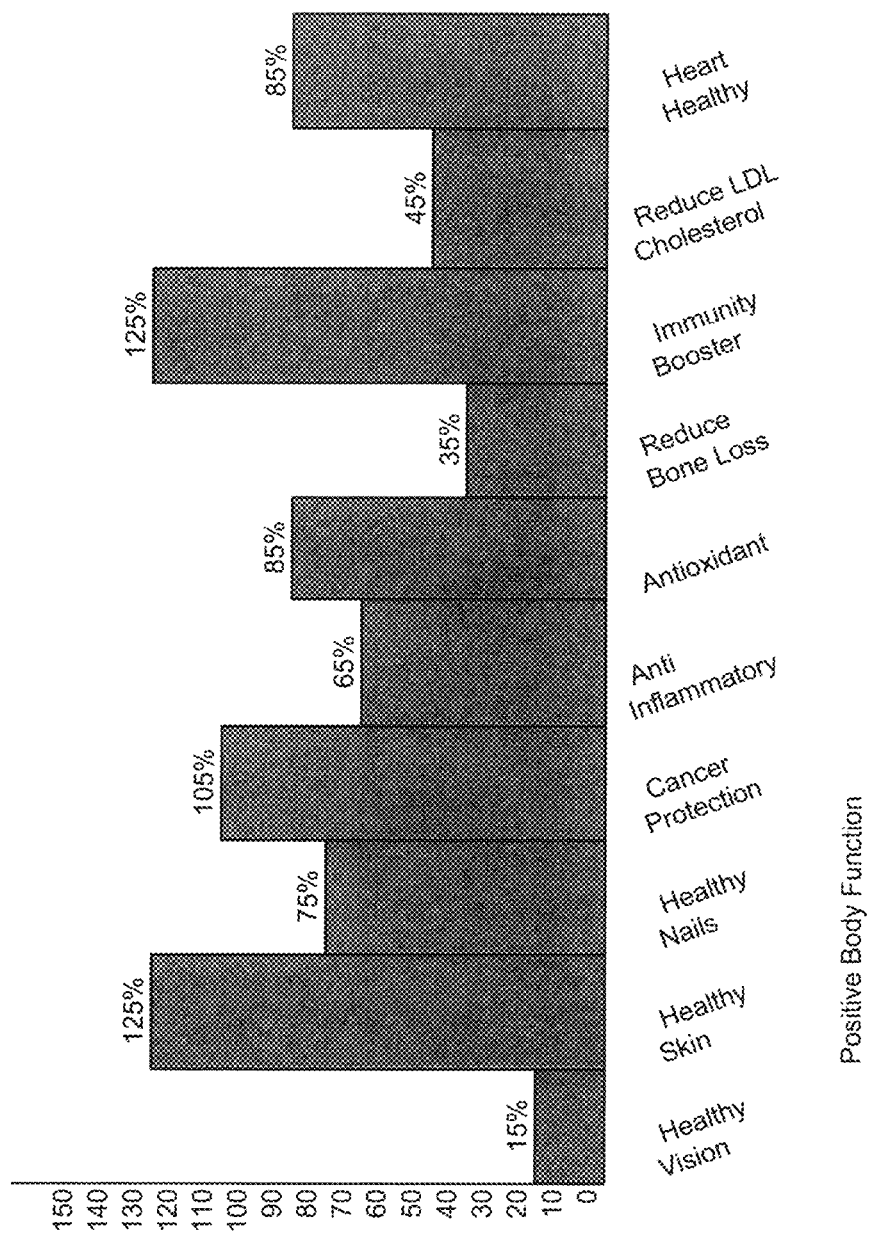
Figure 10E:
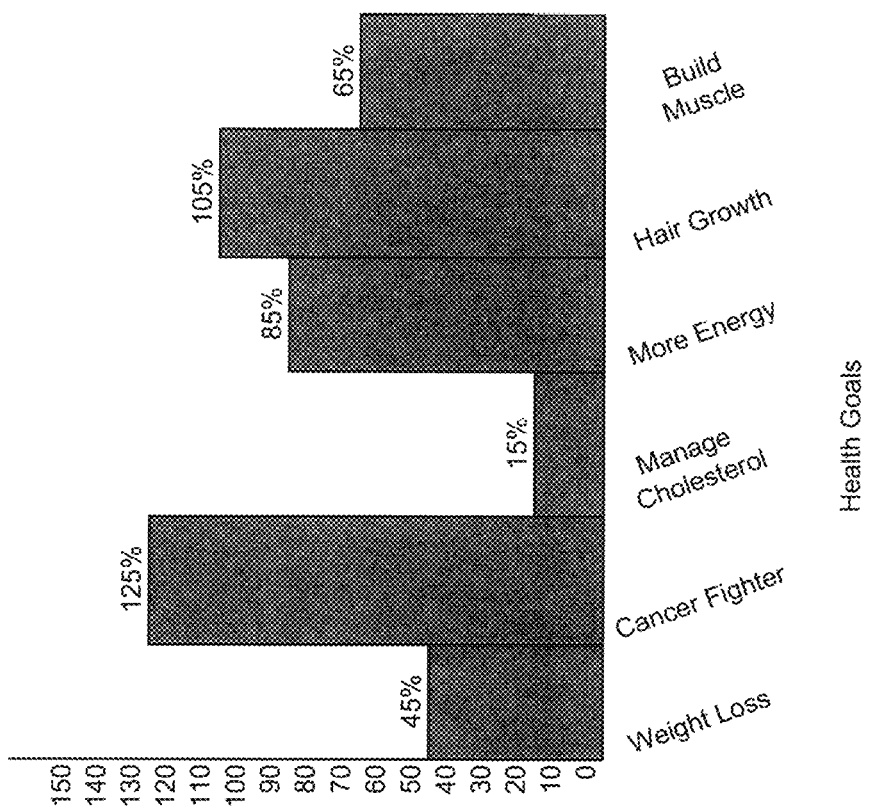
Figure 10F:
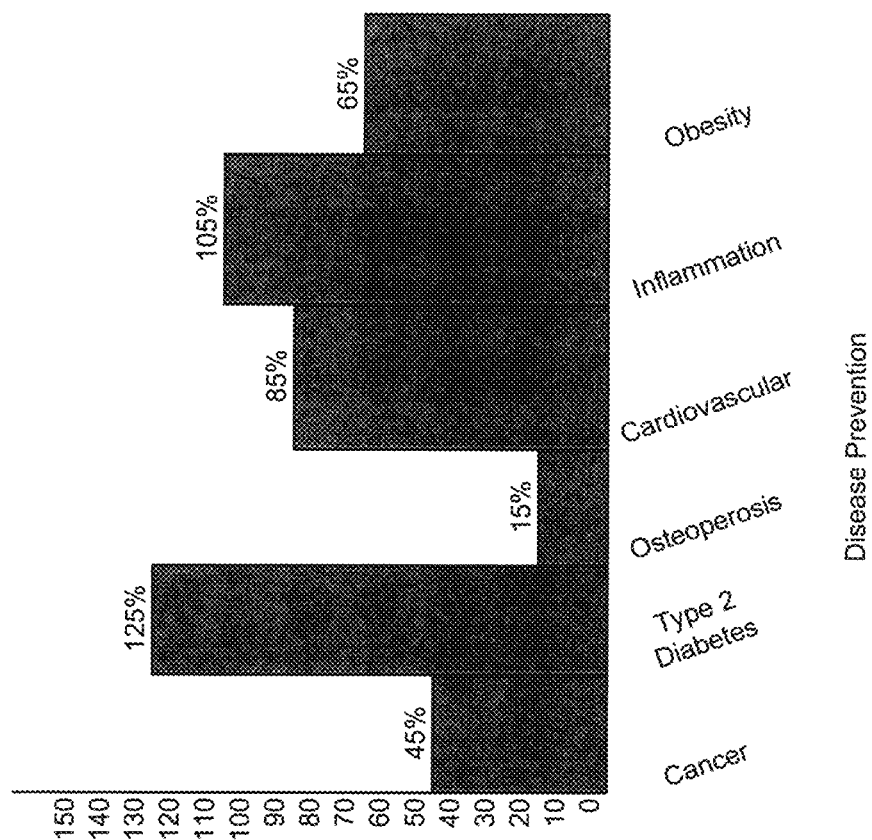

For example, the resulting data for a particular food and respective quantity of food would look like this:

FIG. 10A
890
Minerals
FIG. 10B
891
Vitamins
FIG. 10C
892
Phytochemicals
FIG. 10D
893
Positive Body Function
FIG. 10E
894
Health Goals
FIG. 10F
895
Disease Prevention:
FIG. 10G
896

| | |
|---|---|
| PH | 3.5 |
| Calories | 350 or 15% of daily recommended amount |
| LDL Cholesterol | 30% of daily recommended amount |
| Salt | 25% of daily recommended amount |
| Sugar | 50% of daily recommended amount |

In FIGS. 9A-G the user may be able to research which foods are associated with the various health data categories: Minerals 740, Vitamins 741, Phytochemicals 742, Positive Body Function 743, Health Goals 744 and Disease Prevention 745.

The user may be prompted to select from the various categories 739A, in order to determine which foods are associated with each respective category. Under Minerals 740, the user may see various Minerals: Mineral 1 746, Mineral 2 747, Mineral n 748, where the 'n' designates up to "n" different minerals. Under Mineral 1 746 the user will see Associated Food 1 749, Associated Food 2 752 and Associated Food n 755, where the 'n' designates up to "n" different associated foods. The user can use a link to research all the detailed data (as shown in FIG. 8) on a particular food 761. The user may have the ability to save the foods to favorites 765 or to their meal plans: Breakfast 766, Lunch 767, Dinner 768 and Snacks 769. This same process for reviewing Associated Foods can be replicated for Mineral 1 746-Mineral n 748.

Under Vitamins 741, the user may see various Vitamins: Vitamin 1 770, Vitamin 2 771, Vitamin n 772, where the 'n' designates up to "n" different vitamins. Under Vitamin 1 770 the user may see Associated Food 1 773, Associated Food 2 776 and Associated Food n 779, where the 'n' designates up to "n" different associated foods. The user may use a link to research all the detailed data (as shown in FIG. 8) on a particular food 785. The user will have the ability to save the foods to favorites 789 or to their meal plans: Breakfast 790, Lunch 791, Dinner 792 and Snacks 793. This same process for reviewing Associated Foods can be replicated for Vitamin 2 771-Vitamin n 772.

Under Phytochemicals 742, the user may see various Phytochemicals: Phytochemical 1 794, Phytochemical 2 795, Phytochemical n 796, where the 'n' designates up to "n" different phytochemicals. Under Phytochemical 1 794 the user will see Associated Food 1 797, Associated Food 2 800 and Associated Food n 803, where the 'n' designates up to "n" different associated foods. The user can use a link to research all the detailed data (as shown in FIG. 8) on a particular food 809. The user may have the ability to save the foods to favorites 813 or to their meal plans: Breakfast 814, Lunch 815, Dinner 816 and Snacks 817. This same process for reviewing Associated Foods may be replicated for Phytochemical 2 795-Phytochemical n 796.

Under Positive Body Functions 743, the user may see various Positive Body Functions: Positive Body Functions 1 818, Positive Body Functions 2 819, Positive Body Functions n 820, where the 'n' designates up to "n" different body functions. Under Positive Body Functions 1 818 the user will see Associated Food 1 821, Associated Food 2 824 and Associated Food n 827, where the 'n' designates up to "n" different associated foods. The user can use a link to research all the detailed data (as shown in FIG. 8) on a particular food 833. The user will have the ability to save the foods to favorites 837 or to their meal plans: Breakfast 838, Lunch 839, Dinner 840 and Snacks 841. This same process for reviewing Associated Foods can be replicated for Positive Body Functions 2 819-Positive Body Functions n 820.

Under Health Goals 744, the user may see various Health Goals: Health Goal 1 842, Health Goal 2 843, Health Goal n 844, where the 'n' designates up to "n" different health goals. Under Health Goal 1 842 the user will see Associated Food 1 845, Associated Food 2 848 and Associated Food n 851, where the 'n' designates up to "n" different associated foods. The user may use a link to research all the detailed data (as shown in FIG. 8) on a particular food 857. The user may have the ability to save the foods to favorites 861 or to their meal plans: Breakfast 862, Lunch 863, Dinner 864 and Snacks 865. This same process for reviewing Associated Foods can be replicated for Health Goal 2 843-Health Goals n 844.

Under Disease Prevention 745, the user may see various Disease Prevention: Disease Prevention 1 866, Disease Prevention 2 867, Disease Prevention n 868, where the 'n' designates up to "n" different disease prevention modalities. Under Disease Prevention 1 866 the user may see Associated Food 1 869, Associated Food 2 872 and Associated Food n 875, where the 'n' designates up to "n" different associated foods. The user may use a link to research all the detailed data (as shown in FIG. 8) on a particular food 881. The user may have the ability to save the foods to favorites 885 or to their meal plans: Breakfast 886, Lunch 887, Dinner 888 and Snacks 889. This same process for reviewing Associated Foods can be replicated for Disease Prevention 2 867-Disease Prevention n 868.

It should be understood that the foregoing represents one or more of the preferred and/or exemplary embodiments of the present invention and that numerous other embodiments and variations within the scope and spirit of the appended claims will occur to persons skilled in the art, from a review of this disclosure.

What is claimed is:

1. A method for providing the interactive provision of meal plans to enhance human health goals, including positive body functions, health goals and disease prevention, said method comprising a computerized system for:

receiving via a computerized network user information relating to user demographics and human health goals;
developing a user profile to include options for meals to be selected by the user based upon the received user information;
transmitting to the user the meal options;
receiving from user the meal options selected by the user;

rating the user selected meal options to formulate rating values for the selected meals, wherein the rating values constitute an optimizer score;

transmitting to the user the rating values for the selected meals and allowing the user to revise the options to enhance the rating values for the revised selections;

receiving any revised selected meals from the user; and transmitting to the user any revised rating values for any revised selected meals;

wherein the optimizer score is calculated from the formula:

$$OS=(\% \ DRA(M)\times`20)+(\% \ DRA(V)\times20)+(\% \ DRA(P)\times20)'. \ *(\% \ DRL(PBF)\times20)+(\% \ DRL(HG)\times20)+(\% \ DRL(DP)\times20)+(\% \ DRL(PH)\times20)-[(\% \ over \ DL(C)\times10)+(\% \ over \ DL(SA)\times10)+(\% \ over \ DL(LDL)\times10)+(\% \ over \ DL(SU)\times10)];$$

Where:
'OS' is the Optimizer Score;
'DRA is Daily required amount;
'M' is Minerals;
'V' is Vitamins;
'P' is Phytochemicals;
'PBF' is Positive Body Function;
'DRL' is Daily Required Level;
'HG' is Health Goals;
'DP' is Disease Prevention;
'DL' is Daily Limit;
'C' is Calories;
'SA' is Salt;
'LDL' is LDL Cholesterol;
'SU' is Sugar.

2. The method of claim 1, further comprising: providing to the user, research tools to allow user to make the selection of the meal options.

3. The method of claim 1, further comprising: providing the user an option to add laboratory information to the user information.

4. The method of claim 3, wherein the laboratory information may include blood results, urine results or both of these results.

5. The method of claim 3, wherein the determination of the body functions, the disease preventions or combinations of the foregoing are determined based upon the laboratory information.

6. The method of claim 3, wherein laboratory information may include:
sodium level, potassium level, glucose Level, total protein, calcium serum level, triglyceride level, cholesterol level, HDL, LDL, PSA level, TSH level, PH level, vitamin D, vitamin B12 level, CRP or combinations of the foregoing.

7. The method of claim 1, wherein the user information relating to the human health goals may include healthy vision, budding muscle, more energy, healthy immune system, hair growth, healthy skin, healthy nails, healthy heart, weight loss, managing blood pressure, managing cholesterol, mental sharpness, PH level, cancer fighters, anti-inflammatory, healthy bones, enhanced metabolism, fight type 2 diabetes or combinations thereof.

8. The method of claim 1, wherein the user information relating to positive body function may include cancer protection, anti-inflammatory, antioxidant, reduce bone loss, immunity booster, reduce LDL cholesterol, heart healthy or combinations thereof.

9. The method of claim 1, wherein the user information relating to disease prevention may include cancer, type 2 diabetes, osteoporosis, cardiovascular, inflammation, obesity or combinations thereof.

10. The method of claim 1, further comprising: providing the user the option to purchase customized raw foods, ingredients to make the selected meals, customized prepared meals and combinations thereof.

11. The method of claim 10, wherein the purchased options may be shipped to a selected destination.

12. The method of claim 1, wherein the optimizer score consists of a plurality of levels that delineate how effective the selected meal plans meet the human health goals.

13. The method of claim 1, wherein a score of 140 or over is the genius level, 120-139 is the smarty pants level, 110-119 is the bright level, 90-109 is the average level, 70-89 is the slacker level, 40-69 is the blockhead level and below 40 is the fool level.

14. A computer system embodied on one or more computer readable medium, the computer system adapted to communicate with a communication network and comprising:
computer readable program code configured to —
develop a user profile based upon the user information;
search databases to identify ingredients for meals, raw foods, meals and combinations based upon user information;
identify compliant meals to meet the user information;
transmit to the user, via the communications network, meal information identifying the compliant meals from which the user may make a selection;
receive from the user via the communications network, the meal selections; and
transmit to the user the rating values of the meal selections, wherein the rating values constitute an optimizer score;
wherein the optimizer score is calculated from the formula:

$$OS=(\% \ DRA(M)\times`20)+(\% \ DRA(V)\times20)+(\% \ DRA(P)\times20)'. \ *(\% \ DRL(PBF)\times20)+(\% \ DRL(HG)\times20)+(\% \ DRL(DP)\times20)+(\% \ DRL(PH)\times20)-[(\% \ over \ DL(C)\times10)+(\% \ over \ DL(SA)\times10)+(\% \ over \ DL(LDL)\times10)+(\% \ over \ DL(SU)\times10)];$$

Where:
'OS' is the Optimizer Score;
'DRA is Daily required amount;
'M' is Minerals;
'V' is Vitamins;
'P' is Phytochemicals;
'PBF' is Positive Body Function;
'DRL' is Daily Required Level;
'HG' is Health Goals;
'DP' is Disease Prevention;
'DL' is Daily Limit;
'C' is Calories;
'SA' is Salt;
'LDL' is LDL Cholesterol;
'SU' is Sugar.

15. The computer system of claim 14, wherein the data bases include proprietary data bases for disease prevention, food nutrition, healthy body function, and partner food suppliers.

16. The computer system of claim 14, wherein the computer code is configured to transmit to the user the minerals, vitamins, phytochemicals, positive body functions, benefits towards custom health goals, disease prevention capabilities, PH level, calories, salt level, sugar level and cholesterol level in each meal before deciding whether to eat that food.

17. The computer system of claim 14, wherein the computer code is configured to adjust the information provided as per the quantity of the meal to be eaten.

18. The computer system of claim 14, wherein the computer code is configured to transmit to the user the daily cumulative amount of minerals, vitamins, phytochemicals, positive body functions, benefits towards custom health goals, disease prevention capabilities, PH level, calories, salt level, sugar level and cholesterol level based upon the quantities of the meals eaten.

19. The computer system of claim 17, wherein the computer code is configured to transmit to the user what raw foods, ingredients, meals and quantities are needed to maximize the user's rating score for the balance of the day.

20. The computer system of claim 14, wherein the computer code is configured to transmit to the user recommended raw foods, ingredients and meals that the user will enjoy and will maximize user's Optimizer score based upon the users prior raw food, ingredient and meal selections.

21. The computer system of claim 14, wherein the computer code is configured to transmit to the user the raw foods, meals, their constituent ingredients and quantities associated with achieving each selected health goal.

22. The computer system of claim 19, wherein the computer code is configured to receive from the user his selection of user's favorite raw foods, ingredients and meals, whereupon user's favorites may be included in subsequent suggested raw foods, ingredients and meals.

23. The computer system of claim 14, wherein the computer code is configured to reverse engineer the choice of raw foods, ingredients and meals that will help user achieve user's health goals.

24. A system for providing the interactive provision of raw foods, ingredients and meal plans to enhance human health goals, including positive body functions, health goals and disease prevention, the system comprising:
   a microprocessor;
   a memory coupled to the microprocessor;
   a network interface device operatively connected to the microprocessor for communicating via a communications network; and
   instructions stored in the memory and executable by the microprocessor to:
   develop a profile for user responsive to receipt of user information, said profile being defined as a function of the human health goals and other user input information, said profile including the development of food and meal choices;
   search databases to determine the profile meets the human health goals and other user input information;
   identify compliant foods, meals and rated values for same, to allow user to input his selection of foods and meals;
   transmit to user via the communications network information associated with the compliant meals and their rated values; and
   allow for interactive transmittal of information between the user and the system;
   wherein the rated values are calculated from the formula:

$$OS = (\% \ DRA(M) \times `20) + (\% \ DRA(V) \times 20) + (\% \ DRA(P) \times 20)' \cdot {} ^*(\% \ DRL(PBF) \times 20) + (\% \ DRL(HG) \times 20) + (\% \ DRL(DP) \times 20) + (\% \ DRL(PH) \times 20) - [(\% \ over \ DL(C) \times 10) + (\% \ over \ DL(SA) \times 10) + (\% \ over \ DL(LDL) \times 10) + (\% \ over \ DL(SU) \times 10)];$$

Where:
'OS' is the Optimizer Score;
'DRA is Daily required amount;
'M' is Minerals;
'V' is Vitamins;
'P' is Phytochemicals;
'PBF' is Positive Body Function;
'DRL' is Daily Required Level;
'HG' is Health Goals;
'DP' is Disease Prevention;
'DL' is Daily Limit;
'C' is Calories;
'SA' is Salt;
'LDL' is LDL Cholesterol;
'SU' is Sugar.

\* \* \* \* \*